(12) United States Patent
Zhang et al.

(10) Patent No.: US 12,421,226 B2
(45) Date of Patent: Sep. 23, 2025

(54) HETEROARYL COMPOUNDS AS NECROSIS INHIBITORS, COMPOSITION AND METHOD USING THE SAME

(71) Applicants: Accro Bioscience (HK), Wan Chai (HK); Xiaohu Zhang, Suzhou (CN)

(72) Inventors: Xiaohu Zhang, Suzhou (CN); Sudan He, Suzhou (CN); Haikuo Ma, Suzhou (CN)

(73) Assignee: Accro Bioscience (HK) Limited, Wan Chai (HK)

( * ) Notice: Subject to any disclaimer, the term of this patent is extended or adjusted under 35 U.S.C. 154(b) by 904 days.

(21) Appl. No.: 17/422,168

(22) PCT Filed: Jan. 11, 2020

(86) PCT No.: PCT/US2020/013258
§ 371 (c)(1),
(2) Date: Jul. 9, 2021

(87) PCT Pub. No.: WO2020/146858
PCT Pub. Date: Jul. 16, 2020

(65) Prior Publication Data
US 2022/0112188 A1    Apr. 14, 2022

(30) Foreign Application Priority Data
Jan. 11, 2019 (CN) .......................... 201910026967.X

(51) Int. Cl.
| | | |
|---|---|---|
| C07D 471/04 | (2006.01) | |
| C07D 417/14 | (2006.01) | |
| C07D 495/04 | (2006.01) | |
| C07D 513/04 | (2006.01) | |
| C07D 519/00 | (2006.01) | |

(52) U.S. Cl.
CPC ......... *C07D 471/04* (2013.01); *C07D 417/14* (2013.01); *C07D 495/04* (2013.01); *C07D 513/04* (2013.01); *C07D 519/00* (2013.01)

(58) Field of Classification Search
CPC .................................................. C07D 471/04
See application file for complete search history.

(56) References Cited

U.S. PATENT DOCUMENTS

2017/0158690 A1 *  6/2017  Wu .......................... A61P 25/30

FOREIGN PATENT DOCUMENTS

| WO | WO-2011022439 A1 * | 2/2011 | ........... A61K 31/422 |
|---|---|---|---|
| WO | 2018017435 A1 | 1/2018 | |
| WO | 201823370 A1 | 12/2018 | |

OTHER PUBLICATIONS

Pennington, L. D. "The Necessary Nitrogen Atom: A Versatile High-Impact Design Element for Multiparameter Optimization" J. Med. Chem. 2017, 60, 3552-3579.*
Hao, "Discovery, optimization and evaluation of isothiazolo[5,4-b]pyridine derivatives as RIPK1 inhibitors with potent in vivo anti-SIRS activity." Bioorganic Chemistry, 2022, 129, 106051.*
Sedger "TNF and TNF-receptors: From mediators of cell death and inflammation to therapeutic giants—past, present and future" Cytokine & Growth Factor Reviews 25 (2014) 453-472.*
Yang "Ferroptosis: Death by Lipid Peroxidation" Trends in Cell Biology, Mar. 2016, vol. 26, No. 3 165-175.*
Pasparakis "Necroptosis and its role in inflammation" Nature, 2015, 517, 311-320.*
Bae, Cancer Targeted Drug Delivery, Springer: New York, 2013, p. v.*
Hayat, M.A. Autophagy Cancer, Other Pathologies, Inflammation, Immunity, Infection, and Aging vol. 5 Academic Press: San Diego, 2015, p. xxi.*
Carlo C. Maley and Mel Greaves Frontiers in Cancer Research Springer: 2016, pp. 18-19.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
A.M. Bendele "Animal models of rheumatoid arthritis" J Musculoskel Neuron Interact 2001; 1(4):377-385.*
Poli-de-Figueiredo "Experimental Models of Sepsis and Their Clinical Relevance" Shock, vol. 30, Supplement 1, pp. 53-59, 2008.*

(Continued)

*Primary Examiner* — David K O'Dell

(57) ABSTRACT

The present disclosure provides heteroaryl compounds of Formula (I), processes for their preparation, pharmaceutical compositions containing them, and their use in the treatment of diseases and disorders, arising from or related to necrosis. Formula (I) is shown below:

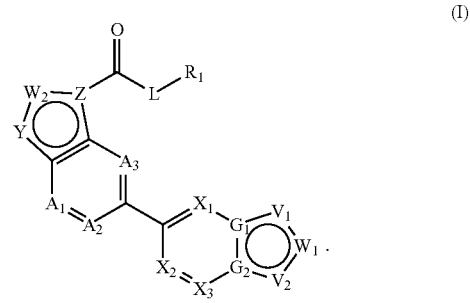

4 Claims, 1 Drawing Sheet

(56) References Cited

OTHER PUBLICATIONS

Gentile "HMGB1 as a therapeutic target for sepsis: it's all in the timing!" Expert Opinion on Therapeutic Targets, 2014, 18:3, 243-245.*
Marshall "Why have clinical trials in sepsis failed?" Trends in Molecular Medicine, Apr. 2014, vol. 20, No. 4 195-203.*
Garrido "Experimental models of sepsis and septic shock: an overview" Acta Cirúrgica Brasileira—vol. 19 (2) 2004 82-88.*
University of Cambridge John van Geest Centre for Brain Repair School of Clinical Medicine "Alzheimer's disease and tauopathy" Online "http://www.brc.cam.ac.uk/research/alzheimers-disease-and-tauopathy" accessed Sep. 10, 2015.*
Tomohiro Chiba "Emerging Therapeutic Strategies in Alzheimer's Disease" Intech 2013, 181-225.*
Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

* cited by examiner

HETEROARYL COMPOUNDS AS NECROSIS INHIBITORS, COMPOSITION AND METHOD USING THE SAME

CROSS REFERENCE TO RELATED APPLICATIONS

This application claims the benefit of Chinese Patent Applications 201910026967.X, filed on Jan. 11, 2019; which is hereby incorporated by reference in its entirety.

FIELD OF INVENTION

The present invention generally relates to heteroaryl compounds and, more particularly, relates to novel heteroaryl compounds that are useful in the therapies targeting necrosis mediated diseases, including inflammatory diseases, tumors, metabolic diseases, and neurodegenerative diseases such as cerebral ischemia and stroke, in mammals.

BACKGROUND OF THE INVENTION

Different types of cell death are often defined by morphological criteria, and are classified as apoptosis and necrosis, two of the basic types. Apoptosis is characterized by cell shrinkage, chromatin condensation, the increased activities of cysteinyl aspartate-specific proteases or caspases, and the controlled breakdown of the cell into apoptotic bodies. Because apoptosis is usually physiological aberrations, it is not inflammatory. Necrosis is thought to begin with an impairment of the cell's ability to maintain homeostasis, continue to cause damage of the plasma membrane integrity, and lead to cytoplasmic and organelle swelling and the eventual lysis of the cell. Due to the release of cytoplasmic contents into the surrounding extracellular space, necrosis usually results in inflammatory response.

Early studies considered necrosis as an accidental and uncontrolled form of cell death lacking underlying signaling events. But later studies has shown that when stimulated by pro-inflammatory cytokines such as tumor necrosis factor-α (TNF-α), some cells choose the necrotic pathway instead of the apoptotic pathway. Such cell types include L929 murine fibroblasts and the NIH 3T3N murine fibroblasts. Recent research on the function of RIP1/RIP3 in TNF-α promoted necrosis pathway laid the foundation to elucidate the mechanism of necrosis. See Cho Y. S. et al., *Cell* 2009; 137(6): 1112-23; Zhang D. W. et al., *Science* 2009, 325(5938): 332-6; He, S. et al., Nat. Immunolo. *Cell* 2009; 137(6): 1100-11.

When the apoptosis pathway is malfunctioned or inhibited, the necrosis pathway can be activated. A ripotosome complex formed by RIP1, fas-associating death domain (FADD) and caspase-8 can promote phosphorylation of RIP3. Then upon RIP3 phosphorylation of Thr357 and Ser358 in mixed lineage kinase like (MLKL), MLKL shifts from its monomeric state to an active oligomeric state. The oligomeric MLKL can bind to phosphoinositol and myocardial phospholipid so that the necrosome complex can move from cytoplasm to cell membrane or organelle membrane, and form permeable channels in the membrane structure, destroy the membrane integrity, and induce cell death.

In addition, phosphorylated RIP3 can interact with downstream bioenergetics enzymes including glycogen phosphorylase (PYGL), glutamate-ammonia ligase (GLUL) and glutamate dehydrogenase 1 (GLUD1), thereby enhancing their catalytic activity. Enhanced glycogenolysis and glutaminolysis can provide additional respiratory substrates, such as phosphorylated glucose and ketoglutarate, accelerate mitochondrial citric acid cycle, and ultimately result in the overgeneration of reactive oxygen species (ROS). Excess ROS, in turn, can trigger mitochondrial membrane permeabilization (MMP), thereby mediating TNF-induced programmed necrosis. Therefore, inhibition of necrosis may become a potential target for the treatment of metabolic diseases, such as diabetes.

Programmed necrosis may be involved in cell death associated with lesions of neurons and glial cells—the most essential components of the central nervous system. Many research projects indicate that inhibition of programmed necrosis may protect the nervous system. Some research programs seek to reduce harms to nervous system by reversing the necrosis and mitigating tissue damage. Accordingly, inhibition of necrosis often becomes the target of treatment for injuries to the nervous system. For example, in ischemic stroke, loss of cerebral circulation may lead to local or total cerebral ischemia and hypoxia. The ensuing death of large number of neurons may affect their corresponding nerve motor function. Consequently reducing the death of neurons may become the objective for the treatment of ischemic stroke.

Accordingly, in order to improve the afore-mentioned diseases caused by necrosis, there is a need for effective inhibitors of necrosis.

SUMMARY OF THE INVENTION

The present disclosure provides heteroaryl compounds as inhibitors of necrosis, and compositions and applications thereof. These disclosed heteroaryl compounds, and compositions and applications thereof, may effectively inhibit necrosis, thereby finding application in treatments of necrotic pathway-related diseases and disorders, including, for example, inflammation, tumors, metabolic diseases and neurodegenerative diseases such as cerebral ischemia and stroke.

An aspect of the present disclosure provides a compound of Formula (I):

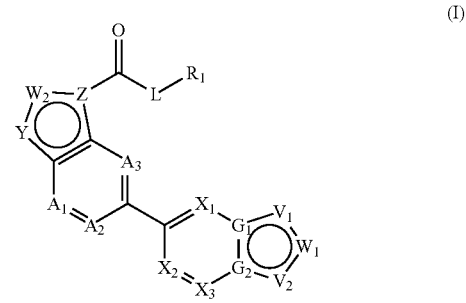

or a stereoisomer, hydrate, ester, solvate, co-crystal, metabolite, stereoisomer or tautomer, or pharmaceutically acceptable salt thereof, wherein $A_1$, $A_2$ and $A_3$ are independently N or $CR_2$;
$X_1$, $X_2$ and $X_3$ are independently N or $CR_3$;
$G_1$ and $G_2$ are independently N or C;
$V_1$ and $V_2$ are independently N, O, S, $NR_4$ or $CR_4$;
$W_1$ is $V_3$, $V_4$—$V_5$ or $V_4$=$V_5$; $V_3$, $V_4$ and $V_5$ are independently N, O, S or $CR_5$, wherein $V_4$ connects with $V_1$, and $V_5$ connects with $V_2$;

$W_2$ is $V_6$ or $V_7=V_8$; $V_6$, $V_7$ and $V_8$ are independently N, O, S, $NR_6$ or $CR_6$, wherein $V_7$ connects with Z, and $V_8$ connects with Y;

Y is N, O, S, S(=O), S(=O)$_2$, $NR_6$ or $CR_6$;

Z is C or N, with the proviso that when Z is N, $V_6$ and Y are not $NR_6$;

L is a bond, O, S, $NR_{11}$ or $CR_{11}R_{12}$;

$R_1$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_9$, wherein each hetero atom is independently N, O or S;

each of $R_2$, $R_3$, $R_4$ and $R_6$ is independently selected from the group consisting of H, deuterium, halide, —CN, —OH, amino, $C_{1-6}$ alkoxy, $C_{1-6}$ alkylamino, $C_{1-6}$ alkylthio, $C_{3-6}$ cycloalkyl, $C_{1-6}$ alkyl, 3-8 membered heterocycle comprising 1-3 hetero atoms, phenyl or 5-6 membered heteroaryl comprising 1-3 hetero atoms, wherein each of the $C_{1-6}$ alkoxy, $C_{1-6}$ alkylamino, $C_{1-6}$ alkylthio, $C_{3-6}$ cycloalkyl, $C_{1-6}$ alkyl, 3-8 membered heterocycle, phenyl and 5-6 membered heteroaryl is unsubstituted or substituted with 1-3 deuterium, halide, $C_{1-3}$ alkyl or $C_{1-3}$ alkoxy, wherein each hetero atom is independently N, O or S;

$R_5$ is H, deuterium, halide, —CN, —OH, $C_{1-6}$ alkoxy, $C_{1-6}$ alkyl; $C_{3-6}$ cycloalkyl or —$NR_7R_8$;

$R_7$ is H, $C_{1-6}$ alkyl or $C_{3-6}$ cycloalkyl;

$R_8$ is H, C(=O)$R_{10}$, C(=O)$NR_{10}R_{11}$, C(=O)$OR_{10}$, S(=O)$_2R_{10}$, S(=O)$_2NR_{10}R_{13}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups selected from the group consisting of halide, deuterium, —CN, $C_{1-6}$ alkyl, $C_{3-6}$ cycloalkyl, $C_{1-6}$ alkoxy and 3-6 membered heterocycle comprising 1-3 hetero atoms, each hetero atom is independently N, O or S;

$R_9$ is H, deuterium, halide, —OH, oxy, —CN, -amino, $C_{1-6}$ alkyl, $C_{3-6}$ cycloalkyl or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups selected from the group consisting of deuterium, halide and $C_{1-3}$ alkyl;

each of $R_{10}$ and $R_{13}$ is independently H, $C_{1-6}$ alkyl, $C_{2-6}$ alkenyl, $C_{2-6}$ alkynyl, $C_{3-6}$ cycloalkyl, phenyl, 3-6 membered heterocycle comprising 1-3 hetero atoms, or 5-6 membered heteroaryl comprising 1-3 hetero atoms, wherein each of $C_{1-6}$ alkyl, $C_{2-6}$ alkenyl, $C_{2-6}$ alkynyl, $C_{3-6}$ cycloalkyl, phenyl, 3-6 membered heterocycle and 5-6 membered heteroaryl is unsubstituted or substituted with 1-3 groups selected from the group consisting of deuterium, halide, —CN, —OH, —CF$_3$, $C_{1-6}$ alkyl, $C_{1-6}$ alkoxy, $C_{3-6}$ cycloalkyl and 5-6 membered heteroaryl comprising 1-3 hetero atoms, each hetero atom is independently N, O or S; or $R_{10}$ and $R_{13}$ together, with nitrogen atom they attached to, form a 4-6 membered ring; or $R_{10}$ and $R_4$ together, with adjacent atoms they attached to, form a 5-6 membered ring; and $R_{11}$ and $R_{12}$ are independently H, halide, —OH, $C_{1-3}$ alkyl or $C_{1-6}$ alkoxy.

In some embodiments of aspects provided herein, L is a bond, $CH_2$, O or NH. In some embodiments, each of $V_3$ and $V_5$ is independently $CNR_7R_8$. In some embodiments, wherein subgroup

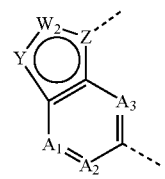

is selected from the group consisting of

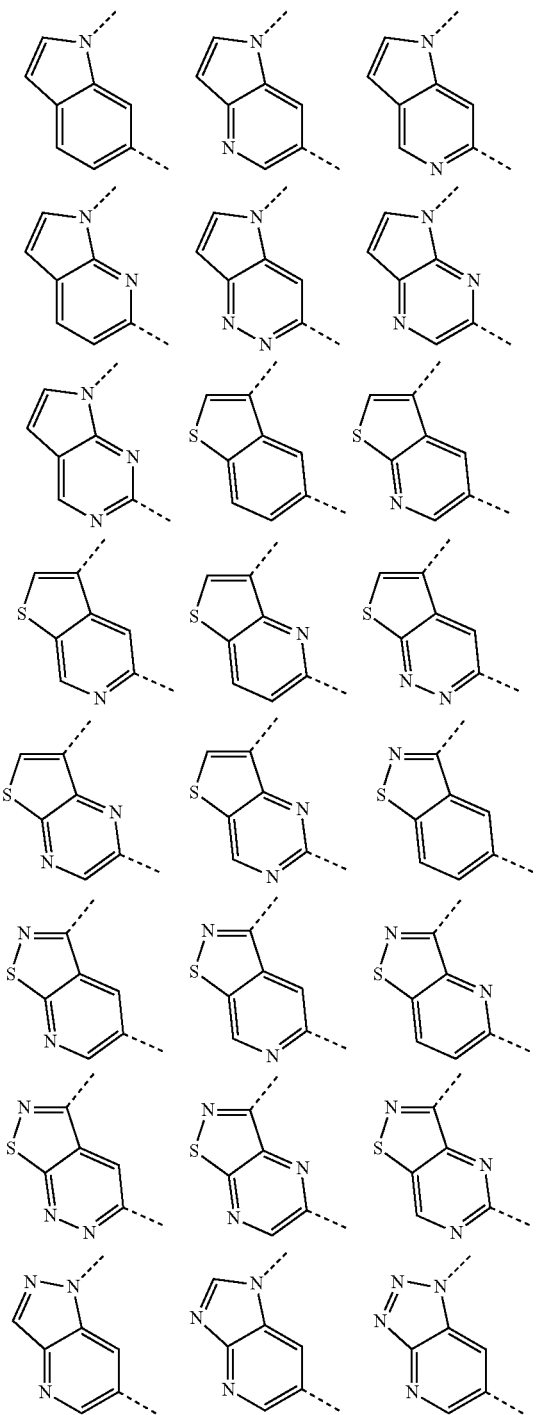

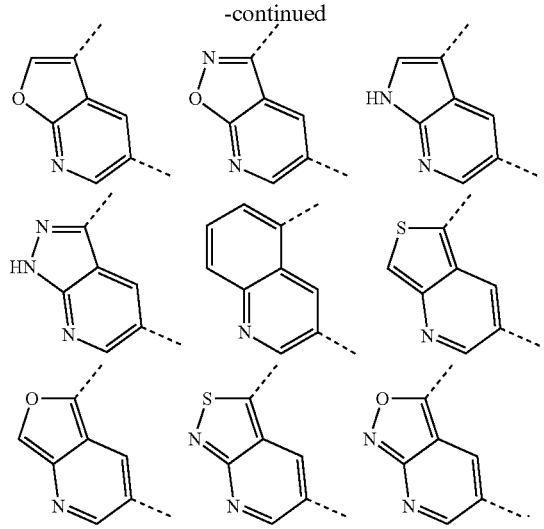
In some embodiments, subgroup
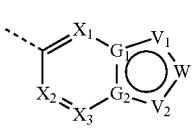
is selected from the group consisting of:
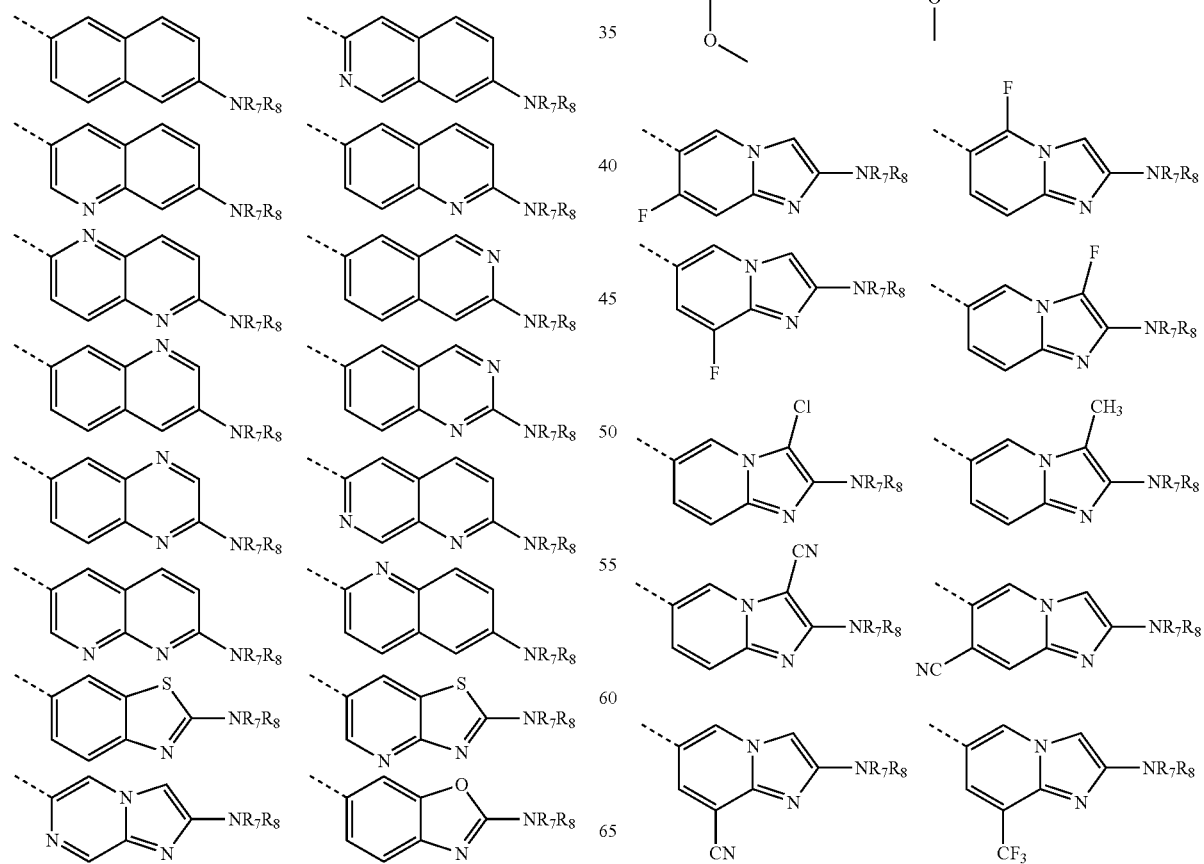
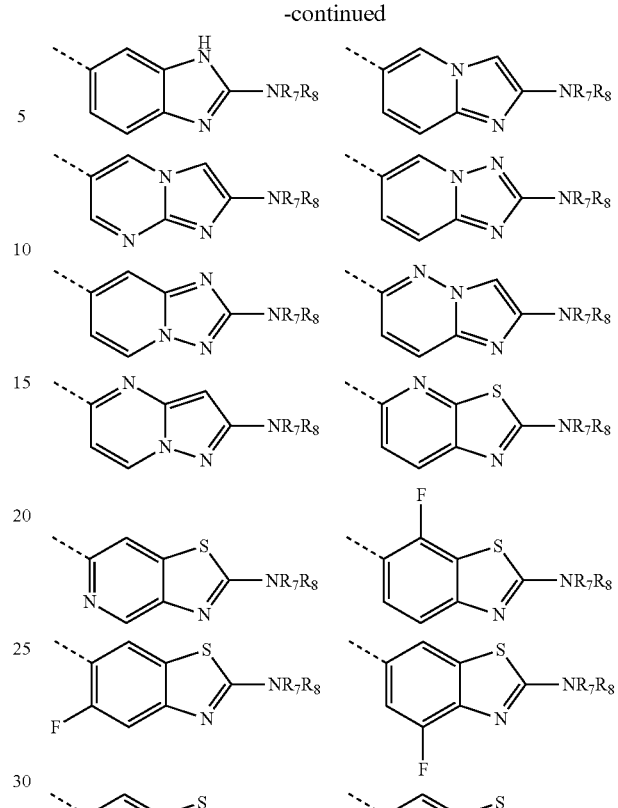

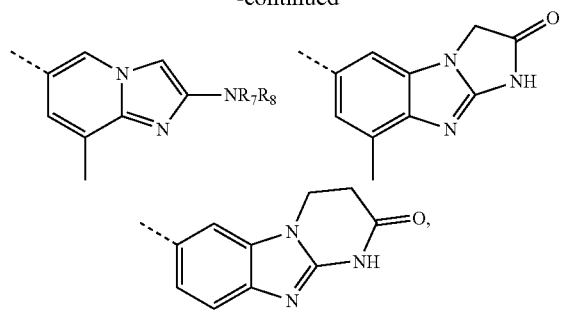
wherein the subgroup
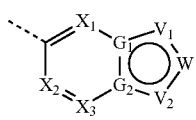
is unsubstituted or substituted with 1 or 3 groups of $R_{14}$, wherein $R_{14}$ is independently deuterium, halide, —CN, —OH, amino, $C_{1-6}$ alkoxy, $C_{1-6}$ alkylthio, $C_{3-6}$ cycloalkyl, or $C_{1-6}$ alkyl.
In some embodiments, $R_1$ is selected from the group consisting of:
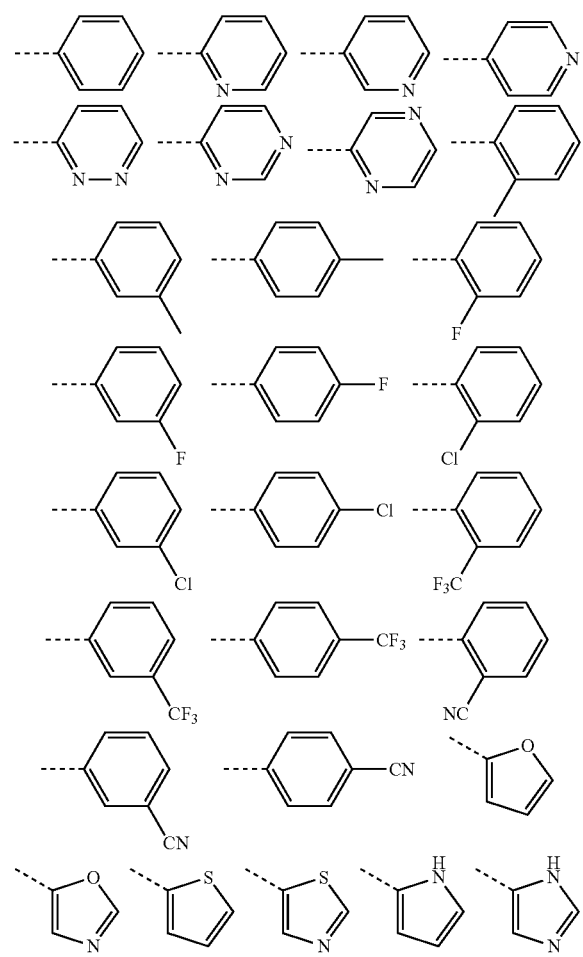
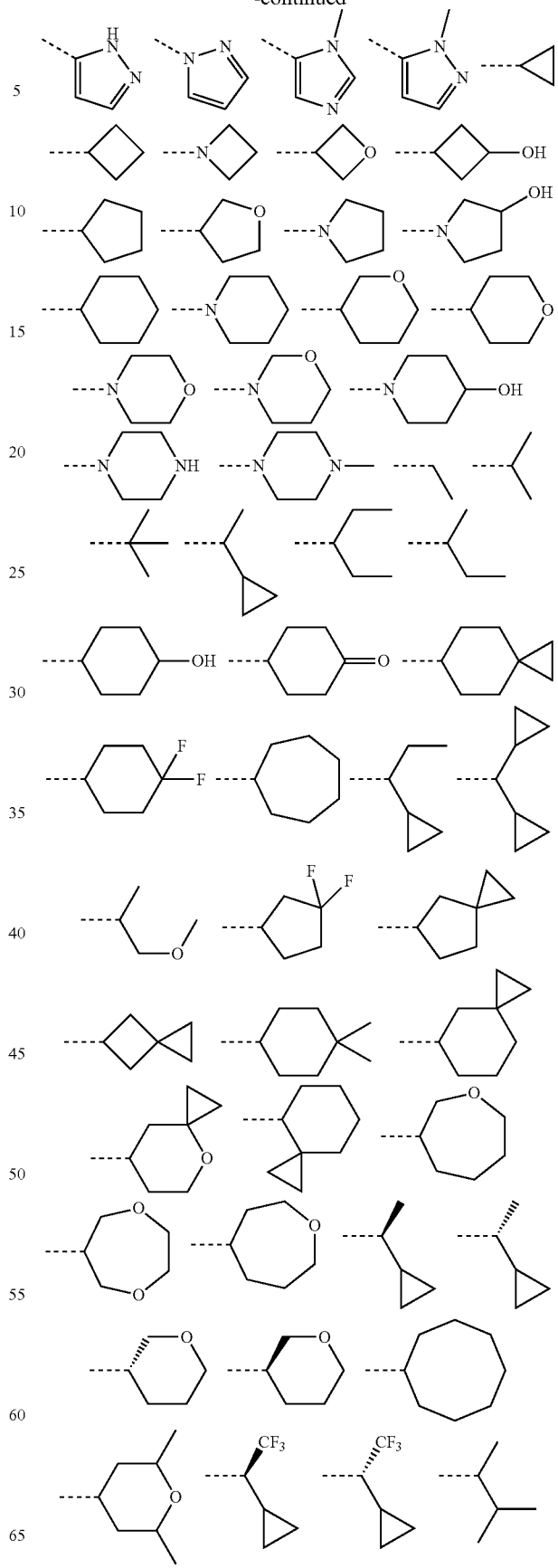

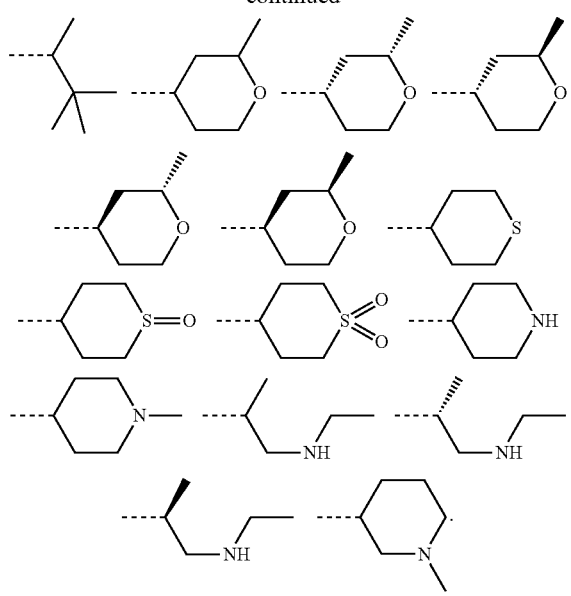
In some embodiment, $R_8$ is selected from the group consisting of:
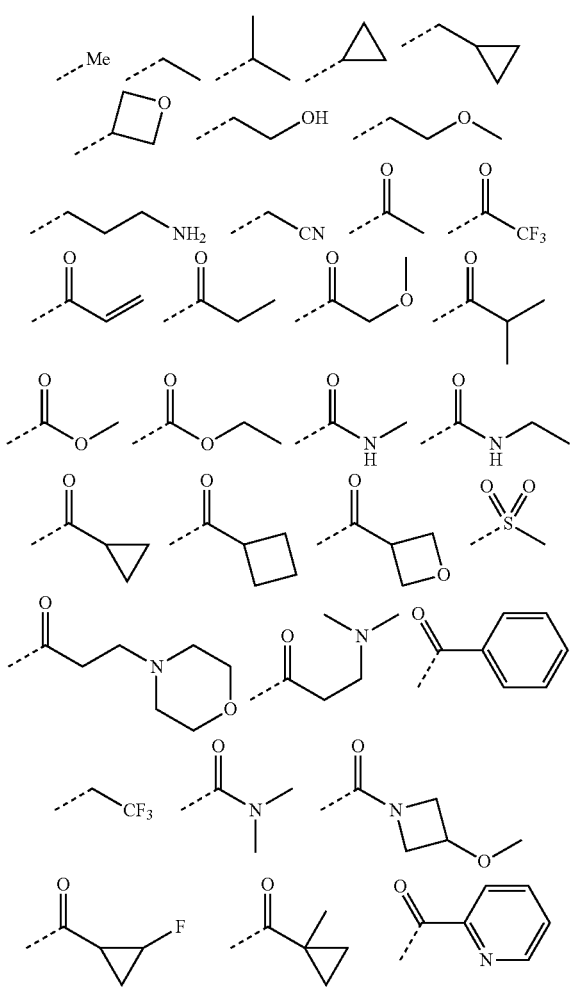
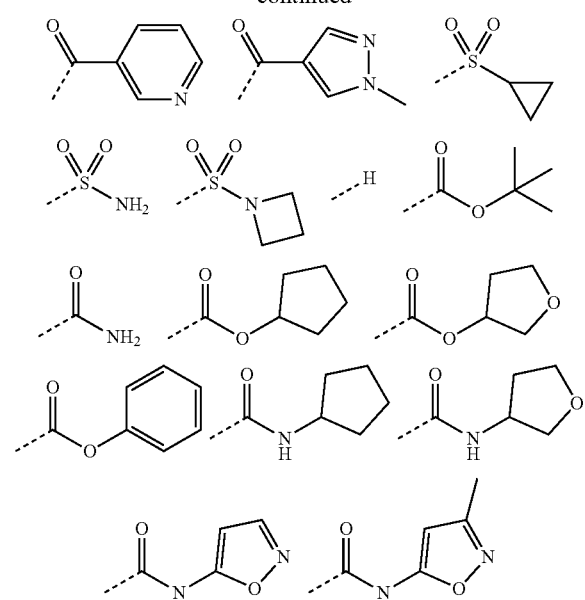
In some embodiments, the compound is selected from the group consisting of:
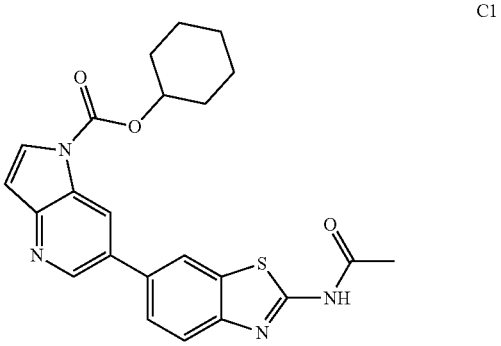

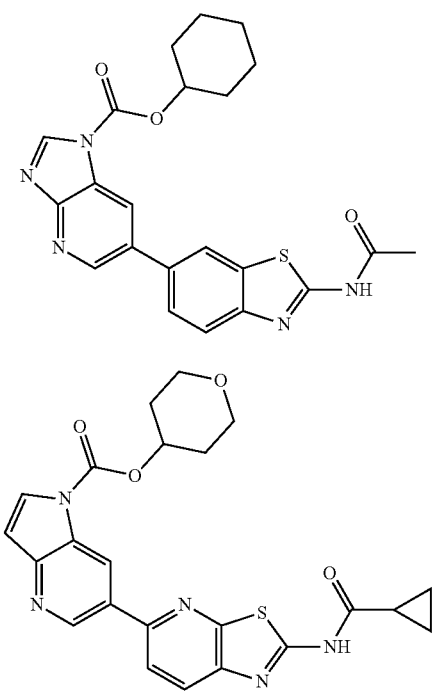
C2
C3
C4
C5
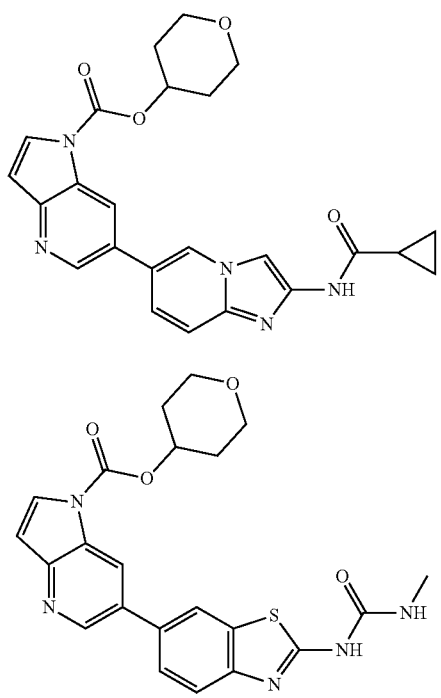
C6
C7
C8
C9

C10
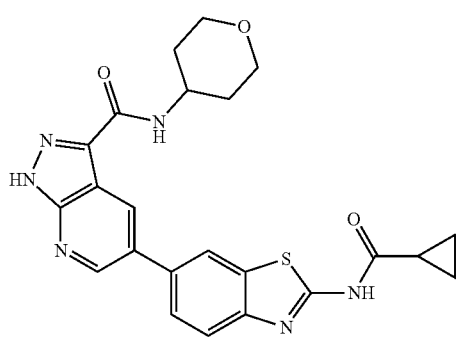
C11
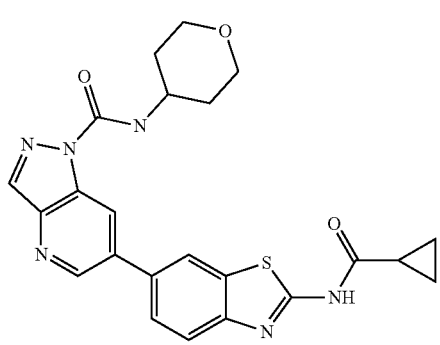
C12
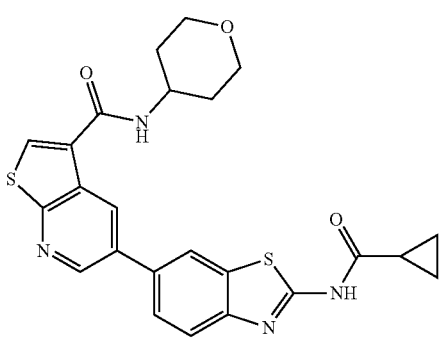
C13
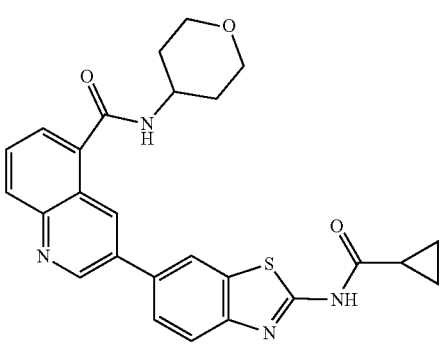
C14
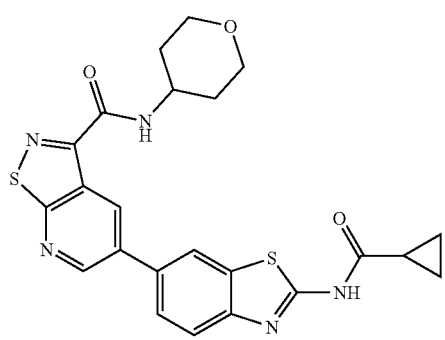
C15
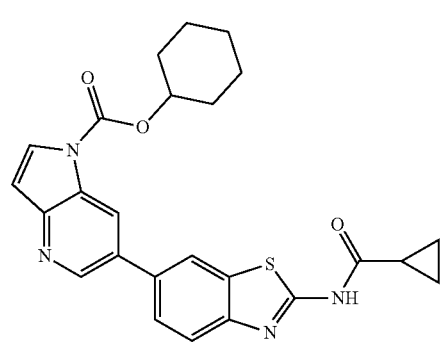
C16
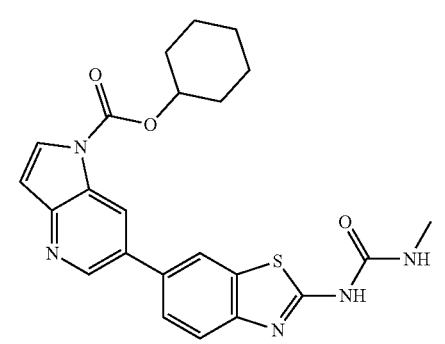
C17
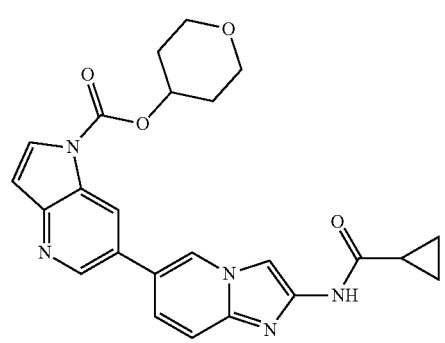

C18
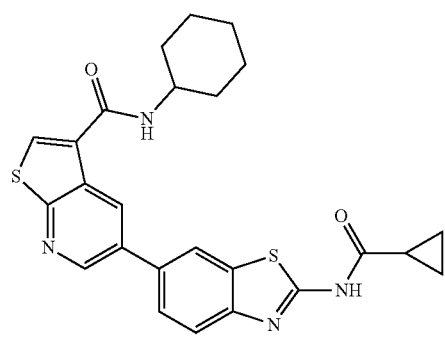
C19
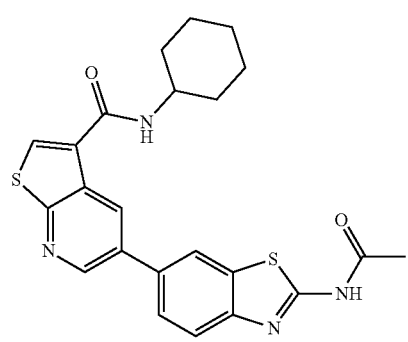
C20
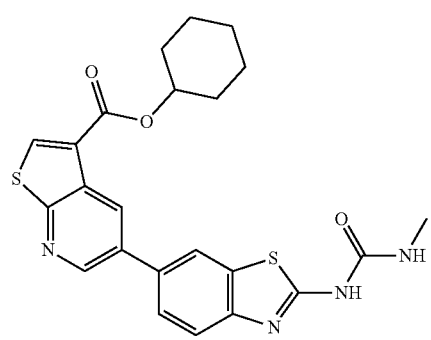
C21
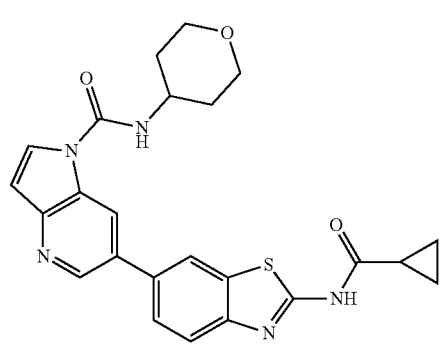
C22
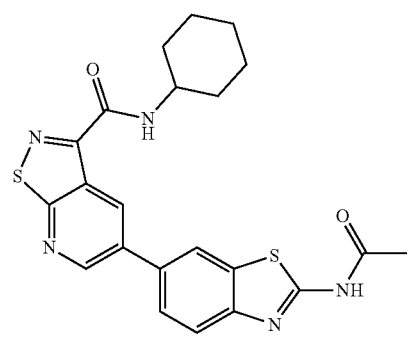
C23
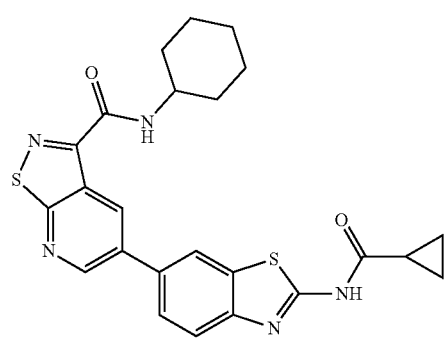
C24
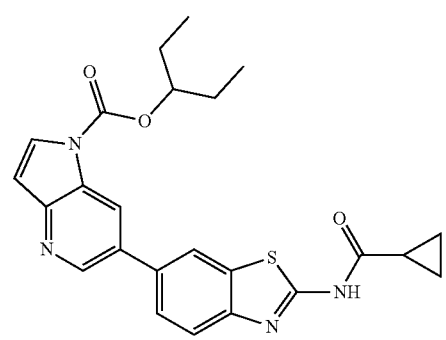
C25
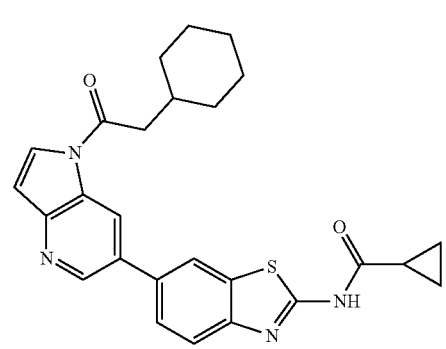

-continued
C26
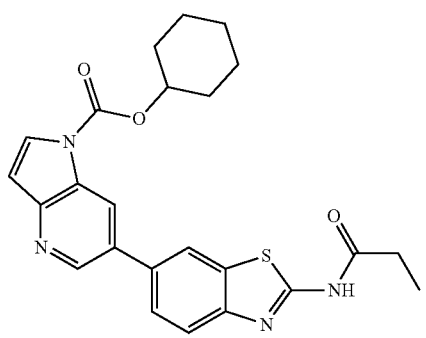
C27
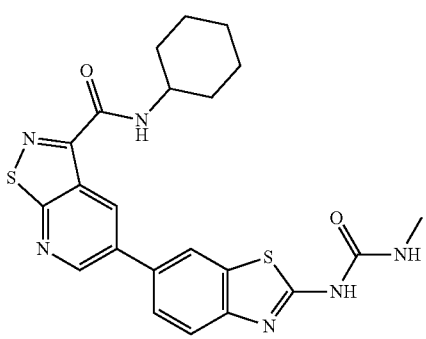
C28
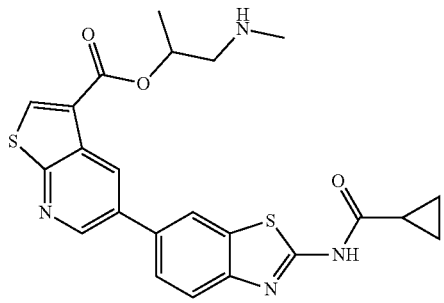
C29
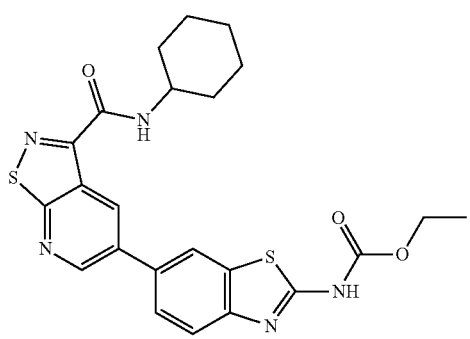
-continued
C30
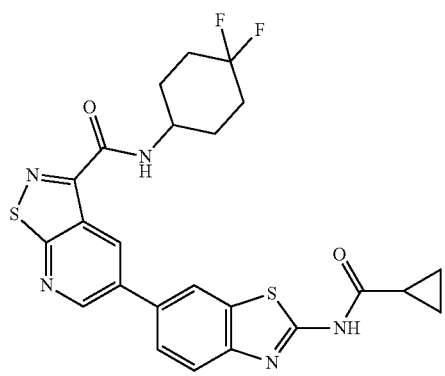
C31
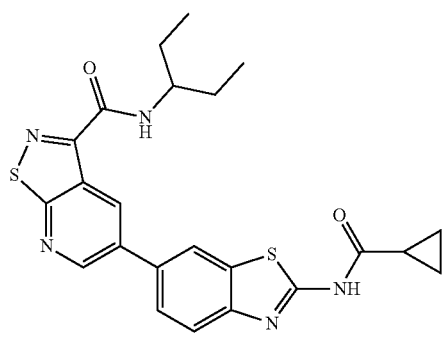
C32
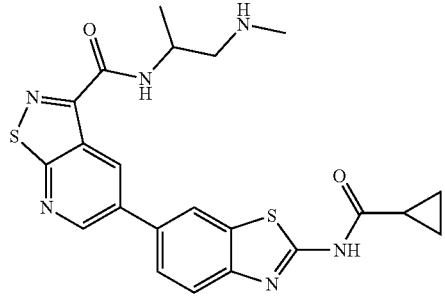
C33
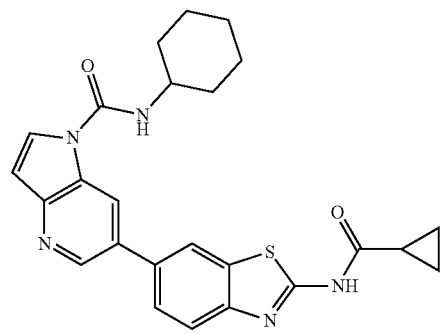

-continued
C34
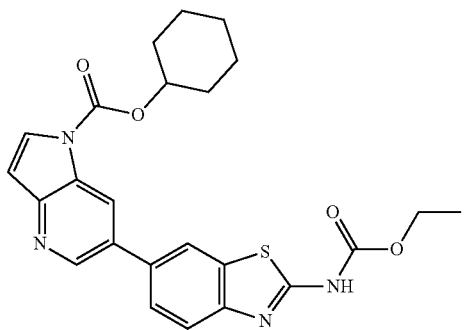
C35
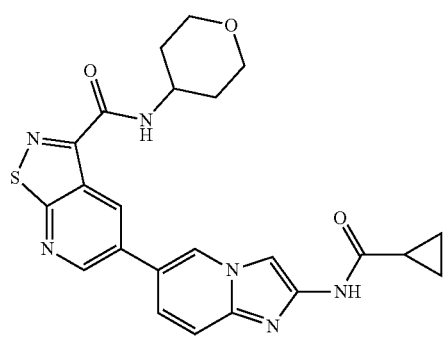
C36
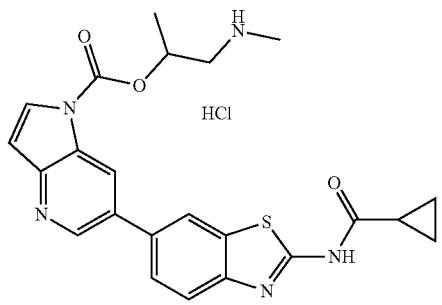
C37
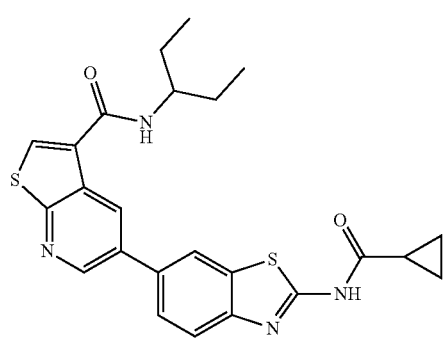
-continued
C38
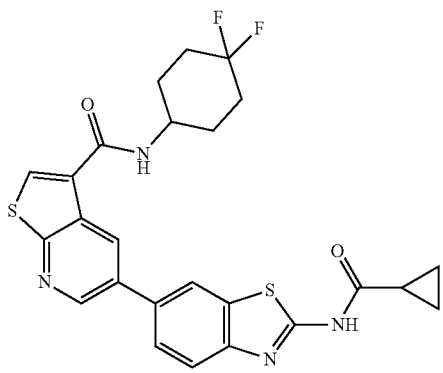
C39
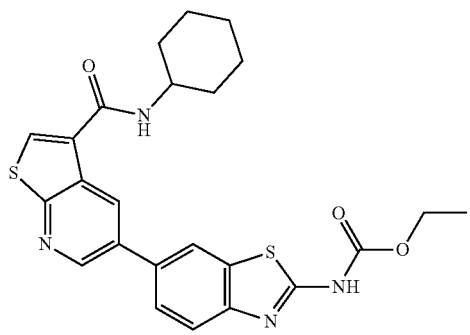
C40
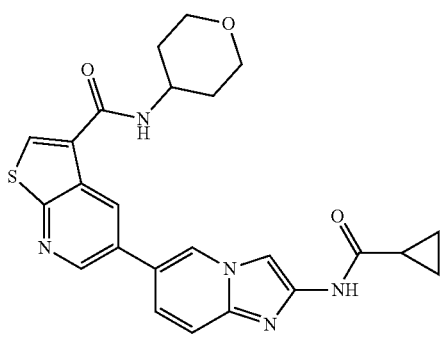
C41
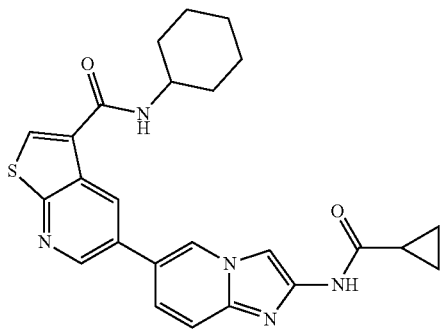

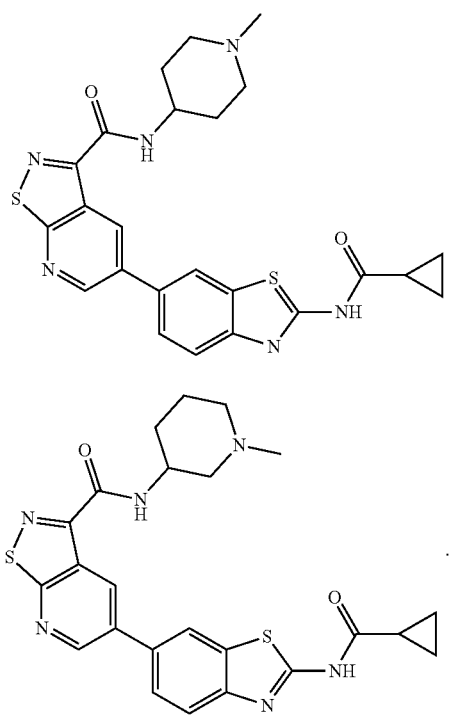
C42
C43
In some embodiments of aspects provided herein, subgroup
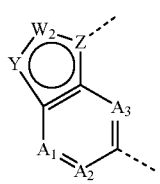
is selected from the group consisting of:
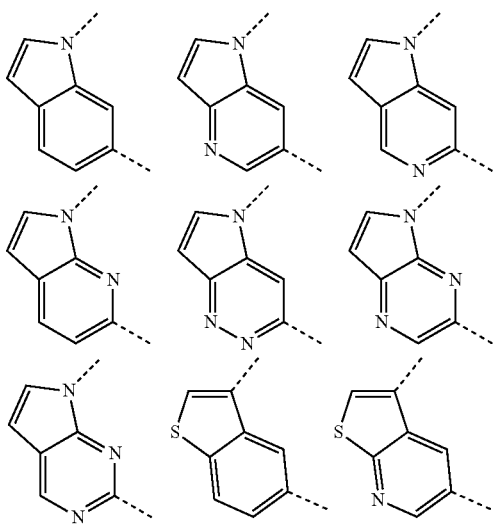
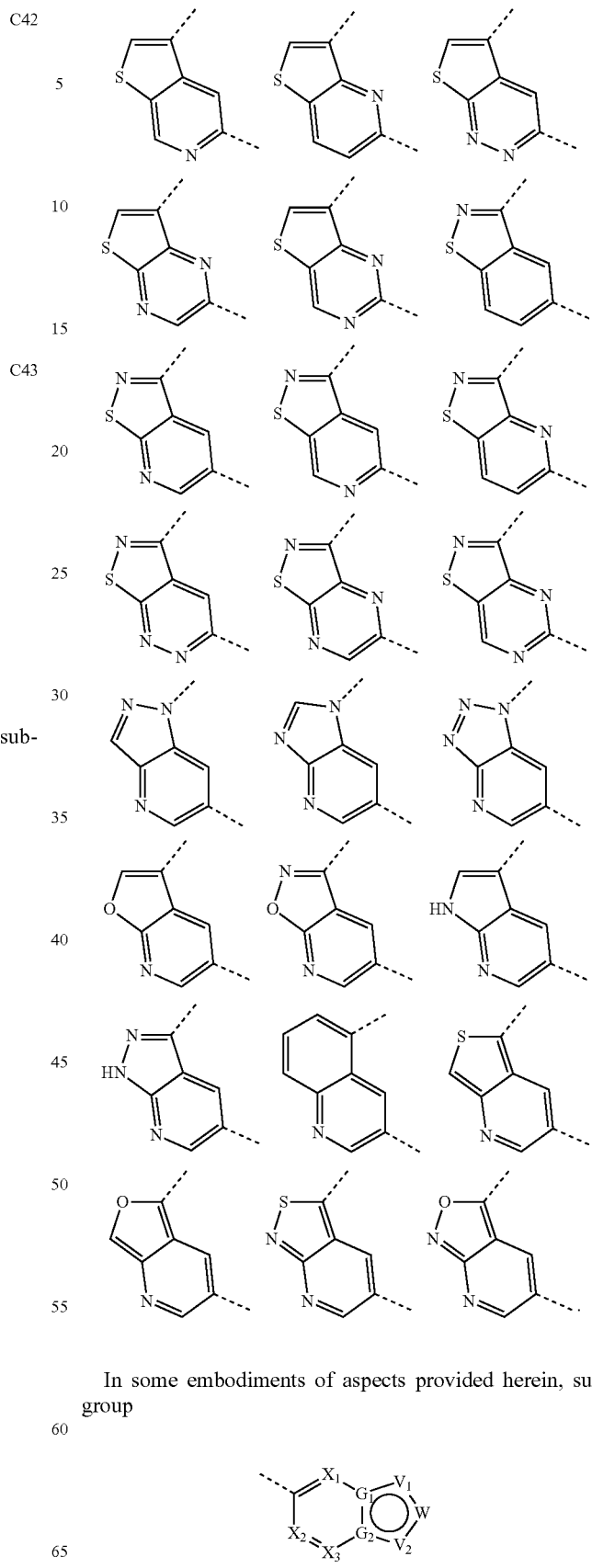
In some embodiments of aspects provided herein, subgroup is selected from the group consisting of:
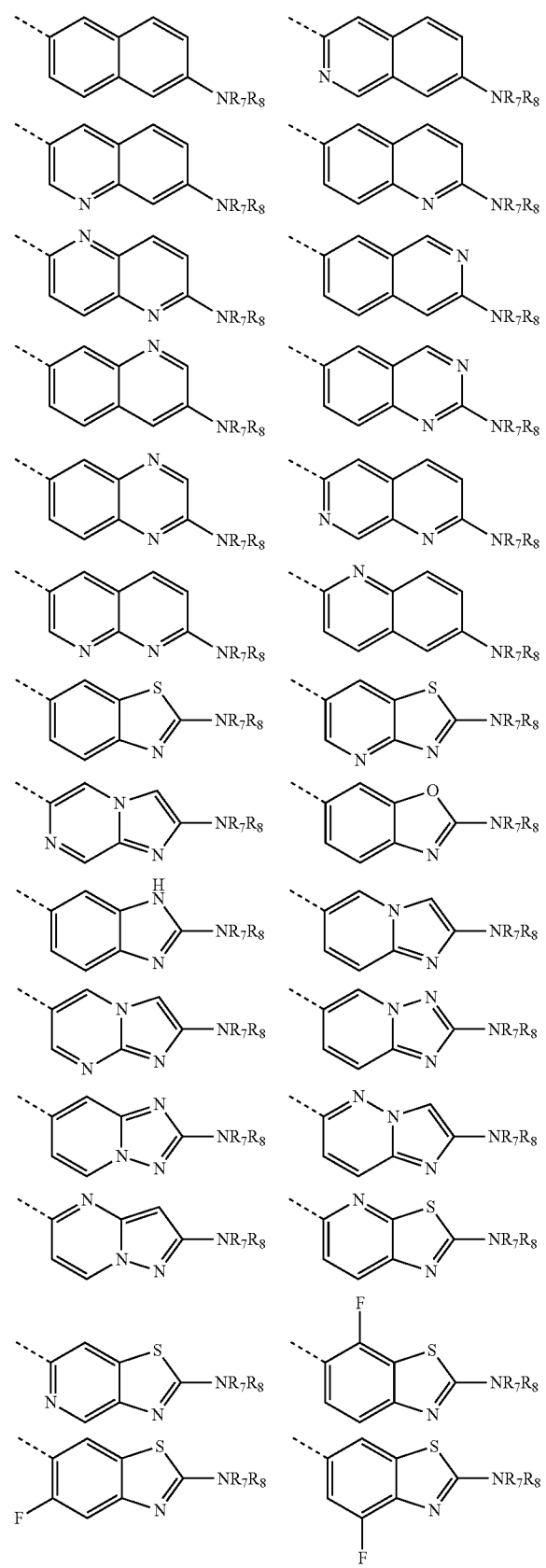
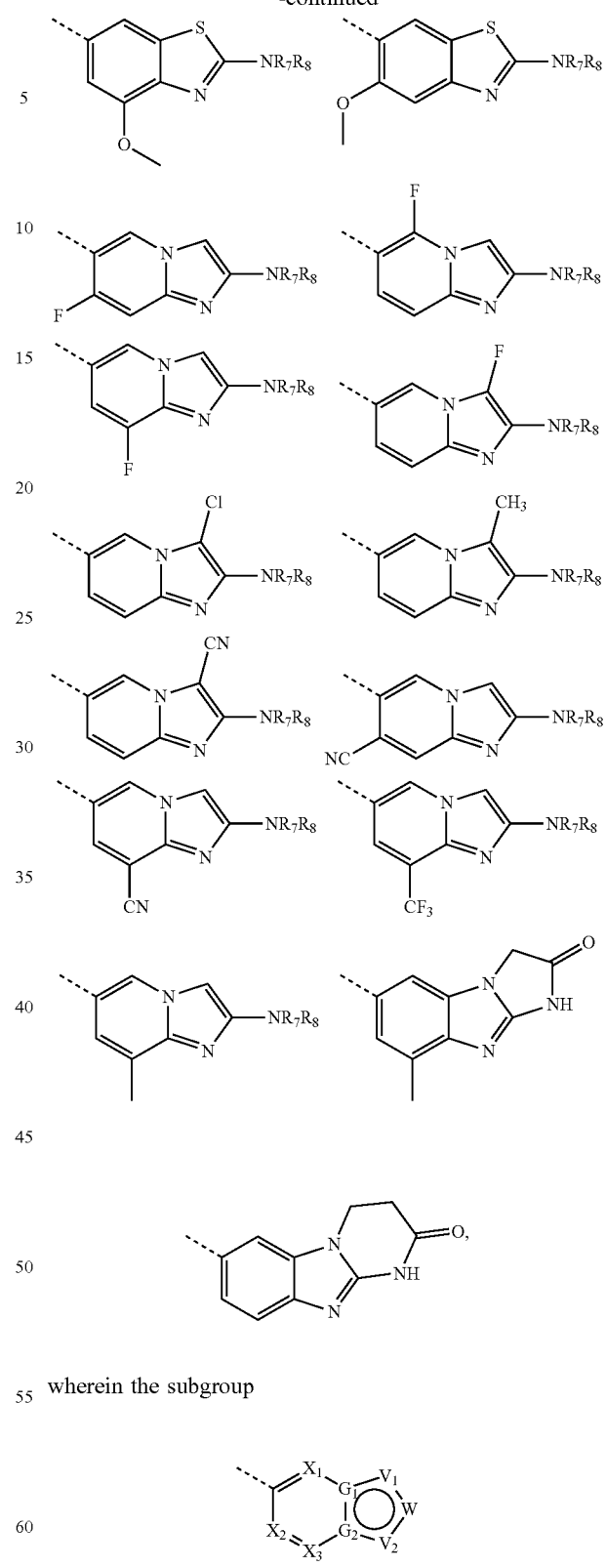
wherein the subgroup
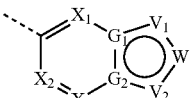
is unsubstituted or substituted with 1 or 3 groups of $R_{14}$, wherein $R_{14}$ is independently deuterium, halide, —CN, —OH, amino, $C_{1-6}$ alkoxy, $C_{1-6}$ alkylthio, $C_{3-6}$ cycloalkyl, or $C_{1-6}$ alkyl.

In some embodiments of aspects provided herein, $R_1$ is selected from the group consisting of:
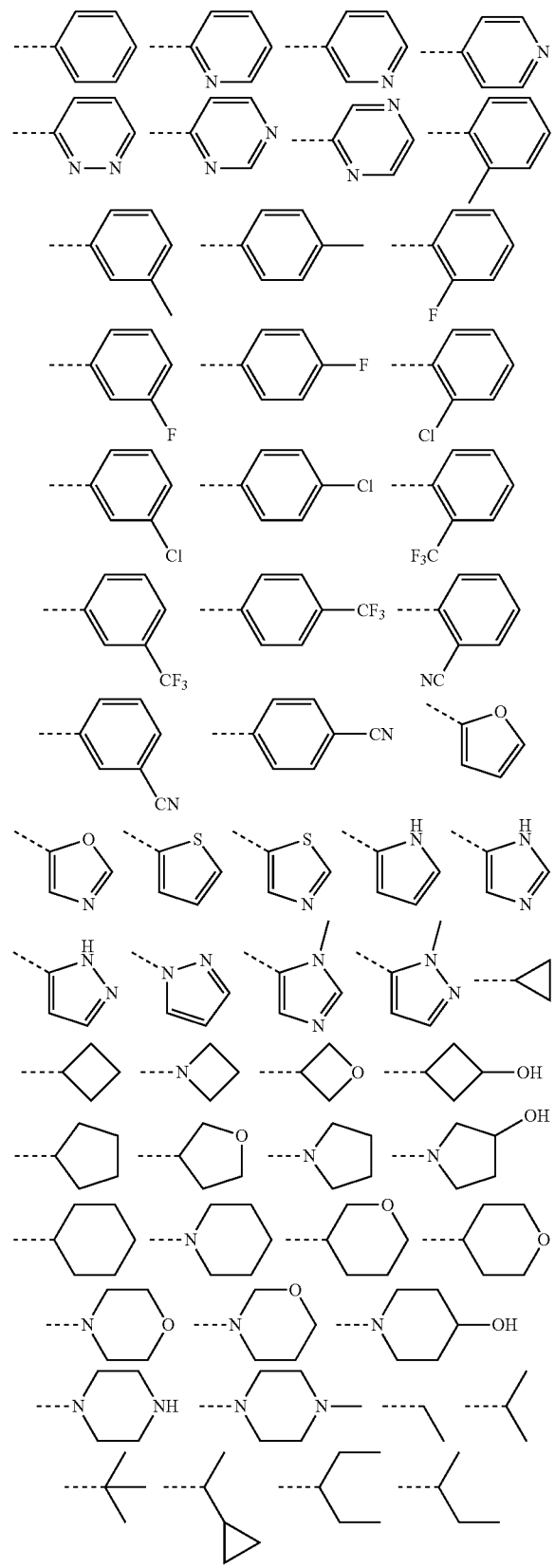
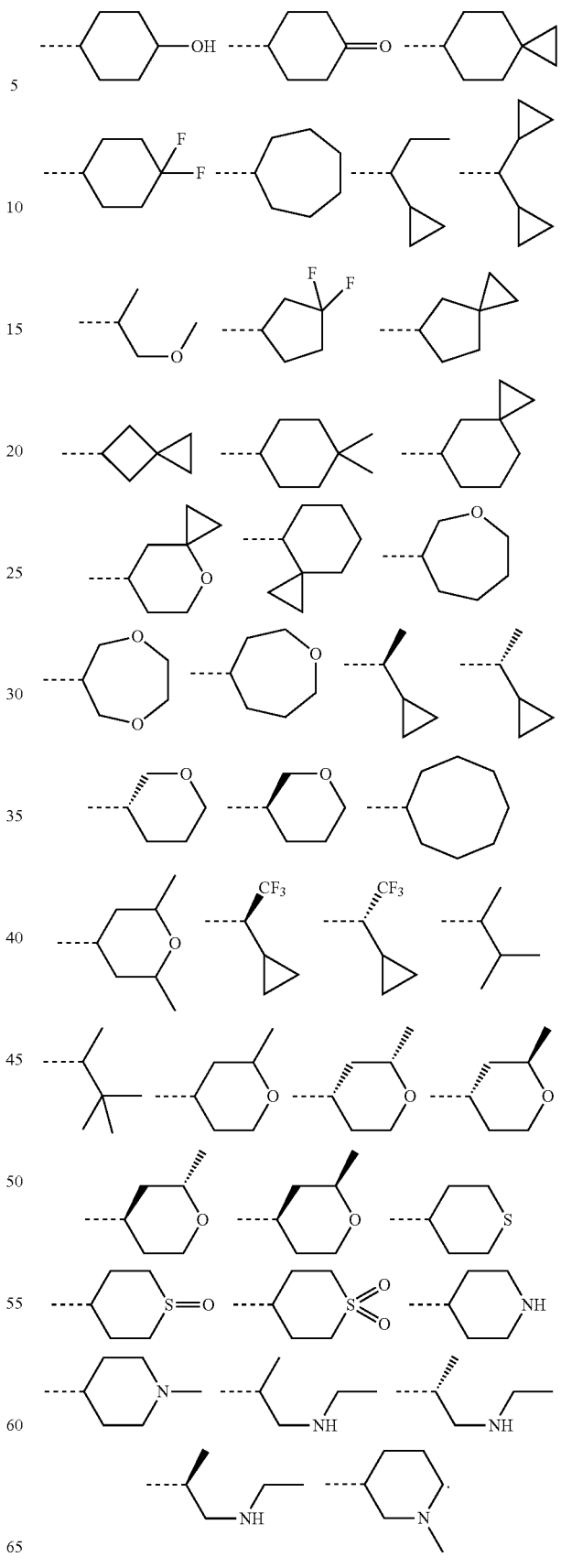

In some embodiments of aspects provided herein, $R_8$ is selected from the group consisting of:

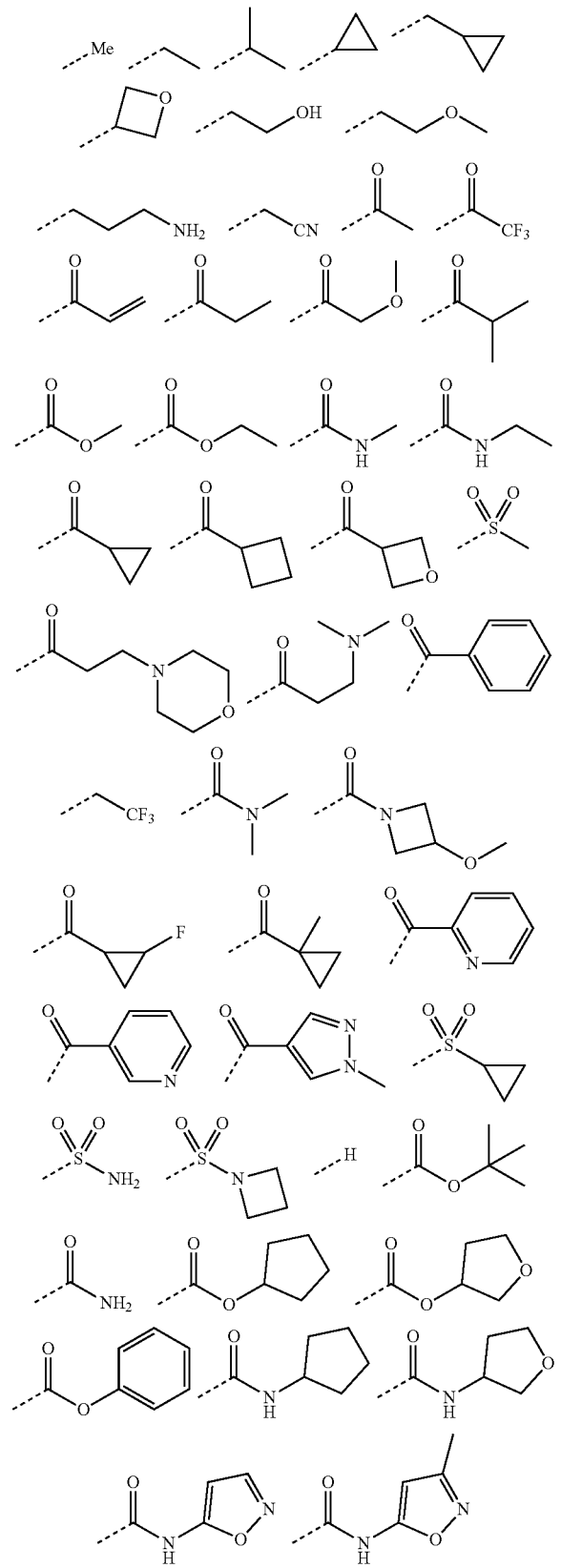

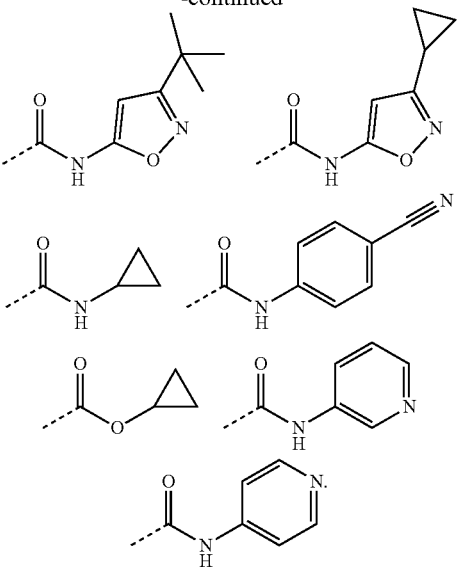

In some embodiments of aspects provided herein, for Formula (I), at least one of $A_1$, $A_2$ and $A_3$ is N. In some embodiments of aspects provided herein, $A_1$ is N. In some embodiments of aspects provided herein, $A_2$ and $A_3$ are CH. In some embodiments of aspects provided herein, $G_1$ and $G_2$ are C, $V_1$ is S, W is $CNR_7R_8$, and $V_2$ is N. In some embodiments of aspects provided herein, $A_2$ and $A_3$ are CH, $G_1$ and $G_2$ are C; $V_1$ is S, W is $CNR_7R_8$, and $V_2$ is N.

In some embodiments of aspects provided herein, for Formula (I)

L is O, $CH_2$ or NH; and $R_1$ is selected from the group consisting of:

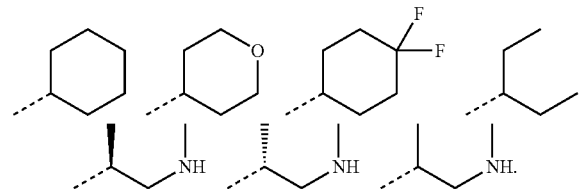

In some embodiments of aspects provided herein, at least one of $A_1$, $A_2$ and $A_3$ is N. In some embodiments of aspects provided herein, $A_1$ is N. In some embodiments of aspects provided herein, $A_2$ and $A_3$ are CH. In some embodiments of aspects provided herein, $G_1$ and $G_2$ are C, $V_1$ is S, W is $CNR_7R_8$, and $V_2$ is N. In some embodiments of aspects provided herein, $A_2$ and $A_3$ are CH, $G_1$ and $G_2$ are C; $V_1$ is S, W is $CNR_7R_8$, and $V_2$ is N.

The term "isomer" as used herein generally refers to and includes stereoisomer, cis/trans-isomer, tautomer, and isotopomers or isotopic isomers. Isotopes include $^2H$, $^3H$, $^{11}C$, $^{13}C$, $^{14}C$, $^{15}N$, $^{17}O$, $^{18}O$, $^{18}F$, $^{32}P$, $^{35}S$, $^{36}Cl$, etc.

Another aspect of the present disclosure provides a composition comprising a therapeutically effective amount of a compound of Formula (I) or any compound disclosed herein, or a stereoisomer, hydrate, ester, solvate, co-crystal, metabolite, stereoisomer or tautomer, or pharmaceutically acceptable salt thereof, and at least one component selected from the list of pharmaceutically acceptable carrier, diluent, adjuvant and excipient.

Still another aspect of the present disclosure provides a method for treating or preventing a necrosis-related disorder in a mammal suffering therefrom, the method comprising administering to the mammal a therapeutically effective amount of at least one compound of Formula (I) or any compound disclosed herein, or a stereoisomer, hydrate, ester, solvate, co-crystal, metabolite, stereoisomer or tautomer, or pharmaceutically acceptable salt thereof, or the pharmaceutical composition thereof, wherein the necrosis-related disorder is systematic inflammatory response, tumor, cancer, metabolic diseases or neurodegenerative diseases.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
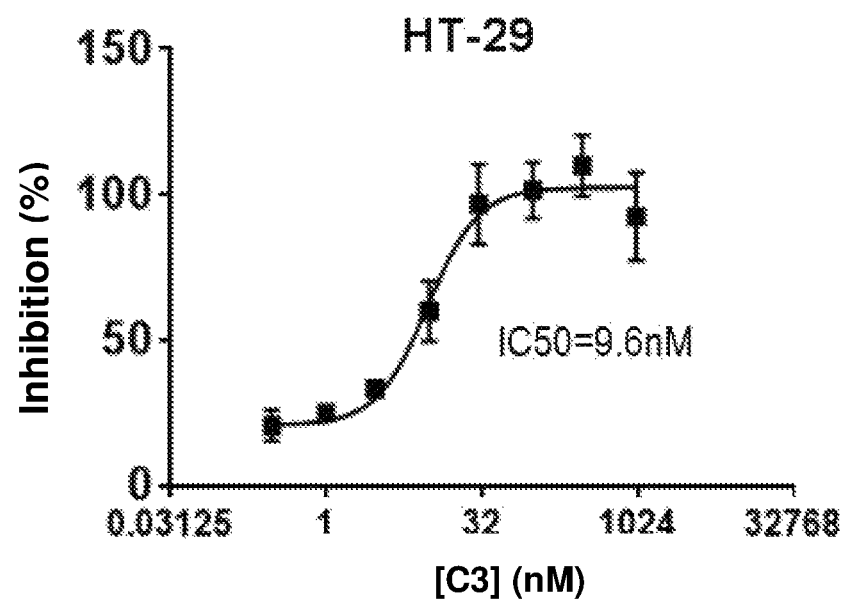
FIG. 1 depicts the inhibition of TNF-α induced-necrosis in HT29 cells by compound C3 in Example 42.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present disclosure unless otherwise specified. Where a compound exists in various tautomeric forms, a recited compound is not limited to any one specific tautomer, but rather is intended to encompass all tautomeric forms.

The term "alkyl" as used herein generally refers to a straight or branched chain saturated aliphatic hydrocarbon. Alkyl groups include groups having from 1 to 8 carbon atoms ($C_1$-$C_8$ alkyl), from 1 to 6 carbon atoms ($C_1$-$C_6$ alkyl) and from 1 to 4 carbon atoms ($C_1$-$C_4$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

The term "alkenyl" as used herein generally refers to straight or branched chain alkene groups, which comprise at least one unsaturated carbon-carbon double bond. Alkenyl groups include $C_2$-$C_8$ alkenyl, $C_2$-$C_6$ alkenyl and $C_2$-$C_4$ alkenyl groups, which have from 2 to 8, 2 to 6 or 2 to 4 carbon atoms, respectively, including, for example, ethenyl, allyl or isopropenyl. The term "alkynyl" as used herein generally refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively.

The term "cycloalkyl" as used herein generally refers to a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. For example, certain cycloalkyl groups are $C_3$-$C_7$ cycloalkyl, in which the cycloalkyl group contains a single ring having from 3 to 7 ring members, all of which are carbon. The term "cycloalkenyl" as used herein generally refers to a group that comprises one or more unsaturated rings in which all ring members are carbon.

The term "alkoxy" as used herein generally refers to an alkyl group as described above attached via an oxygen bridge. Alkoxy groups include $C_1$-$C_6$ alkoxy and $C_1$-$C_4$ alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "alkylamino" as used herein generally refers to a secondary or tertiary amine that has the general structure —NH—R1 or —N(R1)(R2), wherein R1 and R2 are selected independently from alkyl, cycloalkyl and (cycloalkyl)alkyl groups. Such groups include, but are not limited to, for example, mono- and di-($C_1$-$C_6$ alkyl)amino groups, in which each $C_1$-$C_6$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

The term "alkylthio" as used herein generally refers to an alkyl-substituted thio group, wherein the term alkyl is as defined above.

The term "halogen" or "halide" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term "heteroaryl" as used herein generally refers to an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" as used herein generally refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

The terms "substituent" and "substituted," as used herein, generally denote that a molecular moiety is covalently bonded to an atom within a molecule of interest, such as, for example, replacing a hydrogen atom with a non-hydrogen atom or group. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. A straight chain substituent may be a moiety such as a halogen, alkyl group, haloalkyl group or other group that is covalently bonded to an atom (preferably a carbon or nitrogen atom) that is a member of a straight chain.

The term "bicycloheteroalkyl" as used herein generally refers to a double ring structure which shares one or two atoms and which comprise at least one hetero atom independently selected from the group consisting of N, O, and S in the ring. The term "bicycloheteroalkylene" as used herein generally refers to a di-radical of bicycloheteroalkyl group, which may bind to two other groups.

The term "cycloalkylamine" as used herein generally refers to either a ring structure with an amino group attached to a carbon atom in the ring or a ring structure with a nitrogen atom as member of the ring.

The term "cycloalkylamide" as used herein generally refers to either a ring structure with an amid group attached to a carbon atom in the ring via the amide carbon or a ring structure with both the amide nitrogen and amide carbon atoms becoming members of the ring.

The term "cyclourea" as used herein generally refers to a ring structure with the urea carbon and both urea nitrogen atoms becoming members of the ring. One example of cyclourea is oxoimidazolidine.

Compounds disclosed herein are also meant to encompass all pharmaceutically acceptable compounds of Formula (I) being isotopically-labelled by having one or more atoms replaced by an atom having a different atomic mass or mass number. Examples of isotopes that can be incorporated into the disclosed compounds include, but are not limited to, isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{36}$Cl, $^{123}$I, and $^{125}$I, respectively.

Compounds disclosed herein are also meant to encompass the in vivo metabolic products of the disclosed compounds. Such products may result from, for example, the oxidation, reduction, hydrolysis, amidation, esterification, and other biochemical conversions of the administered compound, primarily due to enzymatic processes. Therefore, compounds disclosed include compounds produced by a process comprising administering a compound disclosed to a mammal for a period of time sufficient to yield a metabolic product thereof. The metabolic products can be identified by administering a radiolabeled compound of the present disclosure in a detectable dose to an animal, such as rat, mouse, guinea pig, monkey, or to a human, allowing sufficient time for the metabolic reaction(s) to occur, and isolating the metabolic products from the urine, blood or other biological samples.

The term "pharmaceutically acceptable" as used herein generally refers to a form of the compound that is safe for administration to a subject. For example, a free base, a salt form, a solvate, a hydrate, a prodrug or derivative form of a compound of Formula (I), which has been approved for mammalian use, via oral ingestion or any other route of administration, by a governing authority or regulatory agency, such as the Food and Drug Administration (FDA) of the United States, is pharmaceutically acceptable.

Included in the compounds of Formula (I) are the pharmaceutically acceptable salt forms of the free-base compounds. The term "pharmaceutically-acceptable salts" as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

The term "solvate" as used herein generally refers to an aggregate that comprises one or more molecules of a compound of the present disclosure with one or more molecules of solvent. The solvent may be water, in which case the solvate may be a "hydrate". Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the present disclosure may be true solvates, while in other cases, the compound of the present disclosure may merely retain adventitious water or be a mixture of water plus some adventitious solvent.

In some embodiments, the compound(s) of Formula (I) is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes.

The term "diluent" as used herein generally refers to an agent used as filler in order to achieve the desired composition volume or weight. The diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

The term "adjuvant," as used herein generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present disclosure, which may be used in a suitable hydrated form, and/or the pharmaceutical compositions of the present disclosure, are formulated into pharmaceutically acceptable dosage forms or by other conventional methods known to those of skill in the art.

Actual dosage levels of the active ingredients in the pharmaceutical compositions of the present disclosure may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present disclosure employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of Formula (I), or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of Formula (I) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formula (I), which inhibits necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present disclosure can be prepared using various synthetic routes, including those described below, starting from commercially available materials. Starting materials of the disclosure, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially unless stated otherwise. All commercial reagents and solvent were used without purification unless stated otherwise. When required, some reagents and solvents were purified by standard techniques. For example, tetrahydrofuran may be purified by distillation from sodium. Other solvents may be distilled before use. Anhydrous solvent may be treated according to standard procedures or methods disclosed in references. Unless stated otherwise, all thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All organic layers after extraction were dried over anhydrous $Na_2SO_4$ unless stated otherwise. All nuclear magnetic resonance spectra were recorded using a Bruck-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an Agela Durashell C18 3.5 μm 4.6×50 mm column. Gradients were run using 0.1% $NH_4HCO_3$ aqueous solution and acetonitrile with gradient 5/95 to 95/5 in the run time indicated (for example, 5 min), flow rate at 1.8 mL/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

EXAMPLES

Example 1: Compound C1

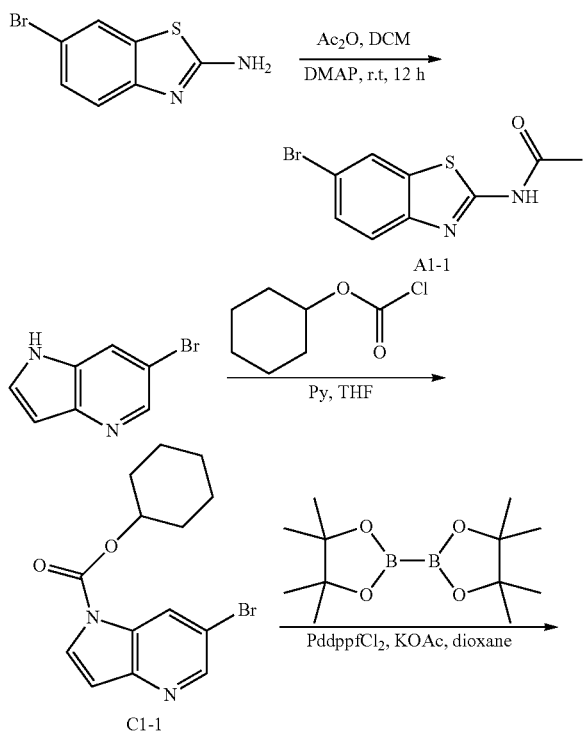

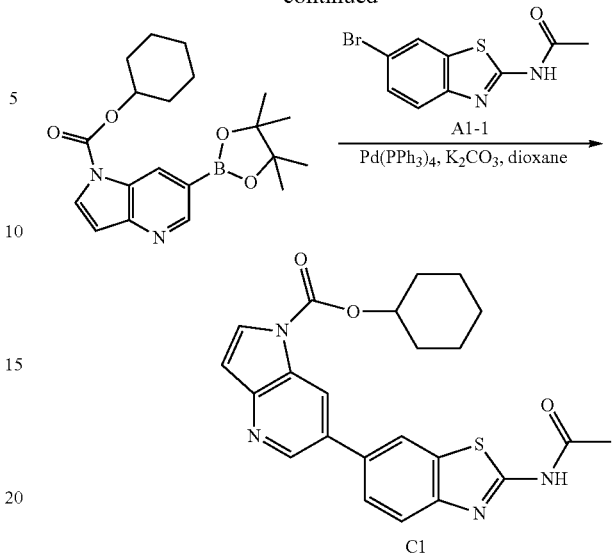

Step 1: N-(6-bromo-1,3-benzothiazol-2-yl)acetamide (A1-1)

To a solution of 6-bromo-1,3-benzothiazol-2-amine (2.50 g, 10.7 mmol) and DMAP (1.33 g, 12.8 mmol) in $CH_2Cl_2$ (20 mL) was added slowly acetic anhydride (1.23 mL, 13.0 mmol) at 0° C. The mixture was stirred at room temperature overnight. Then the mixture was poured into 1N HCl solution, and the solids were collected via suction filtration. The solids were washed with water, dried to provide the title compound as a white solid (2.30 g, 79%). $^1$H NMR (400 MHz, $CDCl_3$) δ 9.90 (br s, 1H), 7.94 (s, 1H), 7.61 (d, J=10.4 Hz, 1H), 7.54 (d, J=10.4 Hz, 1H), 2.30 (s, 3H).

Step 2: 7-bromo-1H-pyrido[2,3-b][1,4]oxazin-2 (3H)-one (C1-1)

To a solution of 6-bromo-1H-pyrrolo[3,2-b]pyridine (97 mg, 0.5 mmol) in anhydrous THF (5 mL) was added slowly pyridine (120 mg, 1.5 mmol) followed by cyclohexyl carbonochloridate (162 mg, 1 mmol) in THF (2 mL). The mixture was stirred at room temperature for 3 h. The reaction was quenched by the addition of saturated NaCl solution (20 mL). The aqueous phase was extracted with EtOAc (3×) and the combined organic layers were combined, dried and concentrated. The residue was purified by silica gel column chromatography (petroleum ether/ethyl acetate=5/1) to give the title compound as a colorless oily liquid (120 mg, 75%). $^1$H NMR (400 MHz, DMSO-$d_6$) δ 8.58 (s, 2H), 7.84 (d, J=2.4 Hz, 1H), 8.77 (d, J=3.6 Hz, 1H), 5.13-5.00 (m, 1H), 2.13-1.97 (m, 2H), 1.91-1.75 (m, 2H), 1.72-1.33 (m, 6H).

Step 3: cyclohexyl 6-(2-acetamido-1,3-benzothiazol-6-yl)pyrrolo[3,2-b]pyridine-1-carboxylate (C1)

Add sequentially C1-1 (112 mg, 0.35 mmol), 4,4,5,5-tetramethyl-2-(4,4,5,5-tetramethyl-1,3,2-dioxaborolan-2-yl)-1,3,2-dioxaborolane (132 mg, 0.52 mmol), potassium acetate (86 mg, 0.88 mmol), [1,1'-bis(diphenylphosphino)ferrocene]dichloropalladium(II) (Pd(dppf)$Cl_2$) (26 mg, 0.035 mmol) to 1,4-dioxane (15 mL) under $N_2$. The mixture was stirred at 100° C. for 5 h. Cooled to room temperature and filtered. To the filtrate were sequentially added A1-1 (68 mg, 0.25 mmol), K₂CO₃ (87 mg, 0.63 mmol), Pd(PPh₃)₄ (29 mg, 0.025 mmol), and H₂O (1 mL) under N₂. The mixture was stirred at 80° C. under N₂ overnight. The mixture was cooled to room temperature, filtered, and the filtrate concentrated. The residue was purified by silica gel column chromatography (dichloromethane/methanol=50:1) to provide a white solid, which was triturated in EtOAc/ether (v/v=1:2, 15 mL) to give the title compound as a white solid (20 mg, 19%). Its analytic data are shown in Table 1.

Example 2: Compound C2

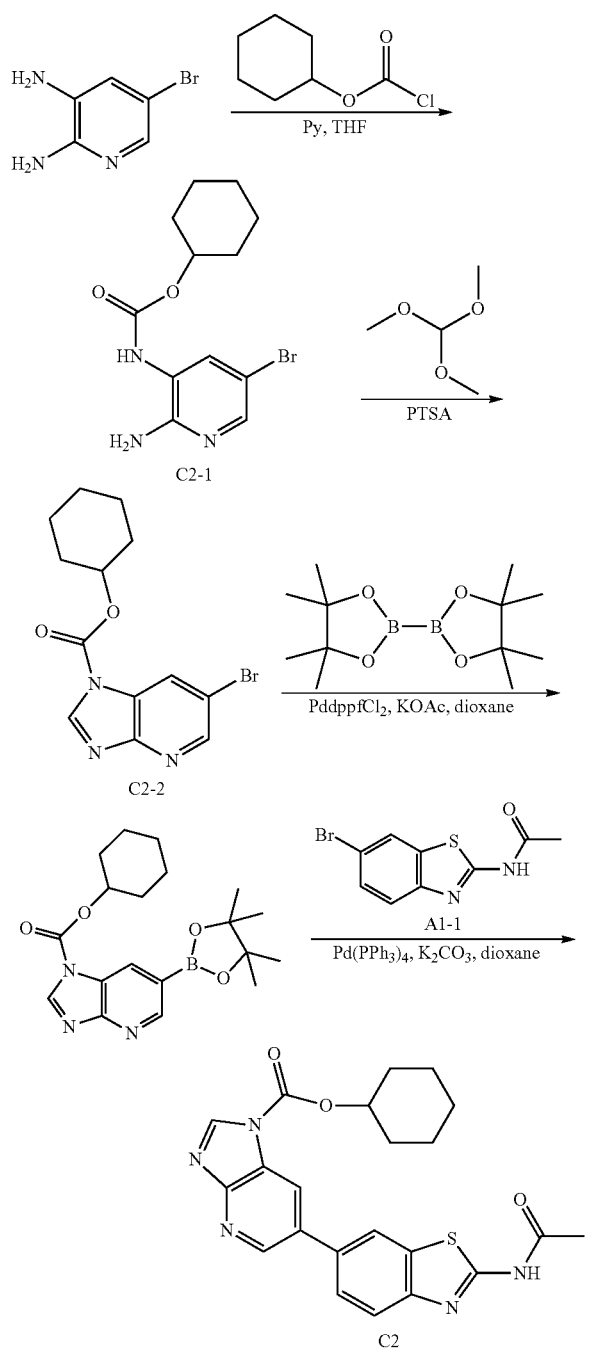

Step 1: cyclohexyl N-(2-amino-5-bromo-3-pyridyl) carbamate (C2-1)

To a solution of 5-bromopyridine-2,3-diamine (187 mg, 1.0 mmol) in anhydrous THF (5 mL) was added pyridine (160 mg, 2.0 mmol) at 0° C., followed by the addition of a solution of cyclohexyl carbonochloridate (162 mg, 1.0 mmol) in THF (2 mL). The mixture was stirred at room temperature for 3 h, and quenched with a saturated NaCl solution (20 mL). The aqueous layer was extracted with EtOAc (20 mL×3). Combined organic layers was dried and concentrated. The residue was purified by silica gel column chromatography (petroleum ether/ethyl acetate=10/1) to give the title compound as a colorless oily liquid (50 mg, 16%). ¹H NMR (400 MHz, CDCl₃) δ 7.98 (s, 1H), 7.81 (br s, 1H), 6.19 (br s, 1H), 4.81-4.69 (m, 1H), 4.52 (br s, 2H), 1.99-1.85 (m, 2H), 1.82-1.68 (m, 2H), 1.50-1.20 (m, 6H).

Step 2: cyclohexyl 6-bromoimidazo[4,5-b]pyridine-1-carboxylate (C2-2)

To a solution of C2-1 (47 mg, 0.15 mmol) in trimethoxymethane (3 mL) was added catalytic amount of p-toluenesulfonic acid (4 mg, 0.015 mmol). The mixture was stirred at 90° C. overnight, then cooled to room temperature and concentrated. The residue was dissolved in EtOAc (20 mL) and washed with aqueous saturated NaHCO₃ solution (15 mL×2). The organic layer was separated, dried and concentrated to give the title compound as a while solid (40 mg, 83%). ¹H NMR (400 MHz, CDCl₃) δ 8.62 (s, 1H), 7.99 (s, 1H), 7.63 (s, 1H), 4.77 (s, 1H), 2.05-1.90 (m, 2H), 1.86-1.78 (m, 2H), 1.56-1.21 (m, 6H).

Step 3: cyclohexyl 6-(2-acetamido-1,3-benzothiazol-6-yl)imidazo[4,5-b]pyridine-1-carboxylate (C2)

To 1,4-dioxane (10 mL) under N₂ were added sequentially C2-2 (45 mg, 0.14 mmol), 4,4,5,5-tetramethyl-2-(4,4,5,5-tetramethyl-1,3,2-dioxaborolan-2-yl)-1,3,2-dioxaborolane (53 mg, 0.014 mmol), potassium acetate (34 mg, 0.35 mmol), and Pd(dppf)Cl₂ (10 mg, 0.014 mmol). The mixture was stirred at 100° C. for 5 h. Cooled to room temperature and filtered. To the filtrate were sequentially added A1-1 (27 mg, 0.1 mmol), K₂CO₃ (35 mg, 0.25 mmol), Pd(PPh₃)₄ (12 mg, 0.010 mmol), and H₂O (1 mL) under N₂. The mixture was stirred at 80° C. under N₂ overnight. The mixture was cooled to room temperature, filtered, and the filtrate was concentrated. The residue was purified by silica gel column chromatography (dichloromethane/methanol=70:1) to provide a white solid, which was triturated in EtOAc/ether (v/v=1:2, 10 mL) to give the title compound as a white solid (10 mg, 23%). Its analytic data are shown in Table 1.

Example 3: Compound C3

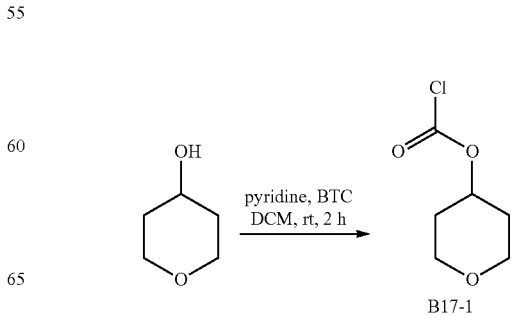

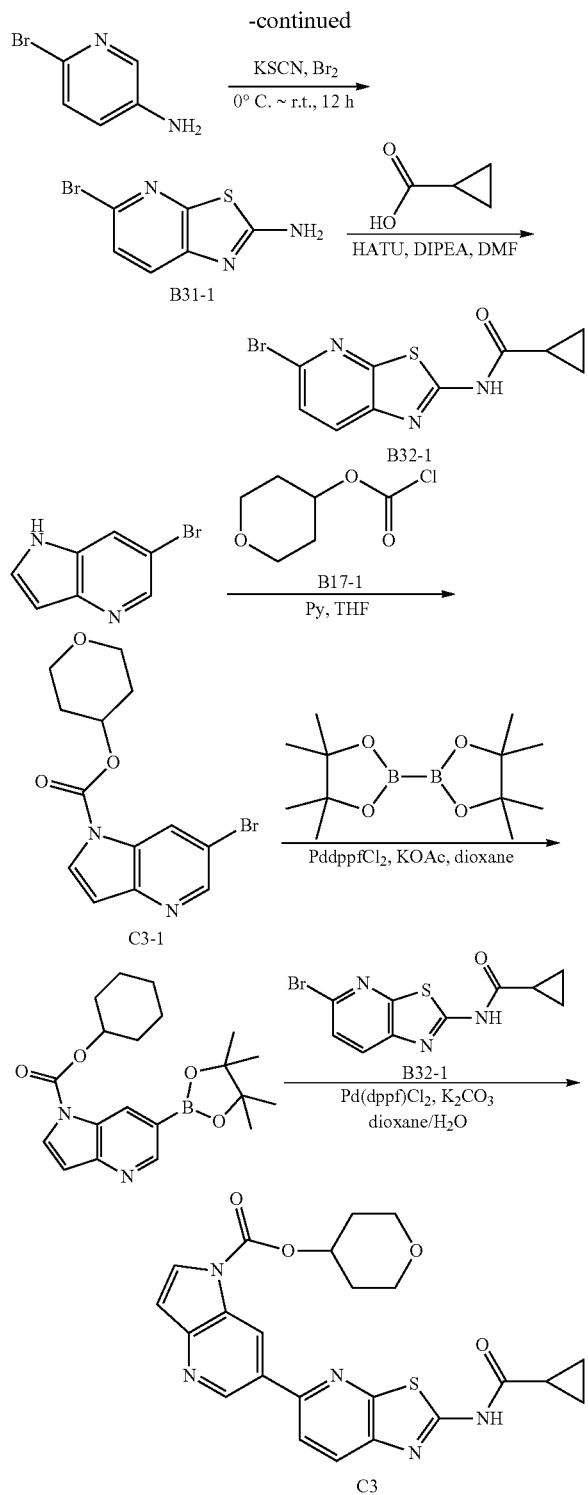

stirred at room temperature for 2 h, and the mixture was filtered. The filtrate was concentrated to give the title compound as a colorless oil (5 g, 90%).

Step 2: Intermediate 5-bromothiazolo[5,4-b]pyridin-2-amine (B31-1)

To a solution of KSCN (970 mg, 10.0 mmol) in acetic acid (2 mL) was added dropwise 6-bromopyridin-3-amine (348 mg, 2.0 mmol) at 0° C. and stirred for 5 min. A solution of Br$_2$ (420 mL, 2.6 mmol) in acetic acid (1 mL) was added to the mixture at 0° C. The resulting mixture was stirred at room temperature overnight, filtered, and concentrated. The residue was neutralized with NaHCO$_3$ solution and the aqueous layer was extracted with CH$_2$Cl$_2$. Combined organic layers were combined, dried and concentrated. The residue was purified by silica gel column chromatography (dichloromethane/methanol=100:1) to give the title compound as a white solid (190 mg, 41%). $^1$H NMR (400 MHz, DMSO-d6) δ 7.95 (s, 2H), 7.56 (d, J=8.4 Hz, 1H), 7.42 (d, J=8.4 Hz, 1H).

Step 3, intermediate N-(5-bromothiazolo[5,4-b]pyridin-2-yl)cyclopropanecarboxamide (B32-1)

To a solution of cyclopropanecarboxylic acid (215 mg, 2.5 mmol) in DMF (10 mL) was added sequentially N,N-diisopropylethylamine (DIPEA, 645 mg, 5 mmol) and 1-[bis(dimethylamino)methylene]-1H-1,2,3-triazolo[4,5-b]pyridinium 3-oxide hexafluorophosphate (HATU, 950 mg, 2.5 mmol) and the mixture was stirred for 15 min at room temperature. B31-1 (229 mg, 1 mmol) was added to the mixture and the resulting mixture was stirred at 90° C. for 48 h. The mixture was cooled to room temperature and poured into water (50 mL). Brown solids crushed out of the mixture was filtered and purified by silica gel column chromatography (petroleum ether/ethyl acetate=10/1) to give the title compound as a red solid (190 mg, 64%). $^1$H NMR (400 MHz, DMSO-d6) δ 12.90 (s, 1H), 8.05 (d, J=8.4 Hz, 1H), 7.67 (d, J=8.0 Hz, 1H), 2.06-1.95 (m, 1H), 1.07-0.90 (m, 4H).

Step 4: Intermediate tetrahydropyran-4-yl 6-bromopyrrolo[3,2-b]pyridine-1-carboxylate (C3-1)

To a solution of 6-bromo-1H-pyrrolo[3,2-b]pyridine (825 mg, 4.2 mmol) in anhydrous THF (50 mL) was added pyridine (1.0 g, 12.6 mmol) and B17-1 (1.4 g, 8.4 mmol) in THF (50 mL). The mixture was stirred room temperature for 3 h and quenched with saturated brine (50 mL). The aqueous layer was extracted with EtOAc (50 mL×3). The organic layers were collected, dried, filtered and concentrated. The residue was purified by silica gel column chromatography (petroleum ether/ethyl acetate=5/1) to give the title compound as a colorless oil (1.1 g, 81%). $^1$H NMR (400 MHz, DMSO-d6) δ 8.60 (s, 1H), 8.47 (s, 1H), 8.09 (d, J=2.4 Hz, 1H), 8.89 (s, 1H), 5.25-5.15 (m, 1H), 3.98-3.81 (m, 2H), 3.56 (t, J=8.8 Hz, 2H), 2.14-1.98 (m, 2H), 1.91-1.64 (m, 2H).

Step 5: tetrahydropyran-4-yl 6-[2-(cyclopropanecarbonylamino)thiazolo[5,4-b]pyridin-5-yl]pyrrolo[3,2-b]pyridine-1-carboxylate (C3)

To 1,4-dioxane (10 mL) under N$_2$ were added sequentially C3-1 (91 mg, 0.28 mmol), 4,4,5,5-tetramethyl-2-(4,4,5,5-tetramethyl-1,3,2-dioxaborolan-2-yl)-1,3,2-dioxaborolane Step 1: Intermediate tetrahydropyran-4-yl carbonochloridate (B17-1)

To a solution of tetrahydropyran-4-ol (3.54 g, 24.7 mmol) and pyridine (2.74 mL) in CH$_2$Cl$_2$ (50 mL) was added slowly triphosgene (BTC) (4.04 g, 34.7 mmol) at room temperature. The mixture was stirred for 3 h and concentrated. EtOAc (100 mL) was added to the resulting residue, (137 mg, 0.54 mmol), potassium acetate (55 mg, 0.58 mmol), Pd(dppf)Cl$_2$ (21 mg, 0.028 mmol). The mixture was stirred at 100° C. for 5 h. Cooled to room temperature and filtered. To the filtrate were sequentially added B32-1 (60 mg, 0.2 mmol), K$_2$CO$_3$ (70 mg, 0.5 mmol), Pd(dppf)Cl$_2$ (15 mg, 0.023 mmol), and H$_2$O (1 mL) under N$_2$. The mixture was stirred at 100° C. under N$_2$ overnight. The mixture was cooled to room temperature, filtered, and the filtrate was concentrated. The residue was purified by silica gel column chromatography (dichloromethane/methanol=75:1) to provide a white solid, which was triturated in EtOAc/ether (v/v=1:2, 15 mL) to give the title compound as a white solid (35 mg, 35%). Its analytic data are shown in Table 1.

Example 4: Compound C4

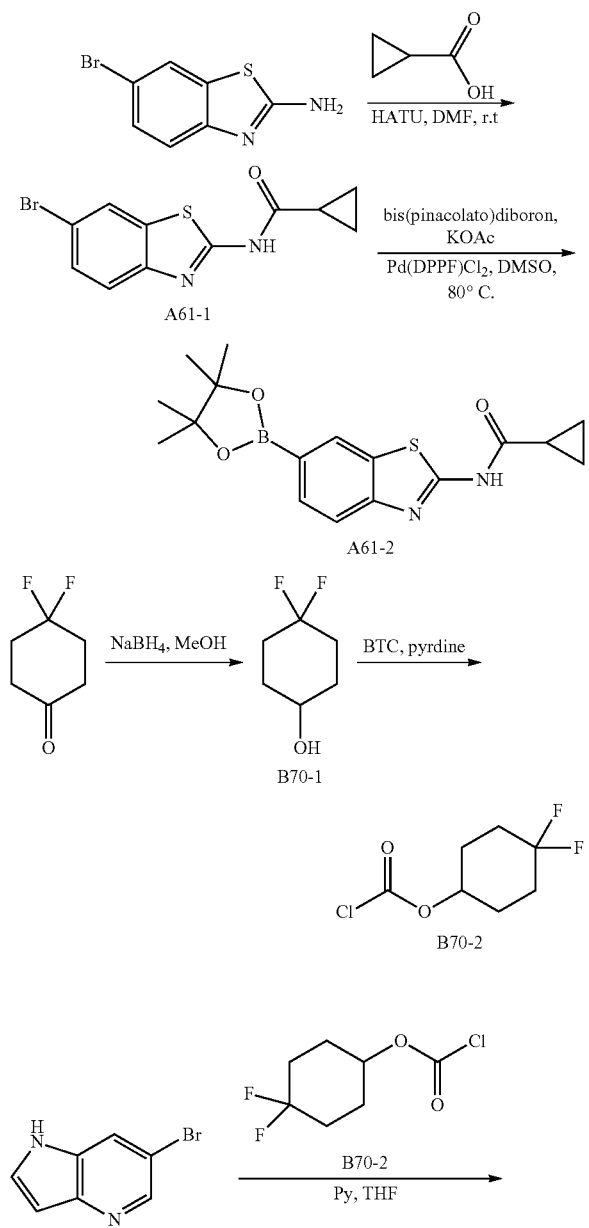

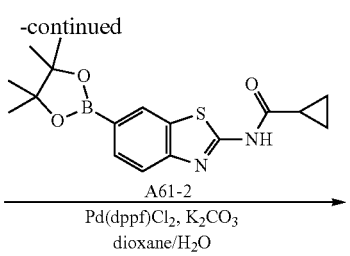

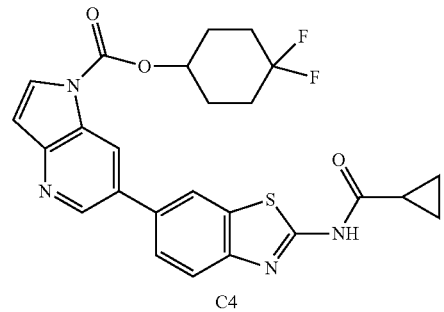

Step 1: Intermediate N-(6-bromo-1,3-benzothiazol-2-yl)cyclopropanecarboxamide (A61-1)

To a solution of cyclopropanecarboxylic acid (380 mg, 4.4 mmol) in DMF (3 mL) was added HATU (1.8 g, 4.4 mmol) and the mixture was stirred at room temperature for 15 minutes. 6-Bromo-1,3-benzothiazol-2-amine (500 mg, 2.2 mmol) and DIPEA (850 mg, 6.6 mmol) were added to the mixture and the resulting mixture was stirred for 5 h. The mixture was poured into water (20 mL), and solids crushed out of the mixture was filtered to give the title compound as a white solid (190 mg, 64%). $^1$H NMR (400 MHz, CDCl$_3$) δ 12.72 (s, 1H), 8.23 (s, 1H), 7.66 (d, J=8.5 Hz, 1H), 7.56 (d, J=8.5 Hz, 1H), 2.00 (s, 1H), 0.97 (d, J=7.5 Hz, 4H).

Step 2: Intermediate N-[6-(4,4,5,5-tetramethyl-1,3,2-dioxaborolan-2-yl)-1,3-benzothiazol-2-yl]cyclopropanecarboxamide (A61-2)

To a solution of A61-1 (480 mg, 1.7 mmol) and 4,4,5,5-tetramethyl-2-(4,4,5,5-tetramethyl-1,3,2-dioxaborolan-2-yl)-1,3,2-dioxaborolane (530 mg, 2.1 mmol) in DMSO (5 mL) were added potassium acetate (380 mg, 4 mmol), Pd(dppf)Cl$_2$ (120 mg, 0.16 mmol) under N$_2$. The mixture was stirred at 80° C. overnight. The mixture was filtered. The filtrate was diluted with EtOAc (20 mL) and the resulting mixture was washed with brine (5 mL×6). The organic layer was purified by silica gel column chromatography (dichloromethane/methanol=100:1.2) to give the title compound as a lightly red solid (380 mg, 69%). $^1$H NMR (400 MHz, DMSO-d6) δ 12.73 (s, 1H), 8.25 (s, 1H), 7.71 (s, 2H), 2.01 (s, 1H), 1.31 (s, 12H), 1.16 (s, 8H), 0.95 (s, 4H).

Step 3: Intermediate 4,4-difluorocyclohexanol (B70-1)

To a solution of 4,4-difluorocyclohexanone (5 g, 37.3 mmol) in MeOH (30 mL) was added NaBH$_4$ (4.2 g, 112 mmol) in portions, and the mixture was stirred at room temperature for 1 h. Quenched with water and concentrated to remove MeOH. The aqueous layer was extracted with CH$_2$Cl$_2$. The combined organic layers were dried, filtered, and the filtrate was concentrated to provide the title compound as a brown oil (4.7 g, 94%). $^1$H NMR (400 MHz, CDCl$_3$) δ 3.92 (s, 1H), 2.20-2.00 (m, 2H), 1.94-1.79 (m, 4H), 1.78-1.68 (m, 2H).

Step 4: Intermediate (4,4-difluorocyclohexyl)carbonochloridate (B70-2)

To a solution of triphosgene (BTC) (870 g, 2.9 mmol) in CH$_2$Cl$_2$ (20 mL) at 0° C. was added dropwise pyridine (634 mg, 8.0 mmol) and stirred at 0° C. for 10 min. A solution of B70-1 (1 g, 7.3 mmol) in CH$_2$Cl$_2$ (10 mL) was added dropwise to the resulting mixture. The mixture was stirred for 4 h at room temperature and concentrated. EtOAc was added to the resulting residue and filtered to remove solids. The filtrate was concentrated to give the title compound as a light yellow crude oil (1.5 g).

Step 5: Intermediate (4,4-difluorocyclohexyl) 6-bromopyrrolo[3,2-b]pyridine-1-carboxylate (C4-1)

To a solution of 6-bromo-1H-pyrrolo[3,2-b]pyridine (97 mg, 0.5 mmol) in anhydrous THF (8 mL) was added pyridine (120 mg, 1.5 mmol) at room temperature, followed by the addition of a solution of B70-2 (198 mg, 1 mmol) in THF (2 mL). The mixture was stirred at room temperature for 3 h and quenched with saturated brine (20 mL). The aqueous layer was extracted with EtOAc (20 mL×3). The organic layers were collected, dried, filtered and concentrated. The residue was purified by silica gel column chromatography (petroleum ether/ethyl acetate=20/1) to give the title compound as a colorless oil (71 mg, 40%). $^1$H NMR (400 MHz, DMSO-d$_6$) δ 8.62 (s, 1H), 8.49 (s, 1H), 8.17 (s, 1H), 8.89 (s, 1H), 5.21 (s, 1H), 2.17-1.92 (m, 8H).

Step 6: (4,4-difluorocyclohexyl) 6-[2-(cyclopropanecarbonylamino)-1,3-benzothiazol-6-yl]pyrrolo[3,2-b]pyridine-1-carboxylate (C4)

To 1,4-dioxane/H$_2$O (10 mL/0.5 mL) under N$_2$ were added sequentially C4-1 (71 mg, 0.2 mmol), A61-2 (103 mg, 0.3 mmol), K$_2$CO$_3$ (70 mg, 0.5 mmol), Pd(dppf)Cl$_2$ (15 mg, 0.02 mmol). The mixture was stirred at 100° C. under N$_2$ overnight. The mixture was cooled to room temperature, filtered, and the filtrate was concentrated. The residue was purified by silica gel column chromatography (dichloromethane/methanol=50:1) to provide a white solid, which was triturated in EtOAc/ether (v/v=1:2, 15 mL) to give the title compound as a white solid (40 mg, 40%). Its analytic data are shown in Table 1.

Example 5: Compound C5

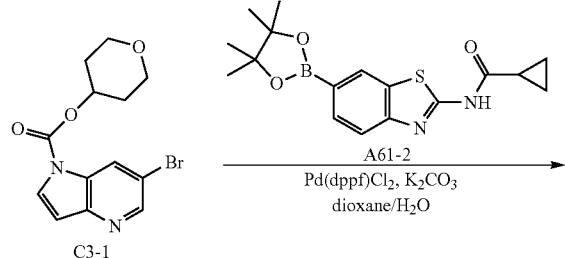

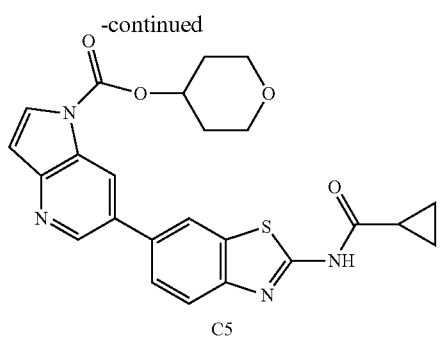

Step 1: tetrahydropyran-4-yl 6-[2-(cyclopropanecarbonylamino)-1,3-benzothiazol-6-yl]pyrrolo[3,2-b]pyridine-1-carboxylate (C5)

To 1,4-dioxane/H$_2$O (10 mL/0.5 mL) under N$_2$ were added sequentially C3-1 (64 mg, 0.2 mmol), A61-2 (103 mg, 0.3 mmol), K$_2$CO$_3$ (70 mg, 0.5 mmol), Pd(dppf)Cl$_2$ (15 mg, 0.02 mmol). The mixture was stirred at 100° C. under N$_2$ overnight. The mixture was cooled to room temperature, filtered, and the filtrate was concentrated. The residue was purified by silica gel column chromatography (dichloromethane/methanol=50:1) to provide a white solid, which was triturated in EtOAc/ether (v/v=1:2, 15 mL) to give the title compound as a white solid (45 mg, 49%). Its analytic data are shown in Table 1.

Example 6: Compound C6

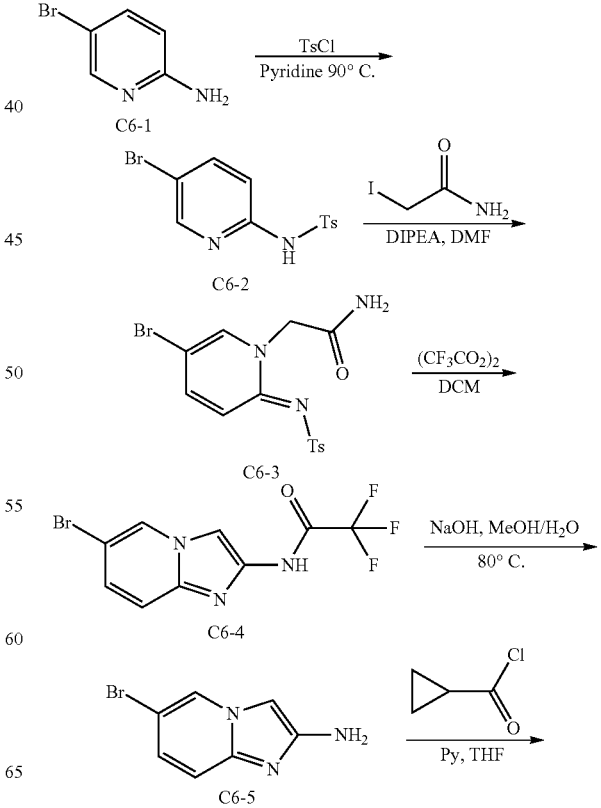

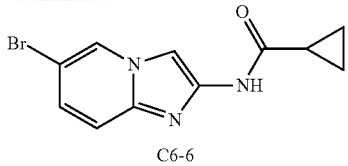

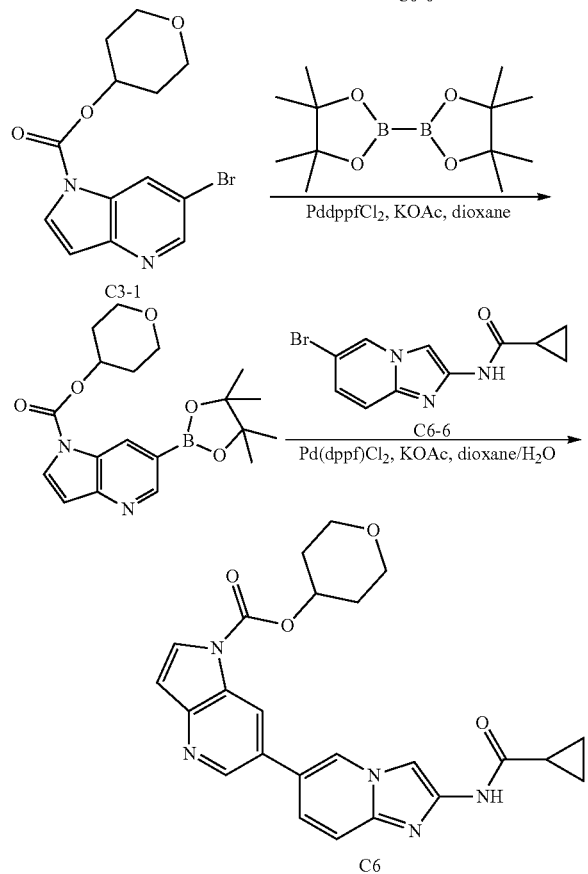

Step 1: Intermediate N-(5-bromo-2-pyridyl)-4-methyl-benzenesulfonamide (C6-2)

To a solution of 5-bromopyridin-2-amine (308 g, 1.72 mol) in pyridine (1.4 L) was added p-TsCl (366 g, 1.9 mol) in pyridine (300 mL). The mixture was stirred at 90° C. for 5 h, cooled to room temperature, and concentrated. Water (2.5 L) was added to the residue and the resulting mixture was stirred for 30 min. The mixture was filtered, and the filter cake was washed with water and dried to provide the title compound as a crude yellow solid (587 g). $^1$H NMR (400 MHz, DMSO-$d_6$) δ 11.24 (br s, 1H), 8.27 (s, 1H), 7.89 (d, J=8.0 Hz, 1H), 7.78 (d, J=8.0 Hz, 2H), 7.36 (d, J=7.36 Hz, 2H), 7.02 (d, J=8.8 Hz, 1H), 2.35 (s, 3H).

Step 2: Intermediate 2-[(2E)-5-bromo-2-(p-tolylsulfonylimino)-1-pyridyl]acetamide (C6-3)

To a solution of C6-2 (587 g, 1.8 mol) in DMF (1.8 L) was added sequentially 2-iodoacetamide (383 g, 2.07 mol) and DIPEA (287 g, 2.16 mol) at room temperature. The mixture was stirred overnight, then poured into water (20 L). The resulting mixture was mechanically stirred and filtered. The solids collected from the filtration was dried, then triturated with CH$_2$Cl$_2$ (4 L). Filtrate provides the title compound as a while solid (590 g, 90%).

Step 3: Intermediate N-(6-bromoimidazo[1,2-a]pyridin-2-yl)-2,2,2-trifluoro-acetamide (C6-4)

To a suspension of C6-3 (150 g) in CH$_2$Cl$_2$ (1.5 L) was added trifluoroacetic anhydride (164 g, 783 mmol) dropwise at 0° C. After the addition was complete, the mixture was warmed to room temperature and stirred for 2 h. After TLC indicated that the reaction was over, the mixture was poured into ice-water (3 L), and its pH was adjusted to 6-7 using a saturated aqueous NaHCO$_3$ solution. The solids were collected, dried, and triturated with CH$_2$Cl$_2$ (1 L 2) to provide the title compound as a white solid (120 g, 50%). $^1$H NMR (400 MHz, DMSO-$d_6$) δ 12.55 (br s, 1H), 8.96 (s, 1H), 8.24 (s, 1H), 7.51 (d, J=8.8 Hz, 1H), 7.41 (d, J=8.8 Hz, 1H).

Step 4: Intermediate 6-bromoimidazo[1,2-a]pyridin-2-amine (C6-4)

To a solution of C6-4 (110 g, 357 mmol) in MeOH (1 L) was added NaOH (17 g, 428 mmol in 420 mL) aqueous solution. Stirred at 80° C. overnight. After the reaction was complete according to thin-layer chromatography (TLC), the mixture was cooled to room temperature. Insoluble solids were filtered off, the resulting filtrate was concentrated, the resulting mixture was added to brine (1 L), and extracted with CH$_2$Cl$_2$ (800 mL×3). The organic layers were combined, dried, filtered, the filtrate was concentrated to provide the title compound as a yellow solid (75 g, 99%). $^1$H NMR (400 MHz, DMSO-$d_6$) δ 8.60 (s, 1H), 7.13 (d, J=9.2 Hz, 1H), 7.07 (d, J=8.0 Hz, 1H), 7.00 (s, 1H), 5.19 (br s, 2H).

Step 5: Intermediate N-(6-bromoimidazo[1,2-a]pyridin-2-yl)cyclopropanecarboxamide (C6-5)

To a solution of C6-5 (73 g, 346 mmol) in CH$_2$Cl$_2$ (1.5 L) was added Et$_3$N (42 g, 415 mmol). Cyclopropanecarbonyl chloride (41 g, 398 mmol) in CH$_2$Cl$_2$ (100 mL) was added dropwise at 0° C. After the addition was complete, the mixture was warmed to room temperature and stirred for 3 h. After the reaction was complete according to TLC, saturated K$_2$CO$_3$ solution (100 mL) was added to quench the reaction. The mixture was stirred for 2 h. Yellow solids crushed out of the mixture were collected by filtration, and dried to provide the title compound as a yellow solid (97 g, 99%). $^1$H NMR (400 MHz, DMSO-$d_6$) δ 11.03 (br s, 1H), 8.87 (s, 1H), 8.06 (s, 1H), 7.39 (d, J=9.2 Hz, 1H), 7.31 (d, J=9.6 Hz, 1H), 2.00-1.90 (m, 1H), 0.79 (d, J=7.6 Hz, 4H).

Step 6: tetrahydropyran-4-yl 6-[2-(cyclopropanecarbonylamino)imidazo-[1,2-a]pyridin-6-yl]pyrrolo[3,2-b]pyridine-1-carboxylate (C6)

To 1,4-dioxane (10 mL) under N$_2$ were added sequentially C3-1 (91 mg, 0.28 mmol), 4,4,5,5-tetramethyl-2-(4,4,5,5-tetramethyl-1,3,2-dioxaborolan-2-yl)-1,3,2-dioxaborolane (137 mg, 0.54 mmol), potassium acetate (55 mg, 0.58 mmol), Pd(dppf)Cl$_2$ (21 mg, 0.028 mmol). The mixture was stirred at 100° C. for 5 h. Cooled to room temperature and filtered. To the filtrate were sequentially added C6-6 (56 mg, 0.2 mmol), K$_2$CO$_3$ (70 mg, 0.5 mmol), Pd(dppf)Cl$_2$ (15 mg, 0.023 mmol), and H$_2$O (1 mL) under N$_2$. The mixture was stirred at 100° C. under N$_2$ overnight. The mixture was cooled to room temperature, filtered, and the filtrate was concentrated. The residue was purified by silica gel column chromatography (dichloromethane/methanol=50:1) to provide a white solid, which was triturated in EtOAc/ether (v/v=1:2, 15 mL) to give the title compound as a white solid (40 mg, 32%). Its analytic data are shown in Table 1.

Example 7: Compound C7

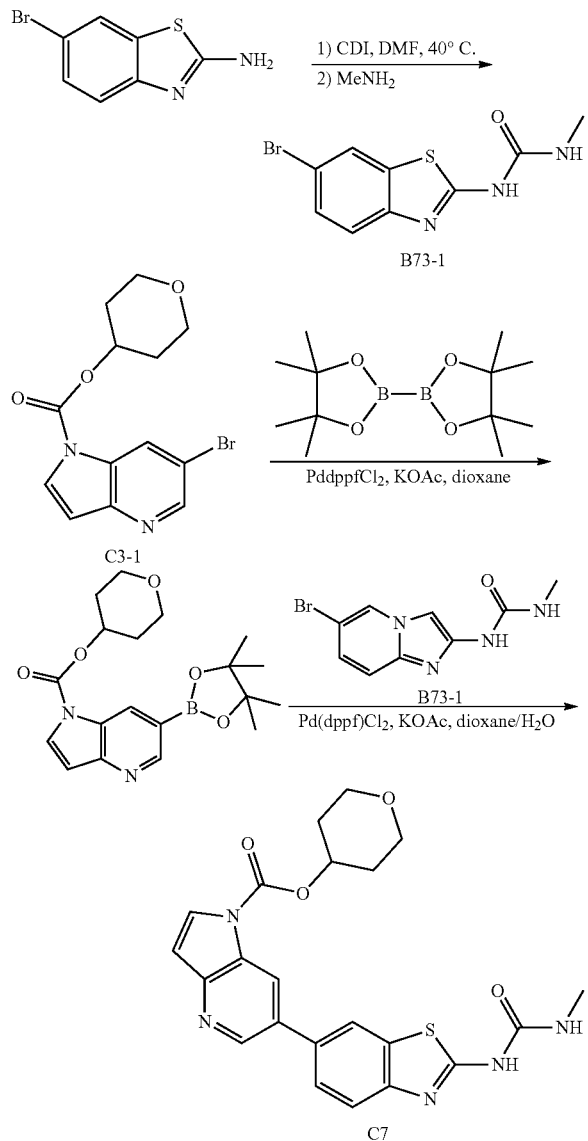

Step 1: 1-(6-bromo-1,3-benzothiazol-2-yl)-3-methyl-urea (B73-1)

To a solution of 6-bromo-1,3-benzothiazol-2-amine (1.0 g, 4.4 mmol) in DMF (100 mL) was added 1,1'-carbonyldiimidazole (CDI, 2.1 g, 13.1 mmol) in portions. The mixture was stirred at 40° C. overnight. Methylamine hydrochloride salt (877 mg, 13.1 mmol) were added to the reaction mixture, and the mixture was stirred overnight. Then the mixture was poured into water. White solid crushed out of the mixture were collected by filtration to afford intermediate B73-1 (1 g, 80%). 1H NMR (400 MHz, DMSO-d6) δ 10.92 (s, 1H), 8.13 (s, 1H), 7.56-7.45 (m, 2H), 6.62 (s, 1H), 2.71 (d, J=4.4 Hz, 1H).

Step 2: tetrahydropyran-4-yl 6-[2-(methylcarbamoylamino)-1,3-benzothiazol-6-yl]pyrrolo[3,2-b]pyridine-1-carboxylate (C7)

To 1,4-dioxane (10 mL) under $N_2$ were added sequentially C3-1 (91 mg, 0.28 mmol), 4,4,5,5-tetramethyl-2-(4,4,5,5-tetramethyl-1,3,2-dioxaborolan-2-yl)-1,3,2-dioxaborolane (137 mg, 0.54 mmol), potassium acetate (55 mg, 0.58 mmol), [1,1'-bis(diphenylphosphino)ferrocene]dichloropalladium(II) (Pd(dppf)Cl$_2$) (21 mg, 0.028 mmol). The mixture was stirred at 100° C. for 5 h. Cooled to room temperature and filtered. To the filtrate were sequentially added B73-1 (58 mg, 0.2 mmol), K$_2$CO$_3$ (70 mg, 0.5 mmol), Pd(dppf)Cl$_2$ (15 mg, 0.02 mmol), and H$_2$O (1 mL) under N$_2$. The mixture was stirred at 100° C. under N$_2$ overnight. The mixture was cooled to room temperature, filtered, and the filtrate was concentrated. The residue was purified by silica gel column chromatography (dichloromethane/methanol=50:1) to provide a white solid, which was triturated in EtOAc/ether (v/v=1:2, 15 mL) to give the title compound as a white solid (25 mg, 20%). Its analytic data are shown in Table 1.

Example 8: Compound C8

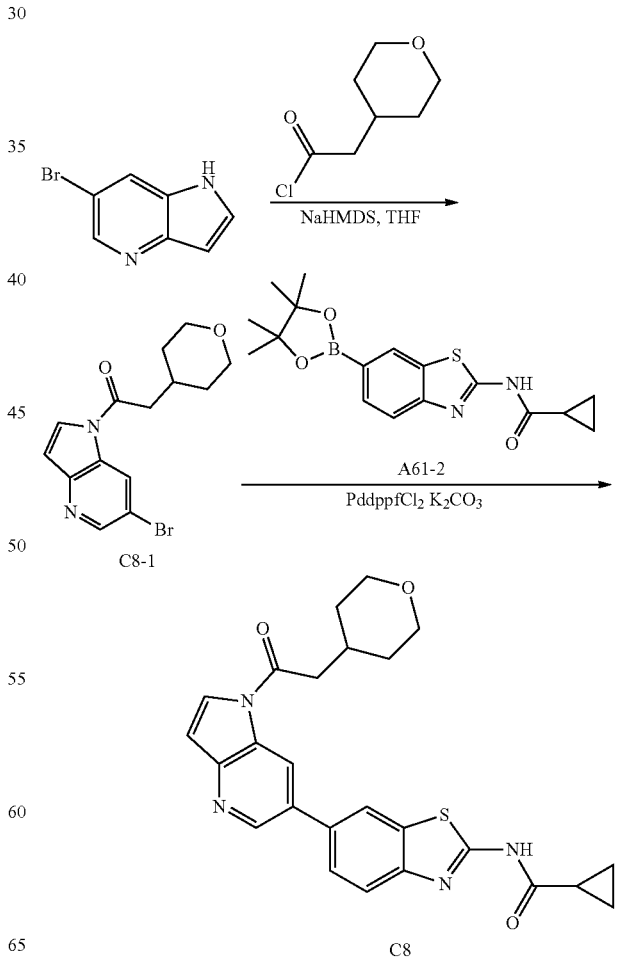

Step 1: Intermediate 1-(6-bromopyrrolo[3,2-b]pyridin-1-yl)-2-tetrahydropyran-4-yl-ethanone (C8-1)

To a solution of 6-bromo-1H-pyrrolo[3,2-b]pyridine (40 mg, 0.21 mmol) in anhydrous THF (10 mL) under $N_2$ was added slowly NaHMDS (0.4 mmol, 0.2 mL) solution. Stirred at 0° C. for 15 min. To the mixture was added dropwise 2-tetrahydropyran-4-ylacetyl chloride (100 mg, 0.62 mmol) in THF. When the reaction was complete, the reaction quenched with saturated aqueous $NH_4Cl$ solution (20 mL). Extracted with EtOAc (20 mL) and the organic layer was separated, dried, and concentrated to provide the title compound as a yellow solid (20 mg).

Step 2: N-[6-[1-(2-tetrahydropyran-4-ylacetyl)pyrrolo[3,2-b]pyridin-6-yl]-1,3-benzothiazol-2-yl]cyclopropanecarboxamide (C8)

To 1,4-dioxane/$H_2O$ (10 mL/1 mL) under $N_2$ were added sequentially C8-1 (30 mg, 0.08 mmol), A61-2 (43 mg, 0.13 mmol), $K_2CO_3$ (30 mg, 0.21 mmol), Pd(dppf)$Cl_2$ (8 mg, 0.008 mmol). The mixture was stirred at 100° C. under $N_2$ overnight. The mixture was cooled to room temperature, and concentrated. The residue was purified by silica gel column chromatography (dichloromethane/methanol=40:1) to provide the title compound as a white solid (10 mg, 23%). Its analytic data are shown in Table 1.

Example 9: Compound C9

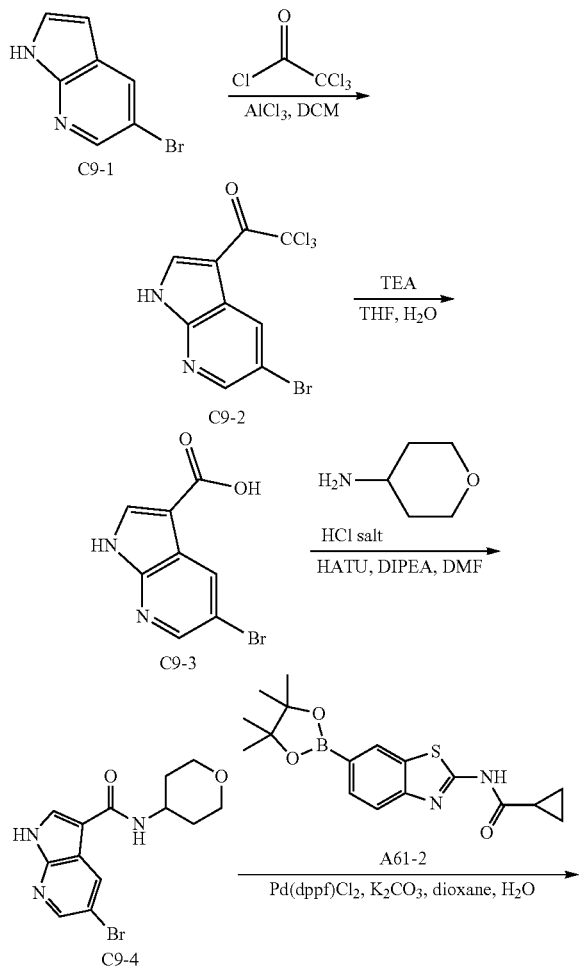

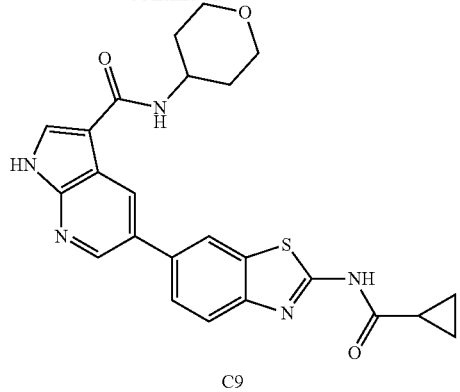

Step 1: 1-(5-bromo-1H-pyrrolo[2,3-b]pyridin-3-yl)-2,2,2-trichloro-ethanone (C9-2)

To a solution of 5-bromo-1H-pyrrolo[2,3-b]pyridine (C9-1) (1.97 g, 10 mmol) in $CH_2Cl_2$ (50 mL) was added $AlCl_3$ (6.67 g, 50 mmol), and the mixture was stirred at room temperature for 10 min. Trichloroacetyl chloride (2.73 g, 15 mmol) was added, and the resulting mixture was stirred at room temperature overnight. Then the reaction mixture was poured into ice-water, filtered, and the filter cake was washed with $CH_2Cl_2$ (100 mL) and dried under vacuum to provide the title compound C9-2 as a light yellow solid (3.5 g, 100%).

Step 2: 5-bromo-1H-pyrrolo[2,3-b]pyridine-3-carboxylic acid (C9-3)

To a solution of C9-2 (3.5 g, 10 mmol) in a mixture of THF (40 mL) and water (10 mL) was added $Et_3N$ (5 mL). The mixture was stirred at room temperature overnight. Then the mixture was concentrated and the resulting residue was added to a HCl solution (0.5 N, 20 mL), stirred at room temperature for 20 minutes, filtered, and the filter cake was washed with water (20 mL), dried under vacuum to afford the title compound C9-3 as an off-white solid (2.43 g, 100%). $^1$H NMR (400 MHz, DMSO-$d_6$) δ 12.66 (s, 1H), 8.41 (s, 1H), 8.39 (s, 1H), 8.21 (s, 1H).

Step 3: 5-bromo-N-tetrahydropyran-4-yl-1H-pyrrolo[2,3-b]pyridine-3-carboxamide (C9-4)

Intermediate C9-3 (430 mg, 1.78 mmol) and tetrahydropyran-4-amine hydrochloride (319 mg, 2.32 mmol) were added to DMF (5 mL). DIPEA (805 mg, 6.24 mmol) and HATU (881 mg, 2.32 mmol) were added at room temperature, and the resulting mixture was stirred at room temperature overnight. Then the mixture was concentrated and the residue was partitioned between water (10 mL) and $CH_2Cl_2$ (20 mL). The aqueous layer was further extracted with $CH_2Cl_2$ (20 mL). Combined organic layers were concentrated. The residue was purified by silica gel column chromatography (petroleum ether/EtOAc=1:1) to provide the crude C9-4, which was triturated in $CH_2Cl_2$ (20 mL) for 20 min, filtered, and the filter cake was washed with $CH_2Cl_2$ (20 mL). The filter cake was dried under vacuum to give the title compound as a white solid (190 mg, 33%). $^1$H NMR (400 MHz, DMSO-$d_6$) δ 12.33 (s, 1H), 8.56 (d, J=2.4 Hz, 1H), 8.34 (d, J=2.4 Hz, 1H), 8.25 (d, J=2.8 Hz, 1H), 7.94 (d, J=7.6

Hz, 1H), 4.06-3.95 (m, 1H), 3.93-3.84 (m, 2H), 3.43-3.39 (m, 2H), 1.84-1.73 (m, 2H), 1.61-1.47 (m, 2H).

Step 4: 5-[2-(cyclopropanecarbonylamino)-1,3-benzothiazol-6-yl]-N-tetrahydropyran-4-yl-1H-pyrrolo[2,3-b]pyridine-3-carboxamide (C9)

To 1,4-dioxane/H₂O (10 mL/1 mL) under N₂ were added C9-4 (97 mg, 0.3 mmol), A61-2 (155 mg, 0.45 mmol), K₂CO₃ (104 mg, 0.75 mmol), Pd(dppf)Cl₂ (22 mg, 0.03 mmol). The mixture was stirred at 100° C. under N₂ overnight. The mixture was cooled to room temperature, and concentrated. The residue was purified by silica gel column chromatography (dichloromethane/methanol=20:1) to afford crude C9, which was triturated in EtOAc (5 mL) for 30 min, filtered, and the filter cake was washed with EtOAc (5 mL) and ether (5 mL). The filter cake was dried under vacuum to give the title compound as a gray solid (85 mg, 61%). Its analytic data are shown in Table 1.

Example 10: Compound C10

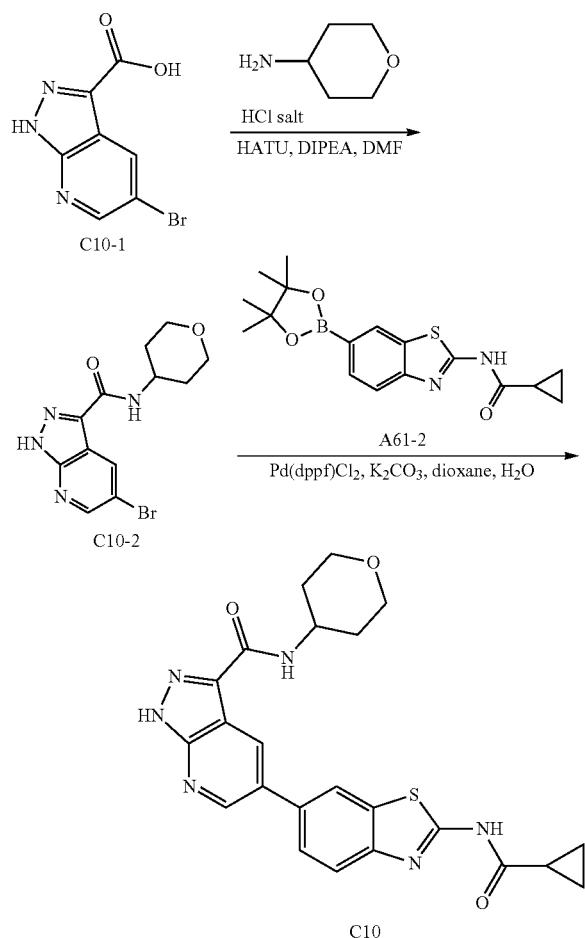

Step 1: 5-bromo-N-tetrahydropyran-4-yl-1H-pyrazolo[3,4-b]pyridine-3-carboxamide (C10-2)

Intermediate 5-bromo-1H-pyrazolo[3,4-b]pyridine-3-carboxylic acid (C10-1) (250 mg, 1.03 mmol) and tetrahydropyran-4-amine hydrochloride (213 mg, 1.55 mmol) were added to DMF (5 mL). DIPEA (400 mg, 3.1 mmol) and HATU (510 mg, 1.34 mmol) were added at room temperature, and the resulting mixture was stirred at room temperature for 2 h. Then the mixture was concentrated and the residue was partitioned between saturated aqueous Na₂CO₃ solution (10 mL) and CH₂Cl₂ (20 mL). The organic layer was separated and concentrated. The residue was triturated with EtOAc (5 mL) and stirred for 5 min, filtered, and the filter cake was washed with EtOAc (5 mL) and CH₂Cl₂ (10 mL). The filter cake was dried under vacuum to give the title compound C10-2 as an off-white solid (150 mg, 45%). ¹H NMR (400 MHz, DMSO-d₆) δ 8.51 (s, 1H), 8.47 (s, 1H), 8.25 (s, 1H), 4.09-4.00 (m, 1H), 3.90-3.84 (m, 2H), 3.41-3.40 (m, 2H), 1.79-1.59 (m, 4H).

Step 2: 5-[2-(cyclopropanecarbonylamino)-1,3-benzothiazol-6-yl]-N-tetrahydropyran-4-yl-1H-pyrazolo[3,4-b]pyridine-3-carboxamide (C10)

To 1,4-dioxane/H₂O (10 mL/1 mL) under N₂ were added C10-2 (97 mg, 0.3 mmol), A61-2 (155 mg, 0.45 mmol), K₂CO₃ (104 mg, 0.75 mmol), Pd(dppf)Cl₂ (22 mg, 0.03 mmol). The mixture was stirred at 100° C. under N₂ overnight. The mixture was cooled to room temperature, and concentrated. The residue was purified by silica gel column chromatography (dichloromethane/methanol=20:1) to afford crude C10, which was triturated in EtOAc (10 mL) for 30 min, filtered, and the filter cake was washed with EtOAc (5 mL) and ether (5 mL). The filter cake was dried under vacuum to provide the title compound as a gray solid (33 mg, 24%). Its analytic data are shown in Table 1.

Example 11: Compound C11

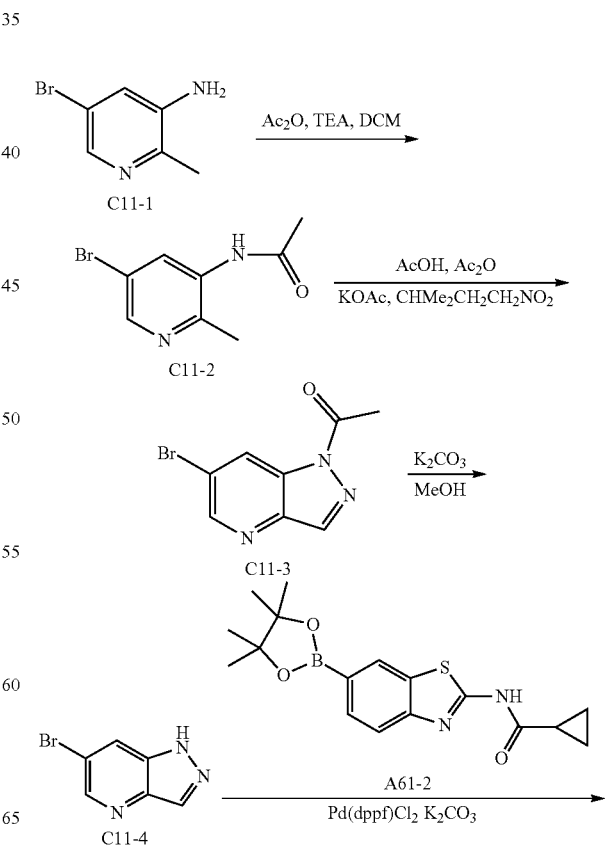

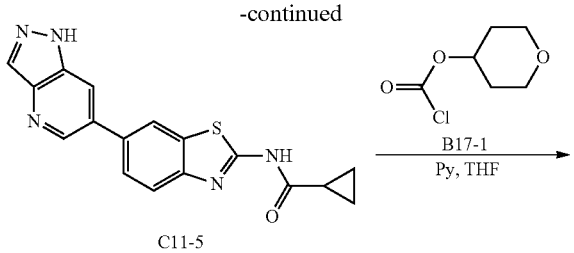

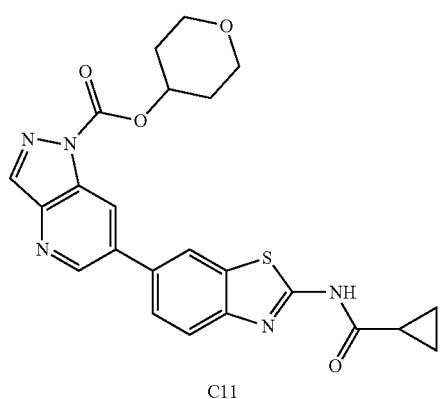

Step 1: N-(5-bromo-2-methyl-3-pyridyl)acetamide (C11-2)

5-Bromo-2-methyl-pyridin-3-amine (C11-1) (1.86 g, 10 mmol), Ac$_2$O (1.73 g, 17 mmol), and Et3N (2.32 g, 23 mmol) were added to CH$_2$Cl$_2$ (10 mL). The mixture was stirred at room temperature overnight. After the reaction was complete, the reaction was quenched with saturated aqueous NaHCO$_3$ solution (25 mL), and the resulting mixture was extracted with EtOAc (30 mL). The organic layer was dried over anhydrous Na$_2$SO$_4$, filtered, and the filtrate was concentrated to provide the crude title compound C11-2.

Step 2: 1-(6-bromopyrazolo[4,3-b]pyridin-1-yl)ethanone (C11-3)

Intermediate C11-2 (100 mg, 0.44 mmol), KOAc (94 mg, 0.96 mmol) and Ac$_2$O (265 mg, 1.31 mmol) were dissolved in toluene (10 mL) under N$_2$, and the mixture was refluxed at 120° C. for 20 min Isopentyl nitrite (64 mg, 0.55 mmol) was added via a syringe. The reaction continued overnight. TLC was used to monitor the reaction and the reaction was incomplete. The mixture was extracted with EtOAc (20 mL). The organic layer was collected, dried over anhydrous Na$_2$SO$_4$, filtered, and the filtrate was concentrated. The residue was purified by silica gel column chromatography (petroleum ether/EtOAc=5:1) to afford the title compound as a yellow solid (50 mg, 48%). $^1$H NMR (400 MHz, CDCl$_3$) δ 8.91 (s, 1H), 8.75 (s, 1H), 8.32 (s, 1H), 2.80 (s, 3H).

Step 3: 6-bromo-1H-pyrazolo[4,3-b]pyridine (C11-4)

A mixture of C11-3 (50 mg, 0.15 mmol), K$_2$CO$_3$ (40 mg, 0.31 mmol) in MeOH (5 mL) was stirred at 80° C. for 1 h. After the reaction was complete, the mixture was diluted with EtOAc (20 mL). The organic layer was dried over anhydrous Na$_2$SO$_4$, filtered, and the filtrate was concentrated to afford the title compound (40 mg) as a crude product.

Step 4: N-[6-(1H-pyrazolo[4,3-b]pyridin-6-yl)-1,3-benzothiazol-2-yl]cyclopropanecarboxamide (C11-5)

To 1,4-dioxane/H$_2$O (10 mL/1 mL) under N$_2$ were added C11-4 (40 mg, 0.20 mmol), A61-2 (104 mg, 0.30 mmol), K$_2$CO$_3$ (69 mg, 0.51 mmol), Pd(dppf)Cl$_2$ (15 mg, 0.02 mmol). The mixture was stirred at 100° C. under N$_2$ overnight. The mixture was cooled to room temperature, and concentrated. The residue was purified by silica gel column chromatography (dichloromethane/methanol=40:1) to afford crude C11-5 (30 mg, 23.8%). $^1$H NMR (400 MHz, DMSO-d6) δ 13.43 (s, 1H), 12.73 (s, 1H), 8.90 (s, 1H), 8.45 (s, 1H), 8.33 (s, 1H), 8.23 (s, 1H), 7.86 (s, 2H), 2.00 (s, 1H), 0.97 (s, 4H).

Step 5: tetrahydropyran-4-yl 6-[2-(cyclopropanecarbonylamino)-1,3-benzothiazol-6-yl]pyrazolo[4,3-b]pyridine-1-carboxylate (C11)

To a solution of C11-5 (30 mg, 0.09 mmol) in THF (10 mL) was added pyridine (36 mg, 0.45 mmol), stirred at 0° C., then was added a solution of B17-1 (15 mg, 0.089 mmol) in THF. After the reaction was complete, the reaction was quenched with a saturated aqueous NaHCO$_3$ solution (5 mL), extracted with EtOAc. The organic layer was separated, washed with brine (10 mL×2), dried over anhydrous Na$_2$SO$_4$, filtered, and the filtrate was concentrated. The residue was purified by silica gel column chromatography (dichloromethane/methanol=50:1) to provide the title compound (C11) as a white solid (10 mg, 23%). Its analytic data are shown in Table 1.

Example 12: C12 Compound

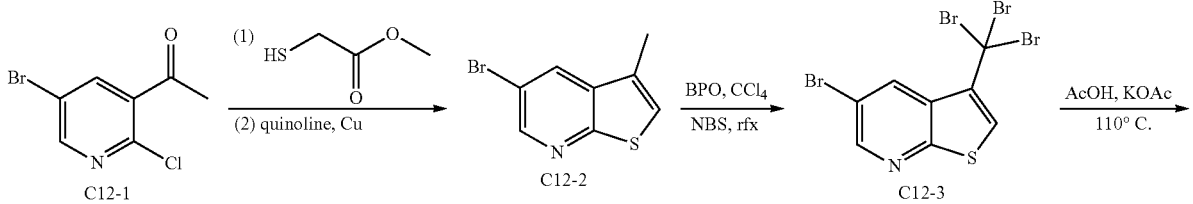

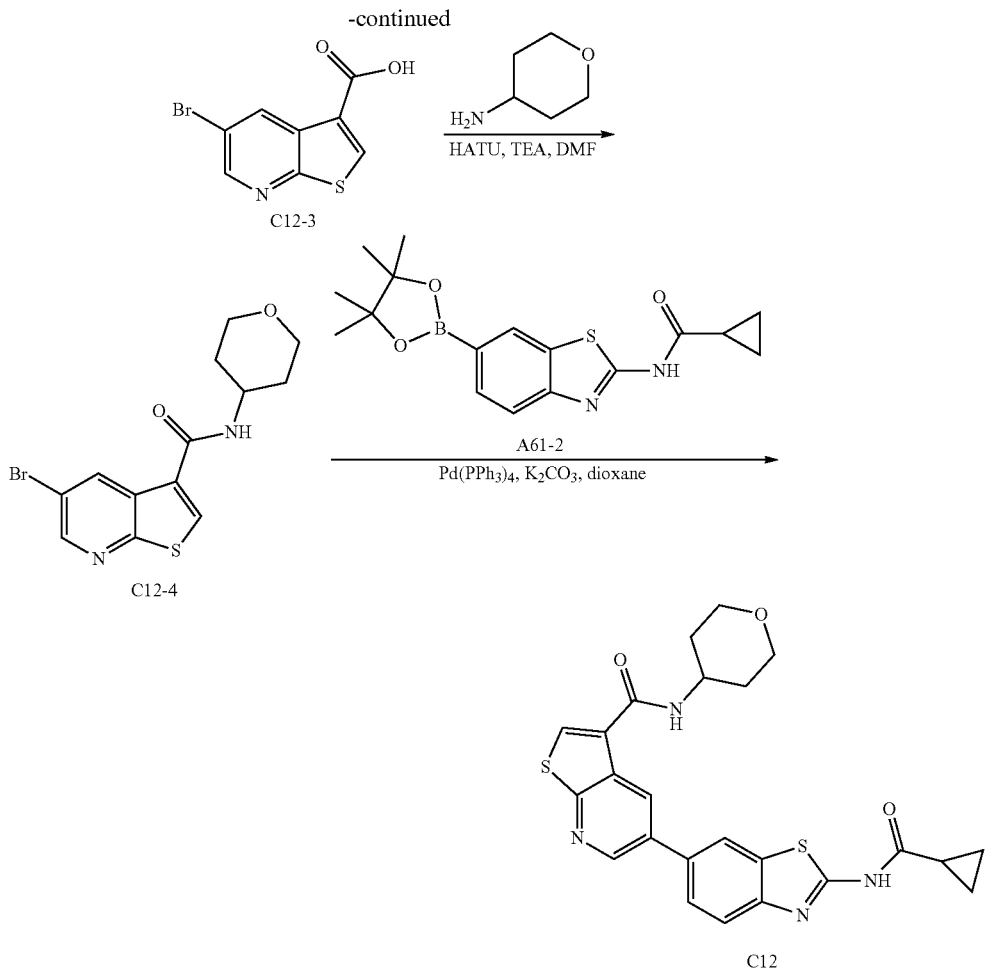

Step 1: 5-bromo-3-methyl-thieno[2,3-b]pyridine (C12-2)

A solution of 1-(5-bromo-2-chloro-3-pyridyl)ethanone (C12-1) (500 mg, 2.1 mmol), methyl 2-sulfanylacetate (445 mg, 4.2 mmol) and $Cs_2CO_3$ (1.3 mg, 4.2 mmol) in dimethylacetamide (DMA) (10 mL) was heated at 100° C. overnight. The mixture was cooled to room temperature, partitioned between brine (20 mL) and $CH_2Cl_2$ (20 mL). The organic layer was separated, dried over anhydrous $Na_2SO_4$, filtered, and the filtrate was concentrated. The residue was dissolved in quinoline (5 mL) and copper powder (265 mg, 4.2 mmol) was added. The mixture was heated at 170° C. for 3 h. The crude product was purified by silica gel column chromatography (petroleum ether/EtOAc=100:1) to provide the title compound (C12-2) as a yellow solid (430 mg, 89%). $^1$H NMR (400 MHz, $CDCl_3$) δ 8.60 (s, 1H), 8.10 (s, 1H), 7.20 (s, 1H), 2.41 (s, 3H).

Step 2: 5-bromo-3-(tribromomethyl)thieno[2,3-b]pyridine (C12-3)

A solution of C12-2 (430 mg, 1.9 mmol), N-bromosuccinimide (NB S) (1 g, 5.7 mmol) and benzyl peroxide (BPO) (145 mg, 0.6 mmol) in $CCl_4$ (10 mL) was refluxed under $N_2$ overnight. The mixture was cooled to room temperature and concentrated. The residue was partitioned between brine (10 mL) and $CH_2Cl_2$ (10 mL). The organic layer was separated, dried over anhydrous $Na_2SO_4$, filtered, and the filtrate was concentrated. The residue was purified by silica gel column chromatography (petroleum ether/EtOAc=100:1) to provide the title compound (C12-3) as a yellow solid (720 mg, 82%). $^1$H NMR (400 MHz, $CDCl_3$) δ 8.83 (s, 1H), 8.70 (s, 1H), 8.17 (s, 1H).

Step 3: 5-bromothieno[2,3-b]pyridine-3-carboxylic acid (C12-4)

A solution of C12-3 (100 mg, 0.21 mmol) in acetic acid (5 mL) was added KOAc (62 mg, 0.63 mmol), heated at 110° C. for 1 h. Cooled to room temperature, filtered to collect the product C12-5 as a yellow solid (45 mg, 83%). $^1$H NMR (400 MHz, DMSO-$d_6$) δ 13.41 (s, 1H), 8.88 (s, 1H), 8.83 (s, 1H), 8.77 (s, 1H).

Step 4: 5-bromo-N-tetrahydropyran-4-yl-thieno[2,3-b]pyridine-3-carboxamide; methane (C12-5)

A solution of C12-4 (45 mg, 0.17 mmol) and HATU (99 mg, 0.26 mmol) in DMF (5 mL) was stirred at room temperature for 1 h. Tetrahydropyran-4-amine (36 mg, 0.26 mmol) and DIPEA (66 mg, 0.51 mmol) were added at room temperature, and the resulting mixture was stirred at room temperature for 1 h. Then the mixture was diluted with EtOAc (10 mL) and the organic layer was washed with a saturated aqueous $NaHCO_3$ solution (10 mL×3). The organic layer was dried over anhydrous Na$_2$SO$_4$, filtered, and the filtrate was concentrated to provide the title compound C12-5 as white solid crude product (61 mg). $^1$H NMR (400 MHz, CDCl$_3$) δ 8.93 (s, 1H), 8.65 (s, 1H), 7.91 (s, 1H), 5.91 (d, J=8.0 Hz, 1H), 4.28-4.17 (m, 1H), 4.05-4.00 (m, 2H), 3.58-3.52 (m, 2H), 2.07-2.02 (m, 2H), 1.65-1.60 (m, 2H).

Step 5: 5-[2-(cyclopropanecarbonylamino)-1,3-benzothiazol-6-yl]-N-tetrahydropyran-4-yl-thieno[2,3-b]pyridine-3-carboxamide (C12)

To 1,4-dioxane (5 mL) were added C12-5 (60 mg, 0.17 mmol), A61-2 (89 mg, 0.26 mmol), K$_2$CO$_3$ (83 mg, 0.6 mmol), Pd(PPh$_3$)$_4$ (23 mg, 0.02 mmol), and H$_2$O (1 mL) under N$_2$. The mixture was stirred at 90° C. under N$_2$ overnight. The mixture was cooled to room temperature, and concentrated. The residue was purified by silica gel column chromatography (dichloromethane/methanol=100:1) to provide the title compound C12 as a white solid (42 mg, 52%). Its analytic data are shown in Table 1.

Example 13: C13 Compound

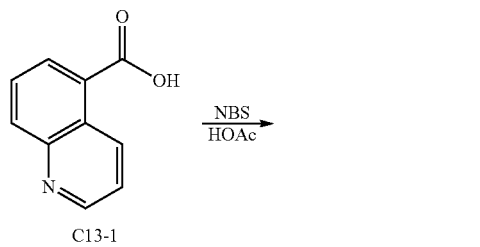

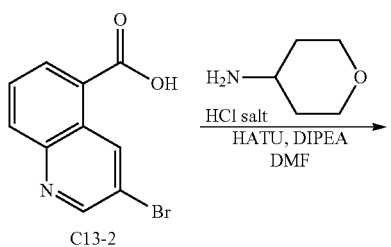

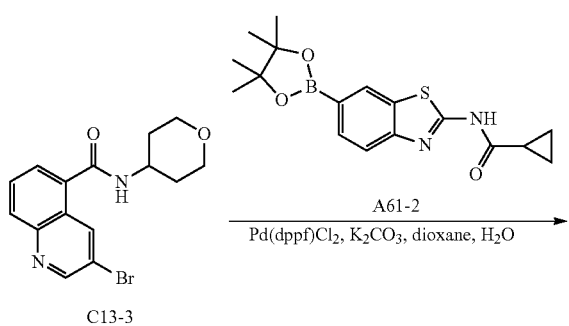

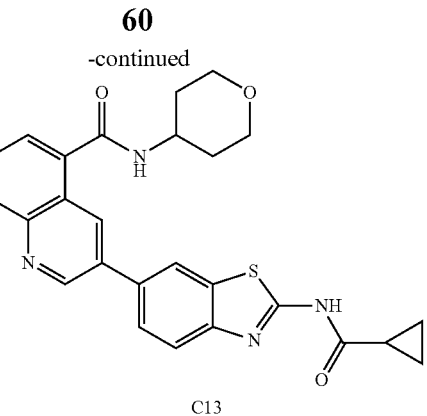

Step 1: 3-bromoquinoline-5-carboxylic acid (C13-2)

To a solution of quinoline-5-carboxylic acid (C13-1) (620 mg, 3.58 mmol) in AcOH (10 mL) was added NBS (956 mg, 5.37 mmol) at room temperature. The mixture was stirred at 120° C. overnight. The mixture was cooled to room temperature, filtered, and the filter cake was washed with EtOAc (5 mL). The filter cake was dried under vacuum to provide the title compound C13-2 as a gray solid (crude, 700 mg).

Step 2: 3-bromo-N-tetrahydropyran-4-yl-quinoline-5-carboxamide (C13-3)

A solution of C13-2 (crude, 700 mg) in DMF were added tetrahydropyran-4-amine hydrochloride (573 mg, 4.2 mmol), DIPEA (1.08 g, 8.3 mmol) and HATU (1.37 g, 3.6 mmol). The mixture was stirred at room temperature for overnight. Then the mixture was concentrated, and the residue was diluted with a saturated aqueous Na$_2$CO$_3$ solution (10 mL) and extracted with EtOAc (50 mL×3). The organic layers were combined, dried over anhydrous Na$_2$SO$_4$, filtered, and the filtrate was concentrated. The residue was purified by silica gel column chromatography (petroleum ether/EtOAc=2:1) to provide the title compound C13-3 as a gray solid (360 mg). $^1$H NMR (400 MHz, CDCl$_3$) δ 8.96-8.93 (m, 2H), 8.17-8.13 (m, 1H), 7.69-7.66 (m, 2H), 6.09 (d, J=8.0 Hz, 1H), 4.39-4.20 (m, 1H), 4.09-3.98 (m, 2H), 3.57 (td, J=12.0, 2.0 Hz, 2H), 2.15-2.04 (m, 2H), 1.67-1.55 (m, 2H).

Step 3: 3-[2-(cyclopropanecarbonylamino)-1,3-benzothiazol-6-yl]-N-tetrahydropyran-4-yl-quinoline-5-carboxamide (C13)

To 1,4-dioxane (10 mL) under N$_2$ were added C13-3 (134 mg, 0.4 mmol), A61-2 (207 mg, 0.6 mmol), K$_2$CO$_3$ (138 mg, 1 mmol), Pd(dppf)Cl$_2$ (30 mg, 0.04 mmol) and water (1 mL). The mixture was stirred at 100° C. under N$_2$ overnight. The mixture was cooled to room temperature, filtered, and the filtrate was concentrated. The residue was purified by silica gel column chromatography (dichloromethane/methanol=20:1) to provide crude C13 product, which was triturated in EtOAc (10 mL) for 30 min, filtered, and the filter cake was washed with EtOAc (5 mL) and diethyl ether (5 mL). The filter cake was dried under vacuum to give the title compound as a gray solid (100 mg, 53%). Its analytic data are shown in Table 1.

Example 14: Compound C14

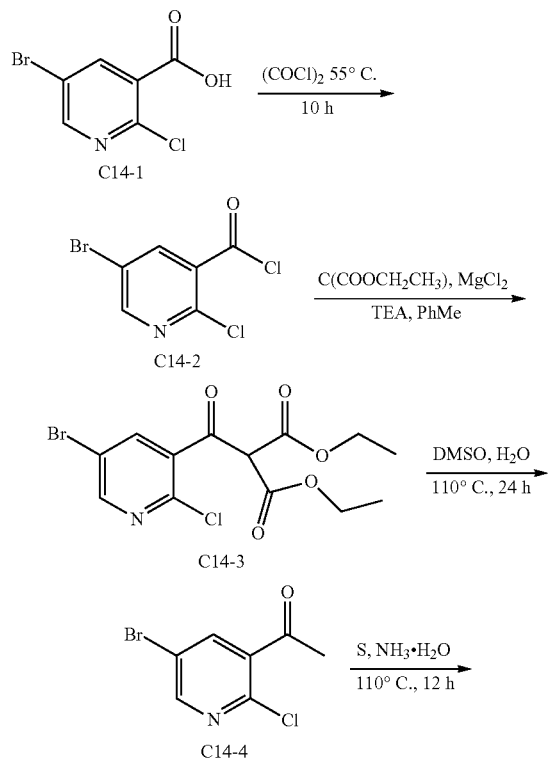

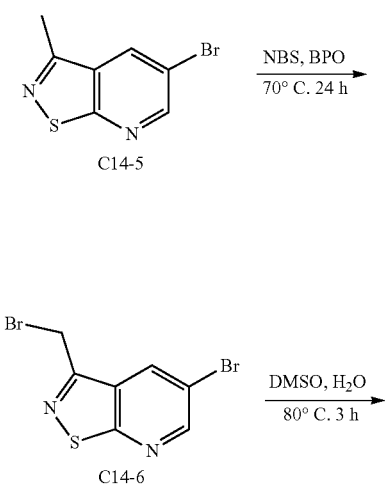

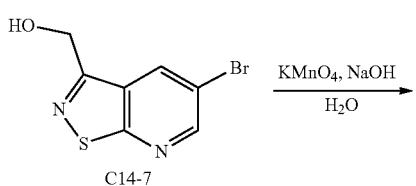

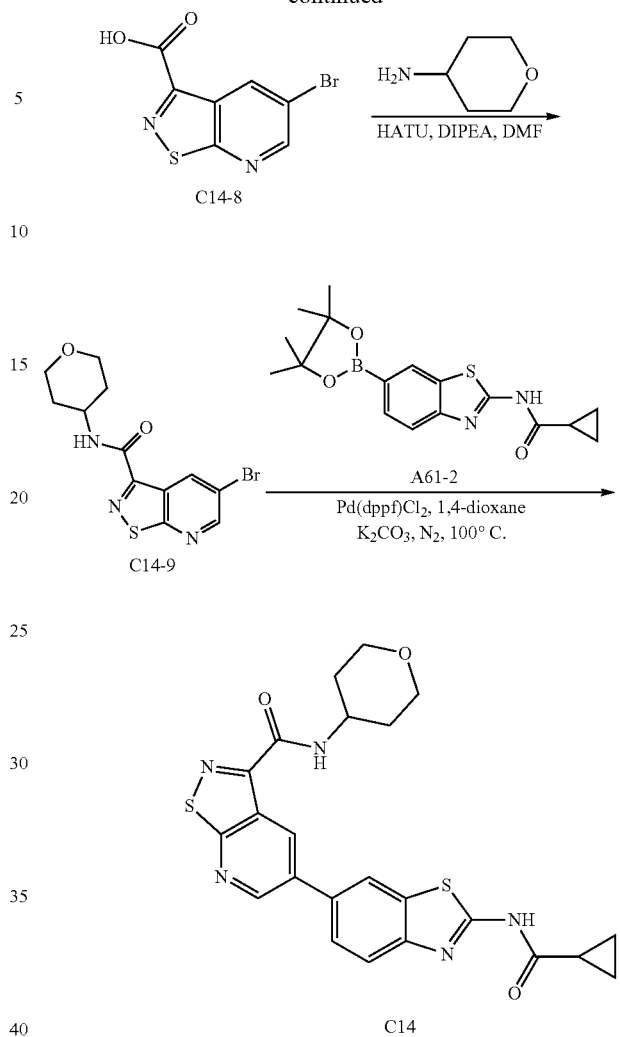

Step 1: 5-bromo-2-chloro-pyridine-3-carbonyl chloride (C14-2)

A solution of 5-bromo-2-chloro-pyridine-3-carboxylic acid (C14-1) (2.35 g, 10 mmol) in oxalyl chloride (10 mL) was heated at 55 C overnight. The mixture was cooled to room temperature and concentrated to provide the title compound (C14-2) as a yellow oil (crude, 3 g).

Step 2: diethyl 2-(5-bromo-2-chloro-pyridine-3-carbonyl)propanedioate (C14-3)

To a solution of C14-2 (crude 3 g) in toluene (16 mL) was added sequentially MgCl$_2$ (660 mg, 7.0 mmol), Et$_3$N (2.5 g, 25 mmol), and the mixture was stirred at room temperature for 45 min. Diethyl malonate (1.9 g, 22 mmol) in toluene was added dropwise into the resulting mixture, and stirred for an additional 3 h. Water (30 mL) was added to quench the reaction. The resulting mixture was extracted with EtOAc (38 mL×2). The combined organic layers were concentrated to afford the title compound as a crude yellow solid (4.5 g). LC-MS (m/z): 377.5 [M+H]$^+$.

Step 3: 1-(5-bromo-2-chloro-3-pyridyl)ethanone (C14-4)

A solution of C14-3 (crude, 4.5 g) in DMSO (10 mL) was treated with concentrated hydrochloric acid to adjust the pH to about 5. The mixture was heated at 120° C. overnight. The mixture was cooled to room temperature, and partitioned between water (50 mL) and EtOAc (80 mL). The organic layer was separated and concentrated. The residue was purified by silica gel column chromatography (petroleum ether/EtOAc=50:1) to provide the title compound C14-4 as a yellow oil (1.3 g, 55.8%). $^1$H NMR (400 MHz, CDCl$_3$) δ 8.52 (d, J=2.4 Hz, 1H), 8.00 (d, J=2.4 Hz, 1H), 2.68 (s, 3H).

Step 4: 5-bromo-3-methyl-isothiazolo[5,4-b]pyridine (C14-5)

To a solution f C14-4 (117 mg, 0.50 mmol) and sulfur (18 mg, 0.55 mmol) in NH$_3$—H$_2$O (3 mL) was added MeOH (2 mL). The mixture was heated at 110° C. overnight. The mixture was cooled to room temperature and diluted with EtOAc (5 mL). The organic layer was separated and concentrated. The residue was purified by silica gel column chromatography (petroleum ether/EtOAc=30:1) to provide the title compound C14-5 (50 mg, 43.8%). $^1$H NMR (400 MHz, CDCl$_3$) δ 8.78 (s, 1H), 8.33 (s, 1H), 2.72 (s, 3H). LC-MS (m/z): 377.5 [M+H]$^+$.

Step 5: 5-bromo-3-(bromomethyl)isothiazolo[5,4-b]pyridine (C14-6)

A solution of C14-5 (100 mg, 0.44 mmol), N-bromosuccinimide (NBS) (85 mg, 0.04 mmol) and benzyl peroxide (BPO) (10 mg, 0.04 mmol) in CCl$_4$ (3 mL) was heated at 70° C. under N$_2$ overnight. The mixture was cooled to room temperature and filtered. The filter cake was washed with CCl$_4$ (2×) and the filtrate collected was concentrated. The residue was purified by silica gel column chromatography (petroleum ether/CH$_2$Cl$_2$=10:1) to provide the title compound (C14-6) as a white solid (90 mg, 66.8%). $^1$H NMR (400 MHz, CDCl$_3$) δ 8.83 (s, 1H), 8.55 (s, 1H), 4.78 (s, 2H). LC-MS (m/z): 306.5 [M+H]$^+$.

Step 6: (5-bromoisothiazolo[5,4-b]pyridin-3-yl)methanol (C14-7)

To a solution of C14-6 (90 mg) in DMSO (1.5 mL) was added water (1 mL), and the mixture was heated at 80° C. and stirred for 1.5 h. The mixture was cooled to room temperature, and partitioned between water (50 mL) and EtOAc (15 mL). The organic layer was separated, washed with brine (6 mL×2), and concentrated. The residue was purified by silica gel column chromatography (petroleum ether/CH$_2$Cl$_2$=3:1) to provide the title compound C14-7 as a white solid (20 mg, 74.5%). $^1$H NMR (400 MHz, CDCl$_3$) δ 8.81 (s, 1H), 8.56 (s, 1H), 5.08 (s, 2H).

Step 7: 5-bromoisothiazolo[5,4-b]pyridine-3-carboxylic acid (C14-8)

A mixture of C14-7 (20 mg, 0.08 mmol) and KOH (8.3 mg, 0.15 mmol) in water (2 mL) at 0° C. was added an aqueous solution of KMnO$_4$ (28 mg, 0.18 mmol). The mixture was stirred at room temperature for 3 h and filtered. The filtrate was washed with EtOAc (5 mL) and the aqueous layer was separated. The pH of the aqueous layer was adjusted to 1.5-2.6 and the crude product was collected as a brown solid (7 mg, 33.9%). $^1$H NMR (400 MHz, DMSO-d6) δ 15.16-13.40 (br s, 1H), 9.06 (s, 1H), 9.04 (s, 1H). LC-MS (m/z): 258.6 [M+H]$^+$.

Step 8: 5-bromo-N-tetrahydropyran-4-yl-isothiazolo[5,4-b]pyridine-3-carboxamide (C14-9)

C14-8 (24 mg, 0.10 mmol), DIPEA (52 mg, 0.40 mmol), HATU (57 mg, 0.15 mmol) and tetrahydropyran-4-amine (27 mg, 0.20 mmol) were added sequentially to DMF (2 mL). The resulting mixture was stirred at room temperature overnight. Then the mixture was diluted with EtOAc (15 mL) and the organic layer was washed with brine (6 mL×2). The organic layer was separated and concentrated. The residue was purified by silica gel column chromatography (petroleum ether/EtOAc=30:1) to provide the title compound (C14-9) as a solid (32 mg, 94.1%). $^1$H NMR (400 MHz, DMSO-d6) δ 9.37 (d, J=2.4 Hz, 1H), 8.82 (d, J=2.0 Hz, 1H), 4.20-4.15 (m, 1H), 4.05-3.95 (m, 2H), 3.60-3.50 (m, 2H), 2.10-1.95 (m, 2H), 1.35-1.32 (m, 2H).

Step 9: 5-[2-(cyclopropanecarbonylamino)-1,3-benzothiazol-6-yl]-N-tetrahydropyran-4-yl-isothiazolo[5,4-b]pyridine-3-carboxamide (C14)

To 1,4-dioxane (3 mL) under N$_2$ were added C14-9 (40 mg, 0.12 mmol), A61-2 (62 mg, 0.18 mmol), K$_2$CO$_3$ (41 mg, 0.30 mmol), Pd(dppf)Cl$_2$ (7 mg, 0.01 mmol) and water (0.5 mL). The mixture was stirred at 110° C. under N$_2$ overnight. The mixture was cooled to room temperature, filtered, and the filtrate was concentrated. The residue was purified by silica gel column chromatography (dichloromethane/methanol=50:1) to provide the title compound C14 as a yellow solid (20 mg, 34.7%). Its analytic data are shown in Table 1.

Example 15: Compound C16

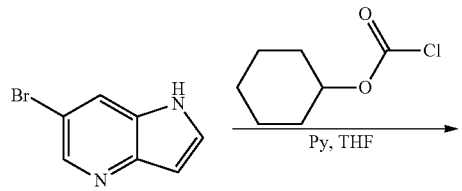

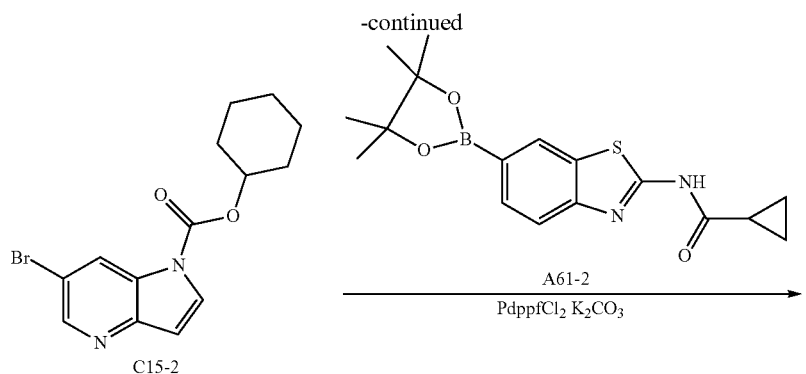

Step 1: cyclohexyl 6-bromopyrrolo[3,2-b]pyridine-1-carboxylate (C15-2)

To a solution of 6-bromo-1H-pyrrolo[3,2-b]pyridine (C15-1) (200 mg, 1.03 mmol) and pyridine (489 mg, 3.08 mmol) in THF (5 mL) under $N_2$ was slowly added cyclohexyl carbonochloridate (500 mg, 3.1 mmol) in THF (2 mL) via a syringe. After the reaction is complete, the reaction was quenched with a saturated aqueous $NaHCO_3$ solution (20 mL), and extracted with $CH_2Cl_2$ (10 mL). The organic layer was separated, dried over anhydrous $Na_2SO_4$, filtered, and the filtrate was concentrated. The residue was purified by silica gel column chromatography (petroleum ether/EtOAc=5:1) to provide the title compound as a yellow solid (260 mg, 80%). $^1$H NMR (400 MHz, $CDCl_3$) δ 8.58 (s, 1H), 7.84 (s, 1H), 6.78 (s, 1H), 5.05 (s, 1H), 2.03-1.39 (m, 11H).

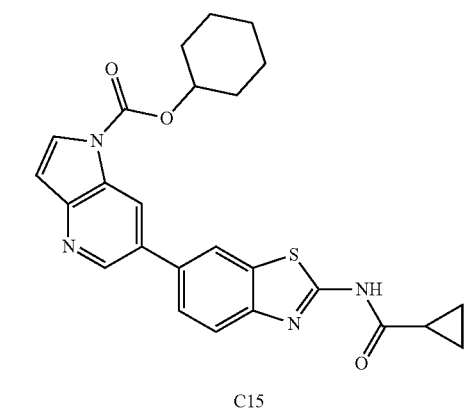

Step 2: cyclohexyl 6-[2-(cyclopropanecarbonylamino)-1,3-benzothiazol-6-yl]pyrrolo[[3,2-b]pyridine-1-carboxylate (C15)

To 1,4-dioxane (10 mL) and water (1 mL) under $N_2$ were added C15-2 (80 mg, 0.25 mmol), A61-2 (127 mg, 0.37 mmol), $K_2CO_3$ (85 mg, 0.62 mmol), Pd(dppf)Cl$_2$ (18 mg, 0.025 mmol) and water (0.5 mL). The mixture was stirred at 100° C. under $N_2$ overnight. The mixture was cooled to room temperature, filtered, and the filtrate was concentrated. The residue was purified by silica gel column chromatography (dichloromethane/methanol=90:1) to provide the title compound C15 as a white solid (50 mg, 44%). Its analytic data are shown in Table 1.

Example 16: Compound C16

Step 1: cyclohexyl 6-[2-(methylcarbamoylamino)-1,3-benzothiazol-6-yl]pyrrolo[3,2-b]pyridine-1-carboxylate (C16)

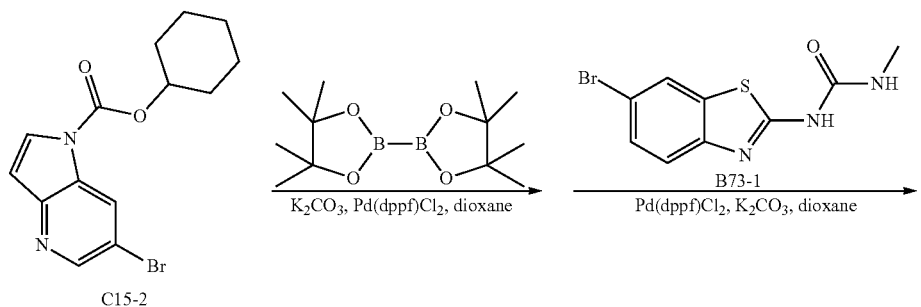

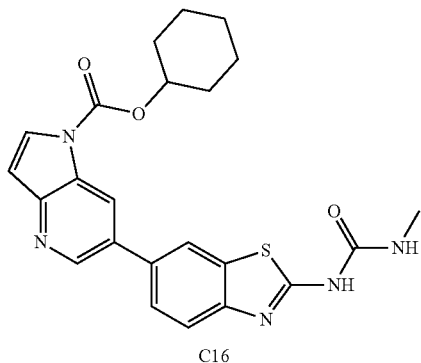

C16

To 1,4-dioxane (10 mL) under N₂ were added C15-2 (100 mg, 0.3 mmol), 4,4,5,5-tetramethyl-2-(4,4,5,5-tetramethyl-1,3,2-dioxaborolan-2-yl)-1,3,2-dioxaborolane (152 mg, 0.6 mmol), potassium acetate (70 mg, 0.7 mmol), (Pd(dppf)Cl₂ (22 mg, 0.03 mmol). The mixture was stirred at 100° C. for 8 h. After the reaction was complete, to the mixture were sequentially added B73-1 (50 mg, 0.2 mmol), K₂CO₃ (70 mg, 0.5 mmol), Pd(dppf)Cl₂ (15 mg, 0.02 mmol), and H₂O (2 mL) under N₂. The mixture was stirred at 90° C. under N₂ for 4 h. The mixture was cooled to room temperature, filtered, and the filtrate was concentrated. The residue was purified by silica gel column chromatography (dichloromethane/methanol=10:1) to provide the title compound C16 as a white solid (25 mg, 28%). Its analytic data are shown in Table 1.

Example 17: Compound 17

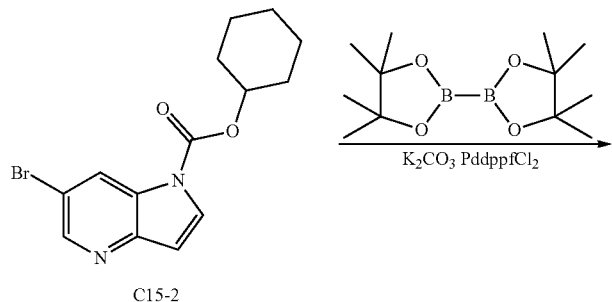

C15-2

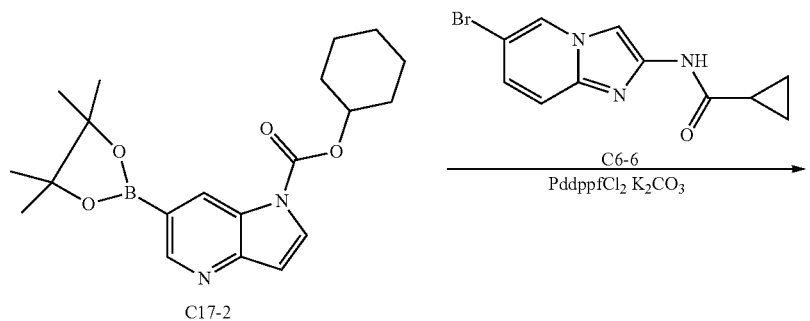

C17-2

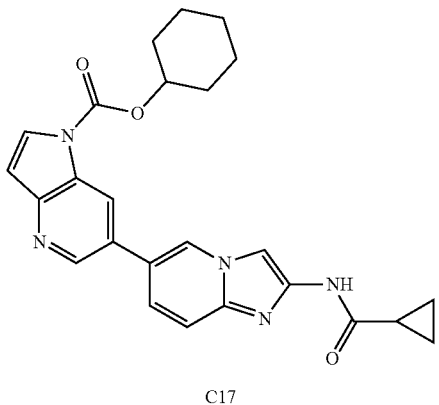

C17

Step 1: cyclohexyl 6-(4,4,5,5-tetramethyl-1,3,2-dioxaborolan-2-yl)pyrrolo[3,2-b]pyridine-1-carboxylate (C17-2)

To 1,4-dioxane (10 mL) under N₂ were added C15-2 (70 mg, 0.22 mmol), 4,4,5,5-tetramethyl-2-(4,4,5,5-tetramethyl-1,3,2-dioxaborolan-2-yl)-1,3,2-dioxaborolane (110 mg, 0.43 mmol), potassium acetate (53 mg, 0.54 mmol), (Pd(dppf)Cl₂ (16 mg, 0.02 mmol). The mixture was stirred at 90° C. for 7 h. After the reaction was complete, the mixture was used in the next step directly.

Step 2: cyclohexyl 6-[2-(cyclopropanecarbonylamino)imidazo[1,2-a]pyridin-6-yl]pyrrolo[[3,2-b]pyridine-1-carboxylate (C17)

To the mixture obtained in Step 1 were sequentially added C6-6 (41 mg, 0.15 mmol), K₂CO₃ (50 mg, 0.36 mmol), Pd(dppf)Cl₂ (11 mg, 0.02 mmol), and H₂O (1 mL) under N₂. The mixture was stirred at 100° C. under N₂ overnight. The mixture was cooled to room temperature, filtered, and the filtrate was concentrated. The residue was purified by silica gel column chromatography (dichloromethane/methanol=80:1) to provide the title compound C17 as a white solid (20 mg, 39%). Its analytic data are shown in Table 1.

Example 18: Compound C18

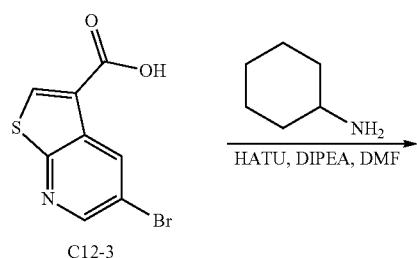

Step 1: 5-bromo-N-cyclohexyl-thieno[2,3-b]pyridine-3-carboxamide (C18-1)

C12-3 (250 mg, 1 mmol) and HATU (570 mg, 1.5 mmol) were dissolved in DMF (15 mL) and the mixture was stirred at room temperature for 10 min DIPEA (387 mg, 3 mmol), and cyclohexylamine (149 mg, 1.5 mmol) were added sequentially to the mixture. The resulting mixture was stirred at room temperature for 5 h. Then the mixture was poured into water (150 mL), and filtered. The filter cake was washed with water and dried to provide the crude as a white solid, which was purified by silica gel column chromatography (petroleum ether/EtOAc=5:1) to provide the title compound C18-1 as a white solid. ¹H NMR (400 MHz, DMSO-d$_6$) δ 8.92 (s, 1H), 8.73 (s, 1H), 8.59 (s, 1H), 8.42 (d, J=7.2 Hz, 1H), 3.83-3.63 (m, 1H), 1.90-1.80 (m, 2H), 1.77-1.70 (m, 2H), 1.35-1.28 (m, 4H), 1.26-1.20 (m, 2H).

Step 2: N-cyclohexyl-5-[2-(cyclopropanecarbonylamino)-1,3-benzothiazol-6-yl]thieno[2,3-b]pyridine-3-carboxamide (C18)

To 1,4-dioxane (10 mL) and water (0.5 mL) were added C18-1 (65 mg, 0.2 mmol), A61-2 (103 mg, 0.3 mmol), K$_2$CO$_3$ (70 mg, 0.5 mmol), and Pd(PPh$_3$)$_4$ (22 mg, 0.02 mmol) under N$_2$. The mixture was stirred at 90° C. under N$_2$ overnight. The mixture was cooled to room temperature, and was concentrated. The residue was purified by silica gel column chromatography (dichloromethane/methanol=50:1) to provide a white solid, which was triturated in EtOAc/ether (v/v=1:2, 15 mL) to give the title compound C18 as a white solid (50 mg, 53%). Its analytic data are shown in Table 1.

Example 19: Compound C19

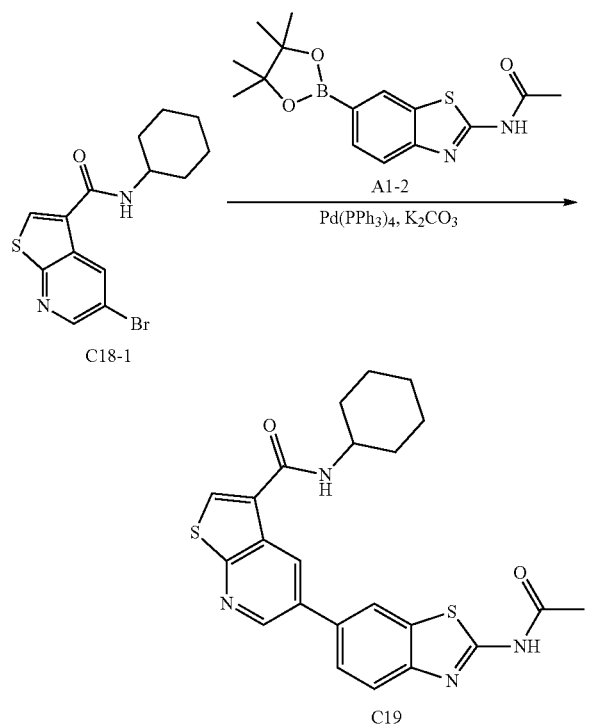

C19

Step 1: 5-(2-acetamido-1,3-benzothiazol-6-yl)-N-cyclohexyl-thieno[2,3-b]pyridine-3-carboxamide (C19)

To 1,4-dioxane (10 mL) and water (0.5 mL) were added C18-1 (50 mg, 0.15 mmol), N-[6-(4,4,5,5-tetramethyl-1,3,2-dioxaborolan-2-yl)-1,3-benzothiazol-2-yl]acetamide (A1-2) (70 mg, 0.22 mmol), K$_2$CO$_3$ (60 mg, 0.4 mmol), and Pd(PPh$_3$)$_4$ (11 mg, 0.015 mmol) under N$_2$. The mixture was stirred at 90° C. under N$_2$ overnight. The mixture was cooled to room temperature, and was concentrated. The residue was purified by silica gel column chromatography (dichloromethane/methanol=50:1) to provide a white solid, which was triturated in EtOAc/ether (v/v=1:2, 15 mL) to give the title compound C18 as a white solid (12 mg, 18%). Its analytic data are shown in Table 1.

Example 20: Compound C20

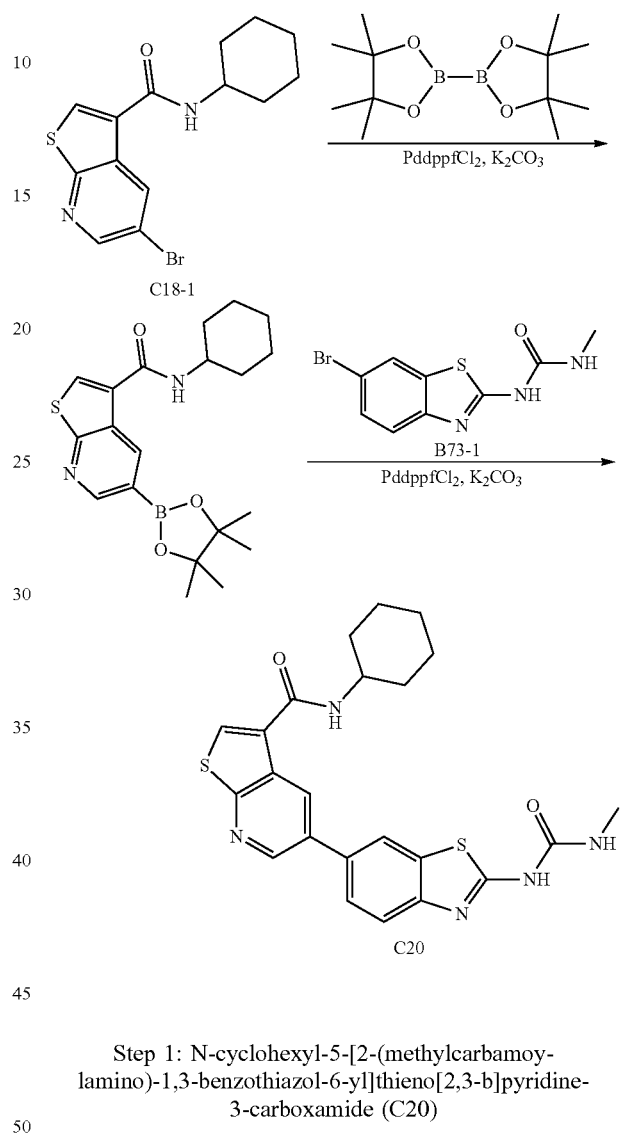

C20

Step 1: N-cyclohexyl-5-[2-(methylcarbamoylamino)-1,3-benzothiazol-6-yl]thieno[2,3-b]pyridine-3-carboxamide (C20)

To 1,4-dioxane (10 mL) under N$_2$ were added sequentially C18-1 (64 mg, 0.19 mmol), 4,4,5,5-tetramethyl-2-(4,4,5,5-tetramethyl-1,3,2-dioxaborolan-2-yl)-1,3,2-dioxaborolane (66 mg, 0.26 mmol), potassium acetate (42 mg, 0.43 mmol), Pd(dppf)Cl$_2$ (12 mg, 0.017 mmol). The mixture was stirred under N$_2$ at 100° C. for 5 h. Cooled to room temperature and filtered. To the filtrate were sequentially added B73-1 (48 mg, 0.17 mmol), K$_2$CO$_3$ (59 mg, 0.43 mmol), Pd(dppf)Cl$_2$ (12 mg, 0.017 mmol), and H$_2$O (0.5 mL) under N$_2$. The mixture was stirred at 100° C. under N$_2$ overnight. The mixture was cooled to room temperature, filtered, and the filtrate was concentrated. The residue was purified by silica gel column chromatography (dichloromethane/methanol=50:1) to provide a white solid, which was triturated in EtOAc (15 mL) to give the title compound as a white solid (25 mg, 32%). Its analytic data are shown in Table 1.

Example 21: Compound C21

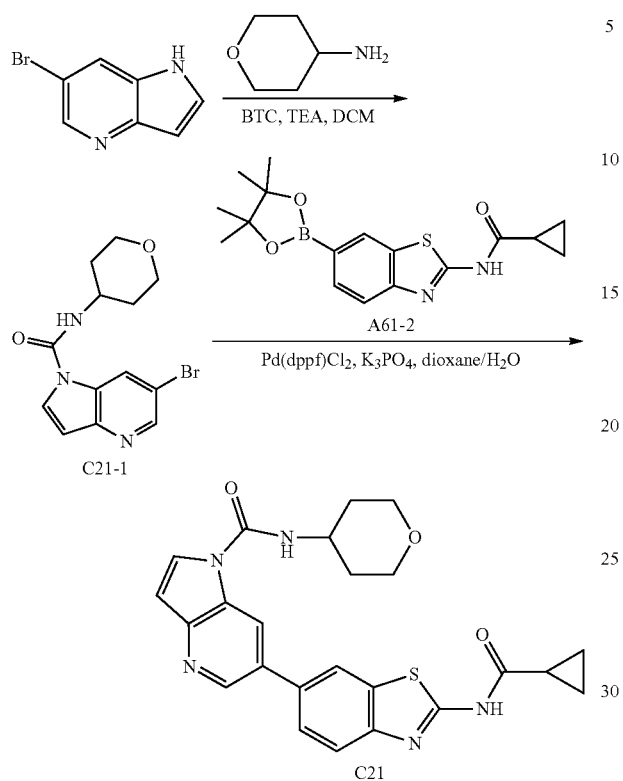

Step 1: 6-bromo-N-tetrahydropyran-4-yl-pyrrolo[3,2-b]pyridine-1-carboxamide; methane (C21-1)

To a solution of 6-bromo-1H-pyrrolo[3,2-b]pyridine (150 mg, 0.76 mmol) and Et₃N in anhydrous CH₂Cl₁₂ (10 mL) under N₂ was added triphosgene (BTC) (90 mg, 0.30 mmol), and the mixture was stirred at room temperature for 2 h. A61-2 (521 mg, 3.80 mmol) was added. After the reaction was complete, the mixture was partitioned between a saturated aqueous NaHCO₃ solution (2 mL) and EtOAc (20 mL). The organic layer was dried over anhydrous Na₂SO₄, filtered, and the filtrate was concentrated. The residue was purified by silica gel column chromatography (EtOAc) to provide the title compound C21-1 as a yellow solid (70 mg, 29%). ¹H NMR (400 MHz, DMSO-d6) δ 8.66 (s, 1H), 8.54 (s, 1H), 8.26-8.23 (m, 2H), 3.92-3.89 (m, 3H), 3.43-3.35 (m, 2H), 1.87-1.83 (m, 2H), 1.65-1.57 (m, 2H).

Step 2: 6-[2-(cyclopropanecarbonylamino)-1,3-benzothiazol-6-yl]-N-tetrahydropyran-4-yl-pyrrolo[3,2-b]pyridine-1-carboxamide (C21)

To 1,4-dioxane were added C21-1 (50 mg, 0.15 mmol), A61-2 (68 mg, 0.23 mmol), tripotassium phosphate trihydrate (101 mg, 0.38 mmol), and Pd(dppf)Cl₂ (22 mg, 0.03 mmol) under N₂. To the mixture at 95° C. under N₂ was added dropwise water (0.5 mL). The mixture was stirred at 95° C. under N₂ overnight. The mixture was cooled to room temperature, filtered, and the filtrate was concentrated. The residue was purified by silica gel column chromatography (dichloromethane/methanol=30:1) to provide a yellow solid, which was triturated in EtOAc/ether (v/v=1:2, 15 mL) to give the title compound C21 as a white solid (15 mg, 22%). Its analytic data are shown in Table 1.

Example 22: Compound C22

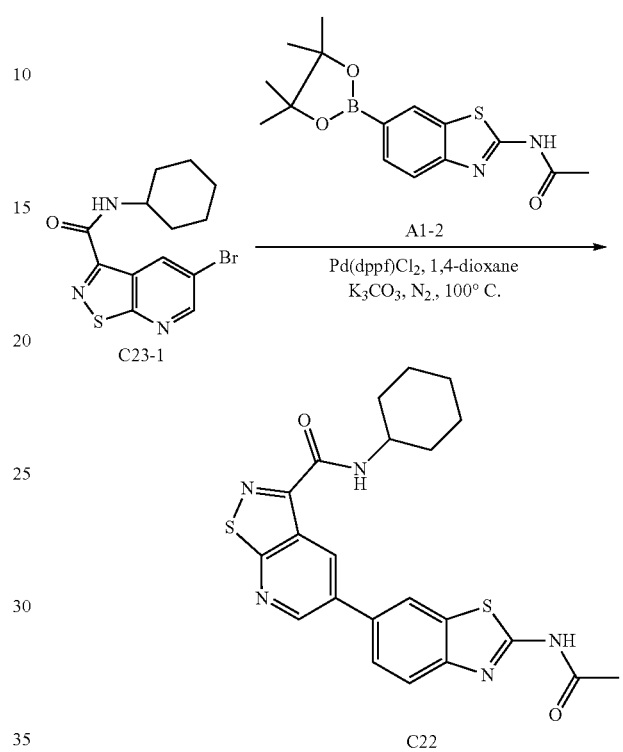

Step 1: 5-(2-acetamido-1,3-benzothiazol-6-yl)-N-cyclohexyl-isothiazolo[5,4-b]pyridine-3-carboxamide (C22)

To 1,4-dioxane (5 mL) were added 5-bromo-N-cyclohexyl-isothiazolo[5,4-b]pyridine-3-carboxamide (C23-1) (80 mg, 0.23 mmol), A1-2 (158 mg, 0.46 mmol), K₂CO₃ (80 mg, 0.58 mmol), water (0.5 mL) and Pd(dppf)Cl₂ (17 mg, 0.02 mmol) under N₂. The mixture was stirred at 80° C. under N₂ overnight. The mixture was cooled to room temperature, filtered, and the filtrate was concentrated. The residue was purified by silica gel column chromatography (dichloromethane/methanol=125:1) to provide the title compound C22 as a white solid (45 mg, 43.4%). Its analytic data are shown in Table 1.

Example 23: Compound C23

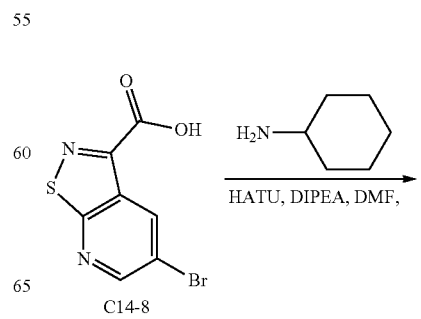

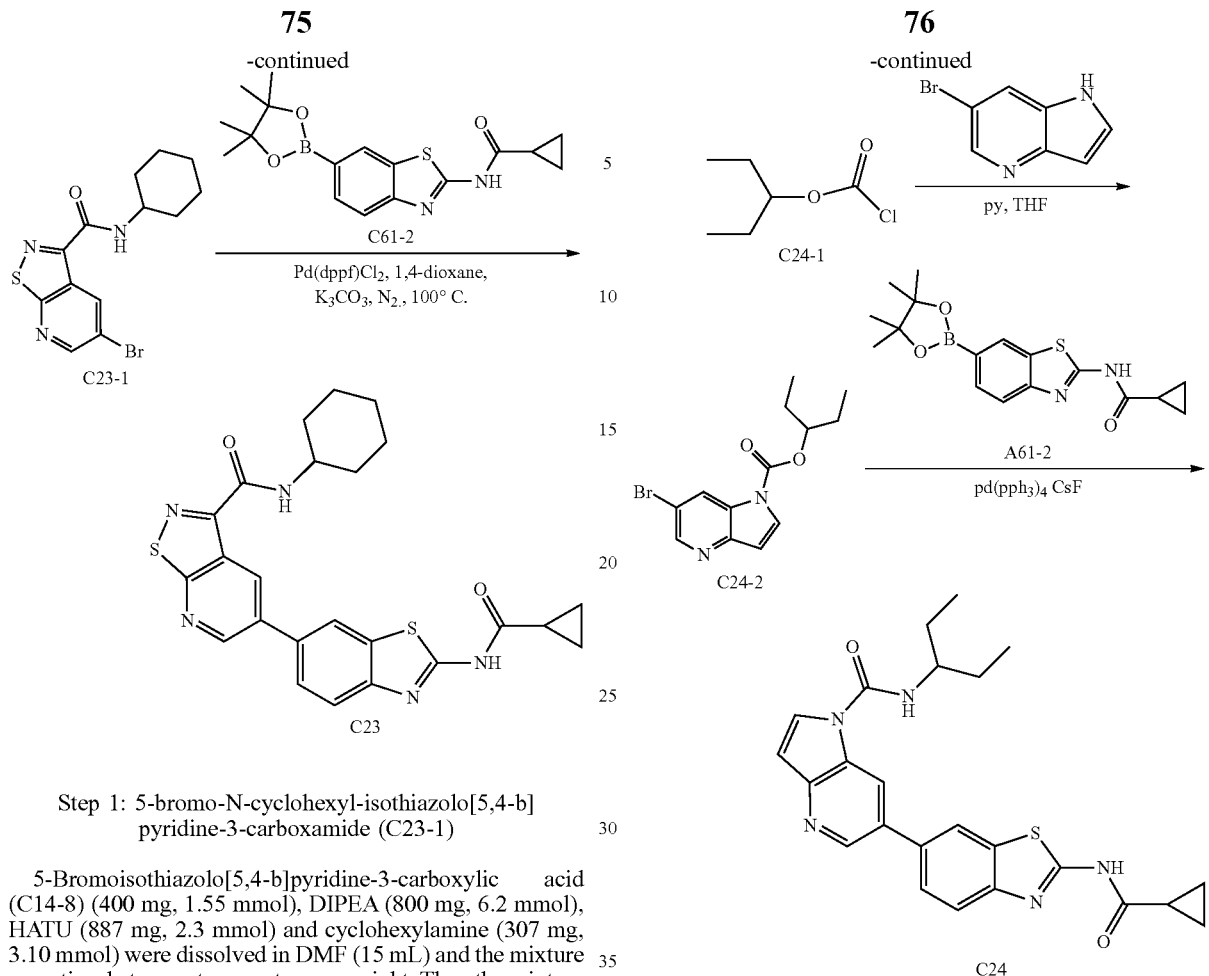

Step 1: 5-bromo-N-cyclohexyl-isothiazolo[5,4-b]pyridine-3-carboxamide (C23-1)

5-Bromoisothiazolo[5,4-b]pyridine-3-carboxylic acid (C14-8) (400 mg, 1.55 mmol), DIPEA (800 mg, 6.2 mmol), HATU (887 mg, 2.3 mmol) and cyclohexylamine (307 mg, 3.10 mmol) were dissolved in DMF (15 mL) and the mixture was stirred at room temperature overnight. Then the mixture was diluted with EtOAc (100 mL), washed with brine (50 mL). The organic layer was separated and concentrated. The residue was purified by silica gel column chromatography (petroleum ether/$CH_2Cl_2$=10:1) to provide the title compound C23-1 as a yellow solid (460 mg, 87.5%). $^1$H NMR (400 MHz, $CDCl_3$) δ 9.40 (s, 1H), 8.81 (s, 1H), 4.05-8.90 (m, 1H), 2.10-2.00 (m, 2H), 1.85-1.75 (m, 2H), 1.70-1.55 (m, 3H), 1.50-1.32 (m, 3H).

Step 2: N-cyclohexyl-5-[2-(cyclopropanecarbonylamino)-1,3-benzothiazol-6-yl]isothiazolo[5,4-b]pyridine-3-carboxamide (C23)

To 1,4-dioxane (5 mL) were added 5-bromo-N-cyclohexyl-isothiazolo[5,4-b]pyridine-3-carboxamide (C23-1) (80 mg, 0.23 mmol), A61-2 (158 mg, 0.46 mmol), $K_2CO_3$ (80 mg, 0.58 mmol), water (0.5 mL), and Pd(dppf)$Cl_2$ (17 mg, 0.02 mmol) under $N_2$. The mixture was stirred at 100° C. under $N_2$ overnight. The mixture was cooled to room temperature, filtered, and the filtrate was concentrated. The residue was purified by silica gel column chromatography (dichloromethane/methanol=50:1) to provide the title compound C23 as a white solid (65 mg, 59.2%). Its analytic data are shown in Table 1.

Example 24: Compound C24

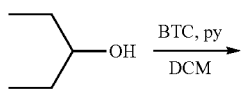

Step 1: 1-ethylpropyl carbonochloridate (C24-1)

A solution of triphosgene (BTC) (268 mg, 0.91 mmol) and pyridine (199 mg, 2.40 mmol) in $CH_2Cl_2$ (5 mL) was stirred at room temperature for 10 min Pentan-3-ol (200 mg, 2.27 mmol) was added to the mixture. After the reaction was complete, the mixture was filtered and the filtrate was concentrated to provide the crude C24-1 (300 mg).

Step 2: 1-ethylpropyl 6-bromopyrrolo[3,2-b]pyridine-1-carboxylate (C24-2)

A solution of 6-bromo-1H-pyrrolo[3,2-b]pyridine (50 mg, 0.25 mmol) and pyridine (122 mg, 0.77 mmol) in THF (5 mL) was added C24-1 (300 mg) in THF via a syringe. After the reaction was complete, the reaction was quenched with a saturated aqueous $NaHCO_3$ solution (2 mL). The mixture was extracted with $CH_2Cl_2$ (10 mL). The organic layer was separated, dried over anhydrous $Na_2SO_4$, filtered, and the filtrate was concentrated to provide the titled compound C24-2 as a yellow solid (80 mg, 95%). $^1$H NMR (400 MHz, $CDCl_3$) δ 8.59 (d, J=1.6 Hz, 1H), 7.84 (d, J=2.8 Hz, 1H), 6.78 (d, J=3.6 Hz, 1H), 5.04-5.01 (m, 2H), 2.17 (s, 1H), 1.18-1.76 (m, 4H), 1.05 (d, J=7.4 Hz, 6H).

Step 3: 1-ethylpropyl 6-[2-(cyclopropanecarbonylamino)-1,3-benzothiazol-6-yl]pyrrolo[3,2-b]pyridine-1-carboxylate (C24)

To 1,4-dioxane (10 mL) and water (1 mL) were added C24-2 (80 mg, 0.26 mmol), A61-2 (133 mg, 0.39 mmol), CsF (137 mg, 0.90 mmol), and Pd(PPh₃)₄ (30 mg, 0.026 mmol) under N₂. The mixture was stirred at 100° C. under N₂ overnight. The mixture was cooled to room temperature, and the filtrate was concentrated. The residue was purified by silica gel column chromatography (dichloromethane/methanol=90:1) to provide the title compound C24 as a white solid (35 mg, 30%). Its analytic data are shown in Table 1.

Example 25: Compound C25

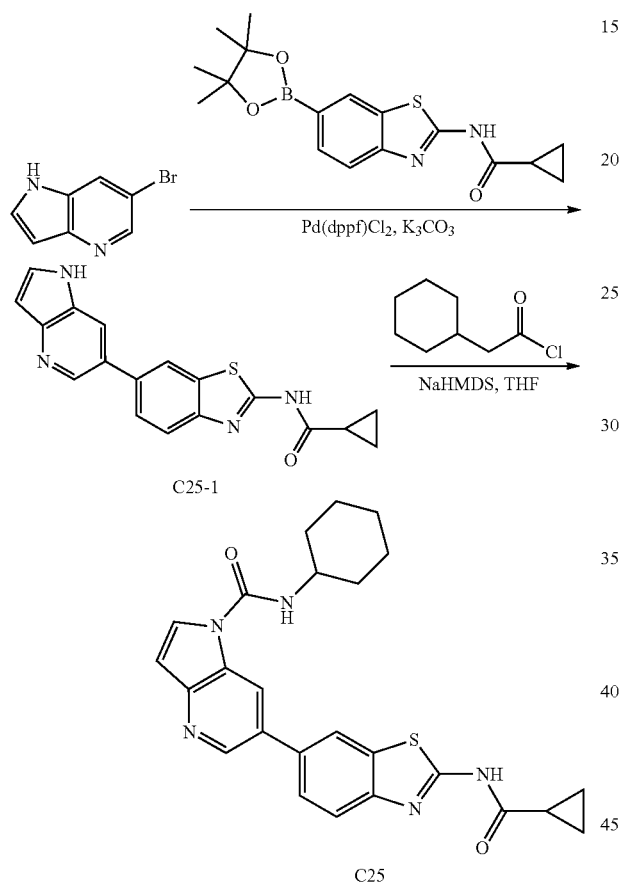

Step 1: A solution of N-[6-(1H-pyrrolo[3,2-b]pyridin-6-yl)-1,3-benzothiazol-2-yl]cyclopropanecarboxamide (C25-1)

A solution of 6-bromo-1H-pyrrolo[3,2-b]pyridine (100 mg, 0.51 mmol), A61-2 (263 mg, 0.77 mmol), K₂CO₃ (176 mg, 1.28 mmol), and Pd(dppf)Cl₂ (37 mg, 0.05 mmol) in 1,4-dioxane (10 mL) was stirred at 100° C. under N₂ overnight. The mixture was cooled to room temperature and concentrated. The residue was purified by silica gel column chromatography (dichloromethane/methanol=40:1) to provide the title compound C25-1 as a white solid (50 mg, 36%). $^1$H NMR (400 MHz, DMSO-d6) δ 12.69 (s, 1H), 11.44 (s, 1H), 8.69 (s, 1H), 8.35 (s, 1H), 8.04 (s, 1H), 7.84-7.78 (m, 2H), 7.69 (s, 1H), 6.59 (s, 1H), 2.02 (s, 1H) 0.96 (s, 4H).

Step 2: N-[6-[1-(2-cyclohexylacetyl)pyrrolo[3,2-b]pyridin-6-yl]-1,3-benzothiazol-2-yl]cyclopropanecarboxamide (C25)

C25-1 (20 mg, 0.21 mmol) was dissolved in re-distilled THF (10 mL) under N₂. A solution of NaHMDS (0.4 mmol, 0.2 mL) was added via a syringe at 0° C. After stirring for 15 min, a solution of 2-cyclohexylacetyl chloride (100 mg, 0.62 mmol) in THF was added via a syringe. After the reaction was complete, the reaction was quenched with aqueous NH₄Cl solution (20 mL). The mixture was extracted with EtOAc (20 mL) and the organic layer was separated, dried over anhydrous Na₂SO₄, filtered, and the filtrate was concentrated. The crude thus obtained was triturated in EtOAc/petroleum ether (v/v=1:3) to give the title compound C25 as a yellow solid (8 mg, 30%). Its analytic data are shown in Table 1.

Example 26: Compound C26

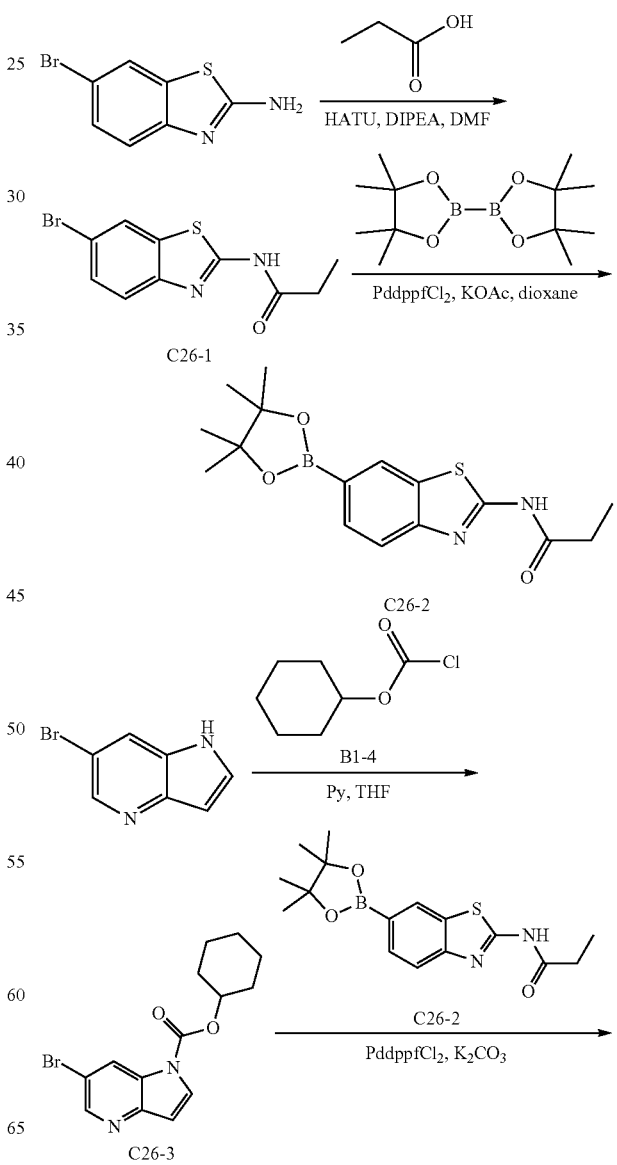

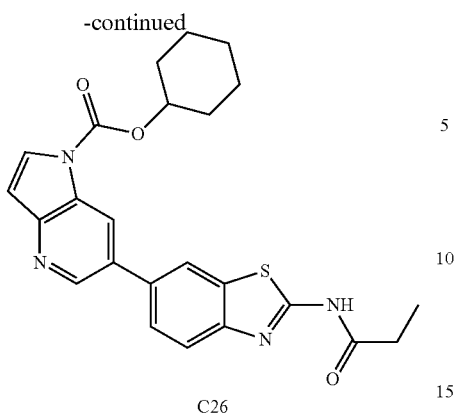

C26

Step 1: N-(6-bromo-1,3-benzothiazol-2-yl)propanamide (C26-1)

A solution of 6-bromo-1,3-benzothiazol-2-amine (1.1 g, 5 mmol), propanoic acid (960 mg, 13 mmol), HATU (5.0 g, 13 mmol) and DIPEA (1.9 g, 15 mmol) in DMF (50 mL) was stirred at 80° C. overnight. The mixture was cooled to room temperature, poured into water, filtered and the filter cake was dried to provide crude title compound C26-1 as a brown solid (1.0 g). $^1$H NMR (400 MHz, DMSO-d6) δ 12.40 (br s, 1H), 8.24 (s, 1H), 7.66 (d, J=8.4 Hz, 1H), 7.55 (d, J=8.4 Hz, 1H), 2.60-2.50 (m, 2H), 1.11 (t, J=7.6 Hz, 3H).

Step 2: N-[6-(4,4,5,5-tetramethyl-1,3,2-dioxaborolan-2-yl)-1,3-benzothiazol-2-yl]propanamide (C26-2)

Into a 100 mL round bottom flask was added sequentially C26-1 (700 mg, 2.5 mmol), 4,5,5-tetramethyl-2-(4,4,5,5-tetramethyl-1,3,2-dioxaborolan-2-yl)-1,3,2-dioxaborolane (927 mg, 3.7 mmol), KOAc (964 mg, 9.8 mmol), Pd(dppf)Cl$_2$ (183 mg, 0.25 mmol) to DMSO (50 mL). The mixture was stirred under N$_2$ at 90° C. for 8 h. Cooled to room temperature and filtered. The filtrate was diluted with EtOAc, and the organic layer was washed with brine, dried, filtered and concentrated. The residue was recrystallized from petroleum ether to provide a light yellow solid (400 mg, 49%). $^1$H NMR (400 MHz, DMSO-d6) δ 12.39 (br s, 1H), 8.26 (s, 1H), 7.71 (s, 2H), 2.58-2.50 (m, 2H), 1.31 (s, 12H), 1.11 (t, J=7.2 Hz, 3H).

Step 3: cyclohexyl 6-bromopyrrolo[3,2-b]pyridine-1-carboxylate (C26-3)

To a solution of 6-bromo-1H-pyrrolo[3,2-b]pyridine (100 mg, 1.03 mmol) and pyridine (489 mg, 3.08 mmol) in THF (5 mL) under N$_2$ was added dropwise cyclohexyl carbonochloridate (B1-4) (500 mg, 3.1 mmol) in THF (2 mL) via a syringe. After the reaction was complete, the mixture was poured in saturated aqueous NaHCO$_3$ (2 mL) and extracted with CH$_2$Cl$_2$ (10 mL). The organic layer was separated, dried, filtered and concentrated. The residue was purified by silica gel column chromatography (petroleum ether/ethyl acetate=5/1) to give the title compound as yellow solid (260 mg, 80%). $^1$H NMR (400 MHz, CDCl$_3$) δ 8.58 (s, 1H), 7.84 (s, 1H), 6.78 (s, 1H), 5.05 (s, 1H), 2.03-1.39 (m, 11H).

Step 4: cyclohexyl 6-[2-(propanoylamino)-1,3-benzothiazol-6-yl]pyrrolo[3,2-b]pyridine-1-carboxylate (C26)

To 1,4-dioxane (10 mL) and water (1 mL) were added C26-3 (100 mg, 0.31 mmol), C26-2 (154 mg, 0.46 mmol), K$_2$CO$_3$ (107 mg, 0.77 mmol), and Pd(dppf)Cl$_2$ (23 mg, 0.038 mmol) under N$_2$. The mixture was stirred at 100° C. under N$_2$ overnight. After the reaction was complete, the mixture was cooled to room temperature and concentrated. The residue was purified by silica gel column chromatography (dichloromethane/methanol=90:1) to provide the title compound C26 as a white solid (35 mg, 25%). Its analytic data are shown in Table 1.

Example 27: Compound C27

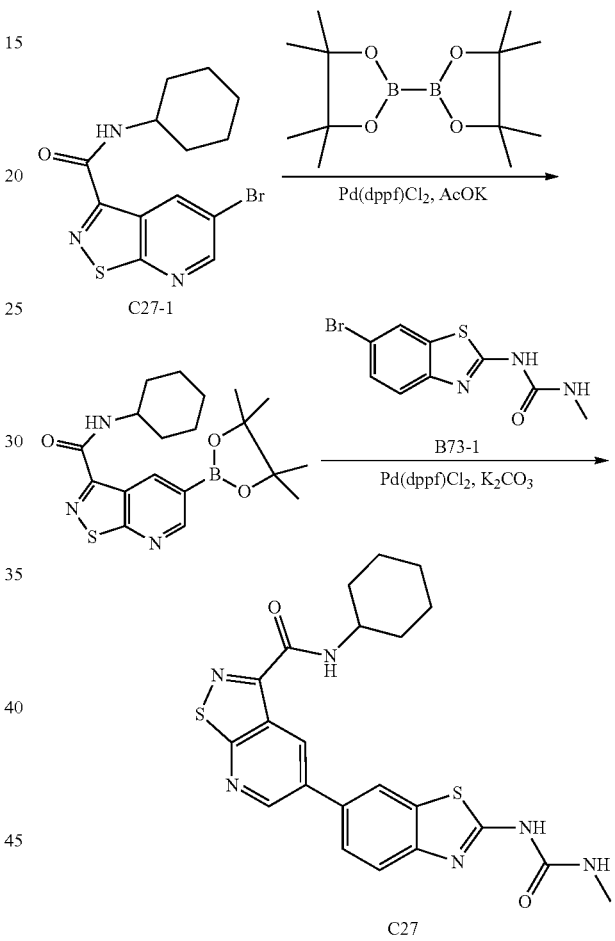

Step 1: N-cyclohexyl-5-[2-(methylcarbamoylamino)-1,3-benzothiazol-6-yl]isothiazolo[5,4-b]pyridine-3-carboxamide (C27)

A solution of 5-bromo-N-cyclohexyl-isothiazolo[5,4-b]pyridine-3-carboxamide (C27-1) (100 mg, 0.30 mmol), 4,5,5-tetramethyl-2-(4,4,5,5-tetramethyl-1,3,2-dioxaborolan-2-yl)-1,3,2-dioxaborolane (127 mg, 0.50 mmol), KOAc (55 mg, 0.56 mmol), Pd(dppf)Cl$_2$ (35 mg, 0.05 mmol) in 1,4-dioxane (50 mL) was stirred under N$_2$ at 100° C. overnight. Cooled to room temperature and K$_2$CO$_3$ (83 mg, 0.60 mmol), water (0.6 mL), B73-1 (44 mg, 0.17 mmol), and Pd(dppf)Cl$_2$ (17 mg, 0.02 mmol) were added to the mixture. Stirred under N$_2$ at 100° C., cooled to room temperature, and concentrated. The residue was purified by silica gel column chromatography (dichloromethane/methanol=50:1) to provide the title compound C27 as a white solid (17 mg, 15.8%). Its analytic data are shown in Table 1.

Example 28: Compound C28

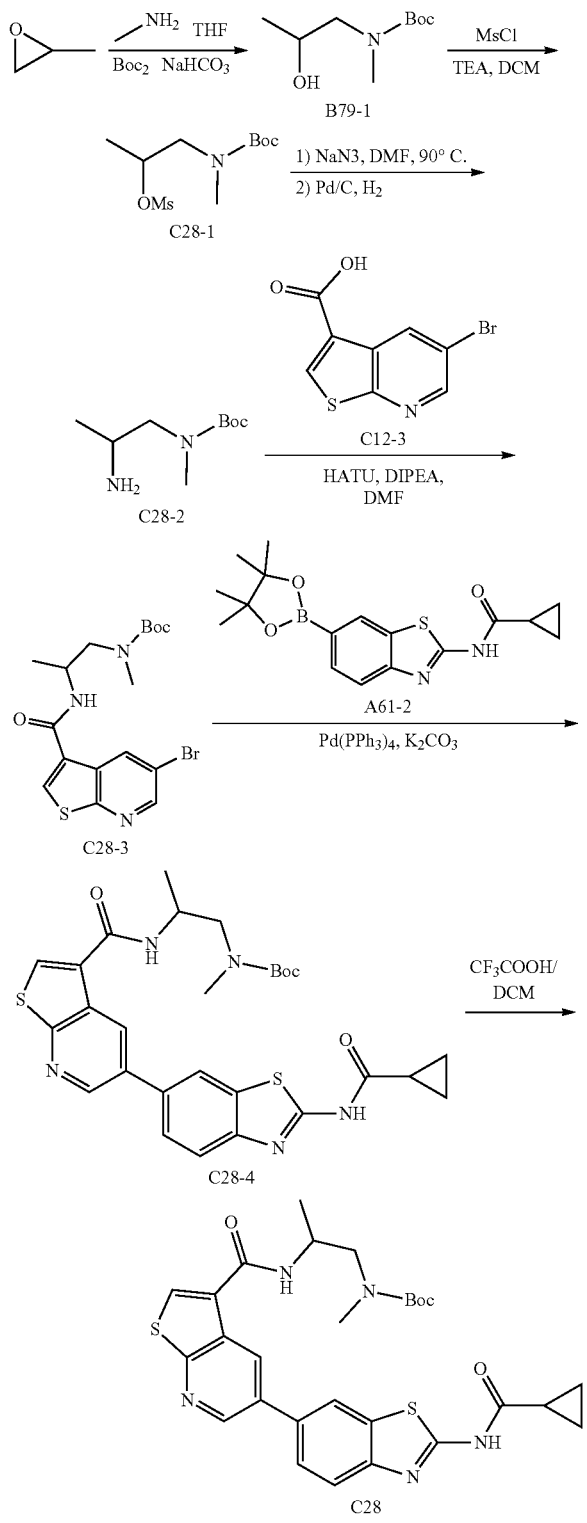

Step 1: tert-butyl N-(2-hydroxypropyl)-N-methyl-carbamate (B79-1)

A solution of 2-methyloxirane (2.5 g, 43 mmol) and 37% methylamine in EtOH (20 mL) were added to anhydrous THF (30 mL) and the resulting mixture was stirred in a sealed tube at 50° C. overnight. The mixture was cooled to room temperature and concentrated. The residue was dissolved in water (50 mL) and the mixture was treated with NaHCO$_3$ (7 g, 86 mmol) and di-tert-butyl dicarbonate (11 g, 52 mmol), then stirred at room temperature for 5 h. The mixture was diluted with water (100 mL) and extracted with EtOAc (50 mL×2). Combined organic layers were dried, filtered and the filtrate was concentrated to provide the title compound B79-1 as a colorless of (4.5 g, 56%). $^1$H NMR (400 MHz, CDCl$_3$) δ 4.07-3.93 (m, 1H), 3.45-3.09 (m, 3H), 2.92 (s, 3H), 1.46 (s, 9H), 1.16 (d, J=6.4 Hz, 3H.

Step 2: [2-[tert-butoxycarbonyl(methyl)amino]-1-methyl-ethyl]methanesulfonate (C28-1)

To a solution of B79-1 (1.9 g, 10 mmol) in CH$_2$Cl$_2$ (50 mL) was added Et$_3$N (3.0 g, 30 mmol) and methanesulfonyl chloride (MsCl) (1.7 g, 1.5 mmol). The mixture was stirred at room temperature for 3 h, quenched with saturated aqueous NaHCO$_3$ (30 mL). The organic layer was separated, washed with brine (40 mL×3), dried, filtered and the filtrate was concentrated to provide crude title product C28-1 as a light yellow oil (1.0 g, 56%). $^1$H NMR (400 MHz, CDCl$_3$) δ 5.03-5.82 (m, 1H), 3.49-3.21 (m, 2H), 2.96 (s, 3H), 2.92 (s, 3H), 1.44 (s, 9H), 1.37 (d, J=6.4 Hz, 3H).

Step 3: tert-butyl N-(2-aminopropyl)-N-methyl-carbamate (C28-2)

To a solution of C28-1 (800 mg, 3 mmol) in DMF (15 mL) was added NaN$_3$ (585 mg, 9 mmol) in portions at room temperature. The mixture was stirred at 90° C. overnight, cooled to room temperature, diluted with EtOAc (100 mL) and brine (50 mL), and stirred for 10 min. The organic layer was separated and washed with brine (50 mL×2), dried, filtered and the filtrate was concentrated to give the crude (400 mg). The crude was dissolved in EtOH (20 mL) and the mixture was hydrogenated over 10% Pd/C (50 mg) under H$_2$ overnight. The mixture was filtered and the filtrate was concentrated to give the crude title compound C28-2 as a colorless oil (250 mg, 44%). $^1$H NMR (400 MHz, CDCl$_3$) δ 4.68-4.57 (m, 1H), 3.20-3.08 (m, 2H), 2.87 (s, 3H), 1.46 (s, 9H), 1.42 (d, J=8.4 Hz, 3H).

Step 4: tert-butyl N-[2-[(5-bromothieno[2,3-b]pyridine-3-carbonyl)amino]propyl]-N-methyl-carbamate (C28-3)

A solution of 5-bromo-3-(tribromomethyl)thieno[2,3-b]pyridine (C12-3) (147 mg, 0.57 mmol) and HATU (342 mg, 0.9 mmol) in DMF was stirred at room temperature for 10 min DIPEA (219 mg, 1.7 mmol) and C28-2 (100 mg, 0.57 mmol) were added to the mixture, which was stirred for 5 h. The mixture was poured into water (50 mL) and extracted with EtOAc (15 mL×2). Combined organic layers were dried, filtered, and the filtrate was concentrated. The residue was purified by silica gel column chromatography (petroleum ether/EtOAc=8:1) to provide the title compound C28-3 as a white solid (200 mg, 60%). $^1$H NMR (400 MHz, CDCl$_3$) δ 9.12 (s, 1H), 8.62 (s, 1H), 8.03 (s, 1H), 7.56 (s, 1H), 4.39-4.22 (m, 1H), 3.88-3.74 (m, 1H), 3.00-2.86 (m, 4H), 1.40 (s, 9H), 1.29 (d, J=6.4 Hz, 3H).

Step 5: tert-butyl N-[2-[[5-[2-(cyclopropanecarbonylamino)-1,3-benzothiazol-6-yl]thieno[2,3-b]pyridine-3-carbonyl]amino]propyl]-N-methyl-carbamate (C28-4)

A solution of C28-3 (65 mg, 0.15 mmol), A61-2 (65 mg, 0.22 mmol), $K_2CO_3$ (52 mg, 0.38 mmol), and Pd(dppf)Cl$_2$ (11 mg, 0.015 mmol) in 1,4-dioxane (8 mL) and water (0.4 mL) was stirred at 100° C. under $N_2$ overnight. The mixture was cooled to room temperature, filtered and the filtrate was concentrated. The residue was purified by silica gel column chromatography (dichloromethane/methanol=100:1) to provide the title compound C28-4 as a yellow solid (65 mg, 77%). $^1$H NMR (400 MHz, CDCl$_3$) δ 11.17 (br s, 1H), 9.19 (s, 1H), 8.89 (s, 1H), 8.15 (s, 1H), 8.10 (s, 1H), 7.84 (d, J=8.4 Hz, 1H), 7.76 (d, J=8.0 Hz, 1H), 7.66 (d, J=5.6 Hz, 1H), 4.53-4.23 (m, 1H), 3.94-3.79 (m, 1H), 3.04-2.86 (m, 4H), 1.85-1.75 (m, 1H), 1.40 (s, 9H), 1.33-1.19 (m, 5H), 1.13-0.94 (m, 2H).

Step 6: 5-[2-(cyclopropanecarbonylamino)-1,3-benzothiazol-6-yl]-N-[1-methyl-2-(methylamino)ethyl]thieno[2,3-b]pyridine-3-carboxamide (C28)

To a solution of C28-4 (65 mg, 0.11 mmol) in CH$_2$Cl$_2$ (10 mL) was added trifluoroactic acid (TFA) (1 mL) dropwise at room temperature. The mixture was stirred overnight. A saturated aqueous NaHCO$_3$ solution was added to the mixture until the pH reaches 8-9 and white precipitates formed. The precipitates were collected by filtration and dried to give the title compound C28 as a white solid (50 mg, 89%). Its analytic data are shown in Table 1.

Example 29: Compound C29

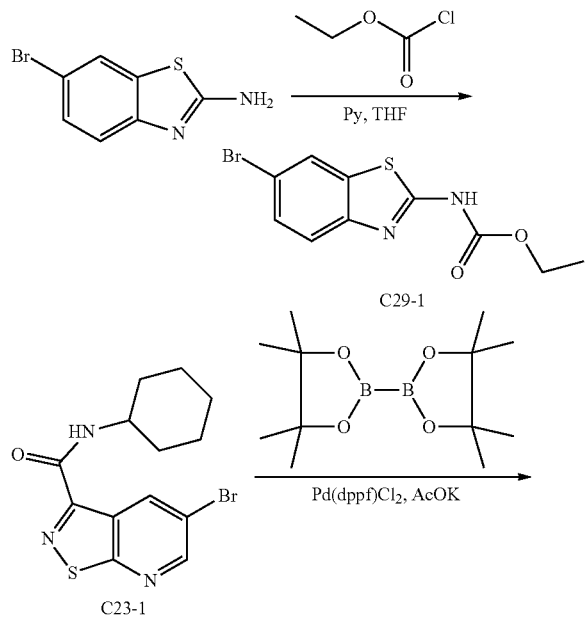

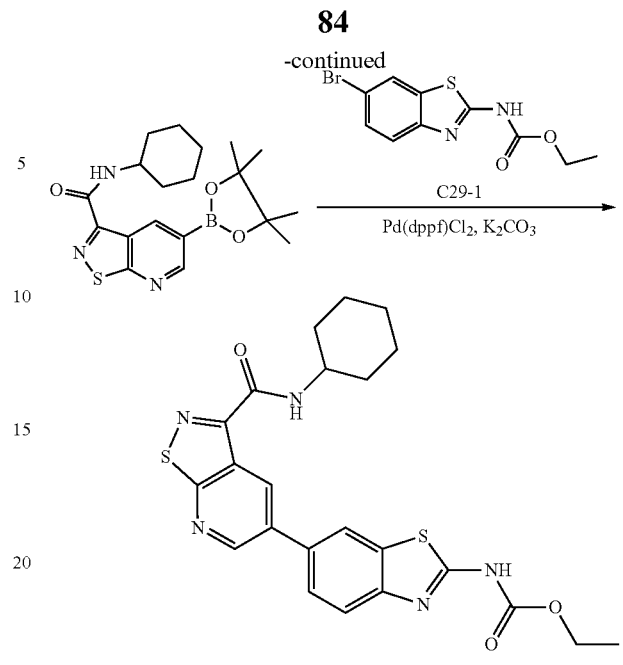

Step 1: ethyl N-(6-bromo-1,3-benzothiazol-2-yl)carbamate (C29-1)

A solution of 6-bromo-1,3-benzothiazol-2-amine (500 mg, 2.19 mmol) and pyridine (400 mg, 4.80 mmol) in THF (5 mL) was added ethyl carbonochloridate (1 g, 9.26 mmol) at 0° C. After the reaction was complete, the mixture was filtered, and the filtrate was triturated with EtOAc (50 mL) to provide the title compound C29-1 as a white solid (500 mg).

Step 2: ethyl N-[6-[3-(cyclohexylcarbamoyl)isothiazolo[5,4-b]pyridin-5-yl]-1,3-benzothiazol-2-yl]carbamate (C29)

A solution of 5-bromo-N-cyclohexyl-isothiazolo[5,4-b]pyridine-3-carboxamide (C23-1) (100 mg, 0.30 mmol), 4,5,5-tetramethyl-2-(4,4,5,5-tetramethyl-1,3,2-dioxaborolan-2-yl)-1,3,2-dioxaborolane (152 mg, 0.60 mmol), KOAc (74 mg, 0.75 mmol), Pd(dppf)Cl$_2$ (22 mg, 0.03 mmol) in 1,4-dioxane (10 mL) was stirred under $N_2$ at 100° C. overnight. Cooled to room temperature and $K_2CO_3$ (104 mg, 0.75 mmol), water (1.0 mL), C29-1 (72 mg, 0.24 mmol), and Pd(dppf)Cl$_2$ (22 mg, 0.03 mmol) were added to the mixture. Stirred under $N_2$ at 80° C. for 6 h, cooled to room temperature, and concentrated. The residue was purified by silica gel column chromatography (dichloromethane/methanol=100:1) to provide the title compound C29 as a white solid (17 mg, 15.8%). Its analytic data are shown in Table 1.

Example 30: Compound C30

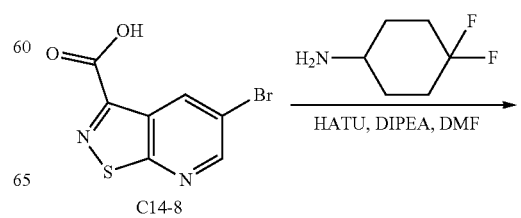

85

-continued

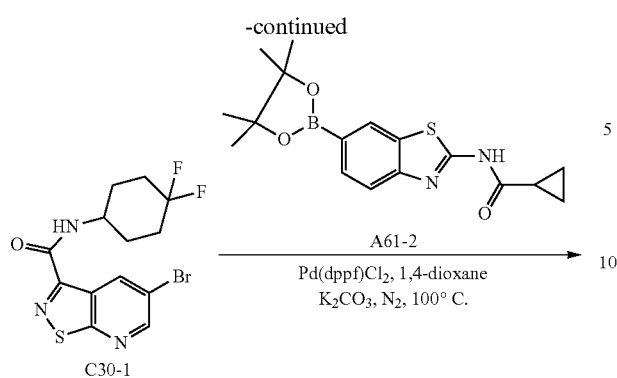

Step 1: 5-bromo-N-(4,4-difluorocyclohexyl)isothiazolo[5,4-b]pyridine-3-carboxamide (C30-1)

A solution of 5-bromoisothiazolo[5,4-b]pyridine-3-carboxylic acid (C14-8) (130 mg, 0.50 mmol), 4,4-difluorocyclohexanamine (135 mg, 1.0 mmol), DIPEA (258 mg, 2.0 mmol) and HATU (285 mg, 0.75 mmol) in DMF (4 mL) was stirred at room temperature overnight.

Partitioned between EtOAc (100 mL) and brine (50 mL). The organic layer was separated and concentrated. The residue was purified by silica gel column chromatography (petroleum ether/EtOAc=50:1) to provide the title compound C30-1 as a yellow solid (120 mg, 64.2%). $^1$H NMR (400 MHz, CDCl$_3$) δ 9.37 (d, J=2.0 Hz, 1H), 8.84 (d, J=2.0 Hz, 1H), 4.20-4.05 (m, 1H), 2.25-2.10 (m, 4H), 2.03-1.90 (m, 2H), 1.80-1.70 (m, 2H).

Step 2: 5-[2-(cyclopropanecarbonylamino)-1,3-benzothiazol-6-yl]-N-(4,4-difluorocyclohexyl)isothiazolo[5,4-b]pyridine-3-carboxamide (C30)

A solution of C30-1 (100 mg, 0.31 mmol), A61-2 (158 mg, 0.46 mmol), K$_2$CO$_3$ (80 mg, 0.58 mmol), water (0.5 mL) and Pd(dppf)Cl$_2$ (17 mg, 0.02 mmol) in 1,4-dioxane (5 mL) under N$_2$ was stirred at 100° C. under N$_2$ overnight. After the reaction was complete, the mixture was cooled to room temperature and concentrated. The residue was purified by silica gel column chromatography (dichloromethane/methanol=50:1) to provide the title compound C30 as a white solid (65 mg, 59.2%). Its analytic data are shown in Table 1.

86

Example 31: Compound C31

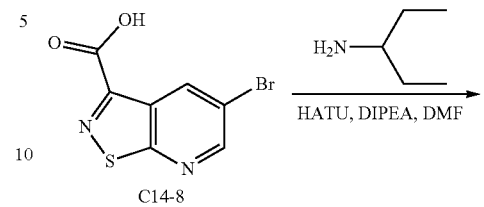

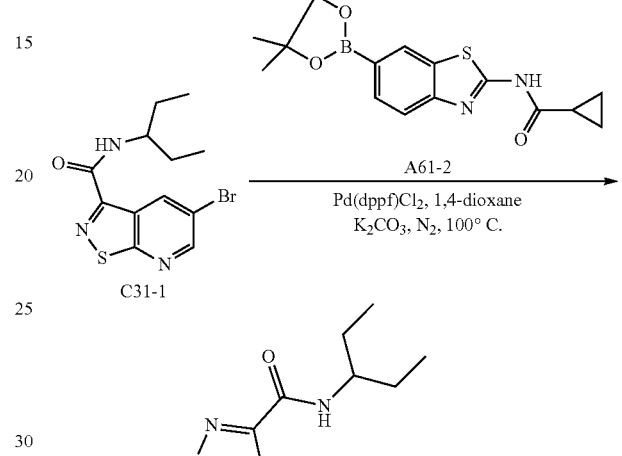

Step 1: 5-bromo-N-(1-ethylpropyl)isothiazolo[5,4-b]pyridine-3-carboxamide (C31-1)

A solution of 5-bromoisothiazolo[5,4-b]pyridine-3-carboxylic acid (C14-8) (130 mg, 0.50 mmol), pentan-3-amine (135 mg, 1.0 mmol), DIPEA (258 mg, 2.0 mmol) and HATU (285 mg, 0.75 mmol) in DMF (4 mL) was stirred at room temperature overnight. Partitioned between EtOAc (100 mL) and brine (50 mL). The organic layer was separated and concentrated. The residue was purified by silica gel column chromatography (petroleum ether/EtOAc=50:1) to provide the title compound C30-1 as a yellow solid (120 mg, 64.2%). $^1$H NMR (400 MHz, CDCl$_3$) δ 8.42 (s, 1H), 8.81 (s, 1H), 77.08 (s, 1H), 4.10-3.96 (m, 1H), 1.78-1.60 (m, 2H), 1.80-1.67 (m, 2H), 1.05-0.96 (m, 6H).

Step 2: 5-[2-(cyclopropanecarbonylamino)-1,3-benzothiazol-6-yl]-N-(1-ethylpropyl)isothiazolo[5,4-b]pyridine-3-carboxamide (C31)

A solution of C31-1 (120 mg, 0.37 mmol), A61-2 (255 mg, 0.74 mmol), K$_2$CO$_3$ (127 mg, 0.92 mmol), water (0.6 mL) and Pd(dppf)Cl$_2$ (29 mg, 0.04 mmol) in 1,4-dioxane (6 mL) under N$_2$ was stirred at 80° C. under N$_2$ overnight. After the reaction was complete, the mixture was cooled to room temperature and concentrated. The residue was purified by silica gel column chromatography (dichloromethane/methanol=125:1) to provide the title compound C30 as a white solid (65 mg, 37.8%). Its analytic data are shown in Table 1.

Example 32: Compound C32

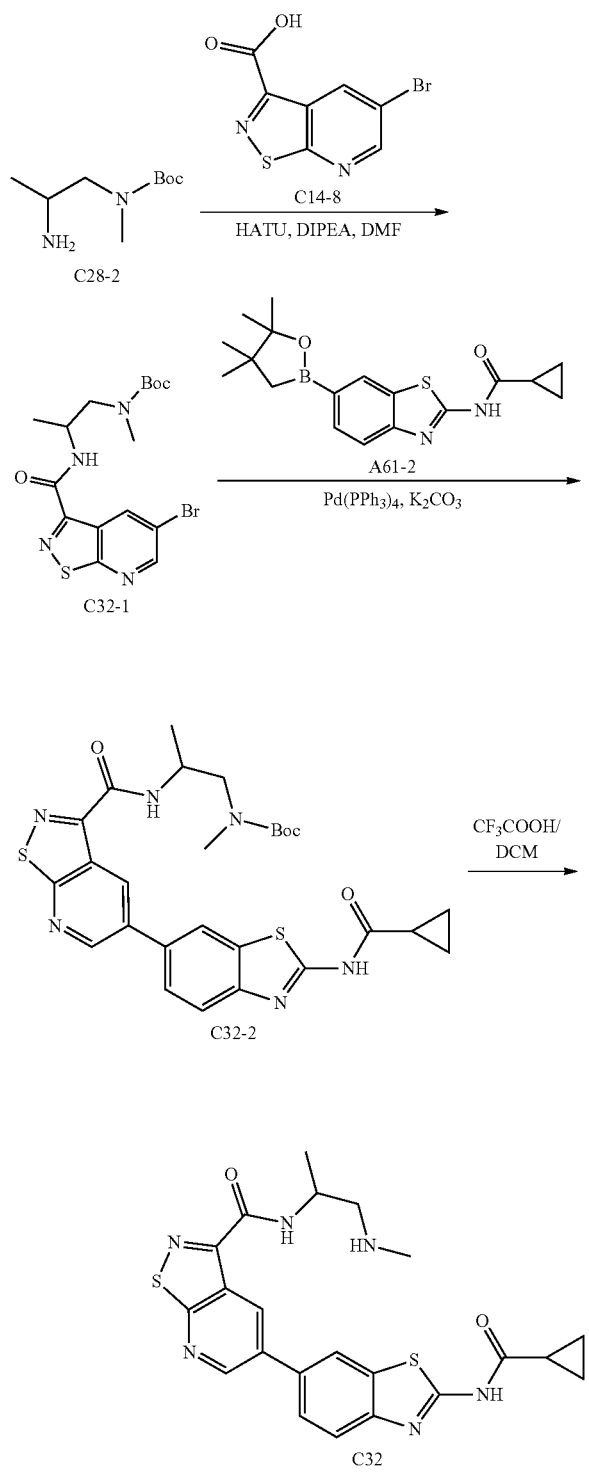

Step 1: tert-butyl N-[2-[(5-bromoisothiazolo[5,4-b]pyridine-3-carbonyl)amino]propyl]-N-methyl-carbamate (C32-1)

A solution of 5-bromoisothiazolo[5,4-b]pyridine-3-carboxylic acid (C14-8) (130 mg, 0.50 mmol) and HATU (190 mg, 0.50 mmol) in DMF (10 mL) was stirred at room temperature for 10 min. DIPEA (98 mg, 0.76 mmol) and C28-2 (73 mg, 0.42 mmol) were added to the mixture, which was stirred for 5 h. The mixture was poured into water (50 mL) and extracted with EtOAc (15 mL×2). Combined organic layers were dried, filtered, and the filtrate was concentrated. The residue was purified by silica gel column chromatography (petroleum ether/EtOAc=10:1) to provide the title compound C32-1 as a white solid (60 mg, 28%).

Step 2: tert-butyl N-[2-[[5-[2-(cyclopropanecarbonylamino)-1,3-benzothiazol-6-yl]isothiazolo[5,4-b]pyridine-3-carbonyl]amino]propyl]-N-methyl-carbamate (C32-2)

A solution of C32-1 (60 mg, 0.14 mmol), A61-2 (62 mg, 0.21 mmol), $K_2CO_3$ (48 mg, 0.35 mmol), and $Pd(dppf)Cl_2$ (11 mg, 0.015 mmol) in 1,4-dioxane (8 mL) and water (0.4 mL) was stirred at 100° C. under $N_2$ overnight. The mixture was cooled to room temperature, filtered and the filtrate was concentrated. The residue was purified by silica gel column chromatography (dichloromethane/methanol=150:1) to provide the title compound C32-2 as a yellow solid (28 mg, 35%). $^1$H NMR (400 MHz, $CDCl_3$) δ 10.70 (br s, 1H), 9.44 (s, 1H), 9.08 (s, 1H), 8.15 (s, 1H), 8.12-8.04 (m, 2H), 7.92-7.84 (m, 1H), 7.79-7.73 (m, 1H), 4.51-4.32 (m, 1H), 3.94-3.61 (m, 2H), 2.94 (d, J=11.2 Hz, 3H), 1.49 (s, 4H), 1.37 (s, 5H), 1.32 (d, J=6.0 Hz, 3H), 1.09-1.00 (m, 3H), 0.91-0.83 (m, 1H).

Step 3: 5-[2-(cyclopropanecarbonylamino)-1,3-benzothiazol-6-yl]-N-[1-methyl-2-(methylamino)ethyl]isothiazolo[5,4-b]pyridine-3-carboxamide (C32)

To a solution of C32-2 (28 mg, 0.05 mmol) in $CH_2Cl_2$ (10 mL) was added trifluoroactic acid (TFA) (0.5 mL) dropwise at room temperature. The mixture was stirred overnight. A saturated aqueous $NaHCO_3$ solution was added to the mixture until the pH reaches 8-9 and white precipitates formed. The precipitates were collected by filtration. The collected precipitates were purified by silica gel column chromatography (dichloromethane/methanol=10:1) to provide give the title compound C32 (12 mg, 52%). Its analytic data are shown in Table 1.

Example 33: Compound C33

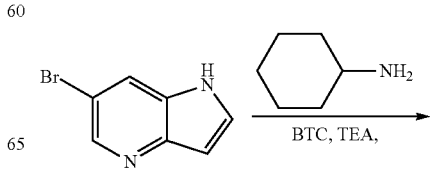

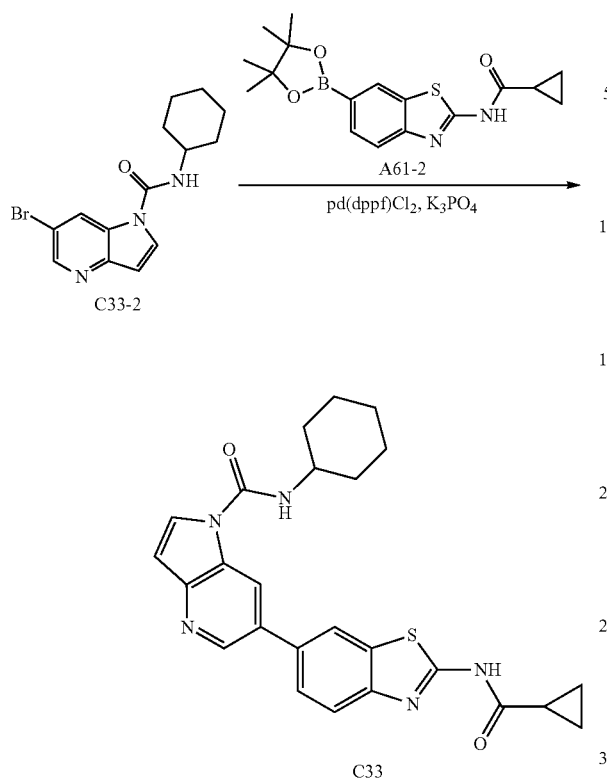

Example 34: Compound C34

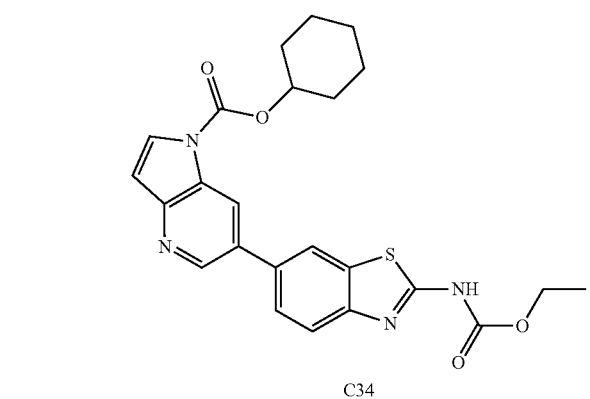

Step 1: 6-bromo-N-cyclohexyl-pyrrolo[3,2-b]pyridine-1-carboxamide (C33-2)

To a solution of 6-bromo-1H-pyrrolo[3,2-b]pyridine (200 mg, 1.03 mmol) and Et₃N in anhydrous CH₂Cl₂ (5 mL) under N₂ was added BTC (122 mg, 0.41 mmol). The mixture was stirred at room temperature for 4 h and cyclohexanamine (505 mg, 5.1 mmol) was added. When the reaction was complete, the mixture was partitioned between saturated aqueous NaHCO₃ (15 mL) and EtOAc (10 mL). The organic layer was separated, dried, and concentrated. The residue was purified by silica gel column chromatography (petroleum ether/EtOAc=1:1) to provide the title compound C33-2 as a yellow solid (150 mg, 60%). $^1$H NMR (400 MHz, CDCl₃) δ 8.73 (s, 1H), 8.57 (s, 1H), 7.63 (s, 1H), 6.80 (s, 1H), 3.25-3.23 (m, 1H), 2.11-1.13 (m, 10H).

Step 2: N-cyclohexyl-6-[2-(cyclopropanecarbonylamino)-1,3-benzothiazol-6-yl]pyrrolo[3,2-b]pyridine-1-carboxamide (C33)

To 1,4-dioxane/H₂O (10 mL/1 mL) under N₂ were added C33-2 (60 mg, 0.19 mmol), A61-2 (96 mg, 0.28 mmol), tripotassium phosphate trihydrate (77 mg, 0.56 mmol), and Pd(dppf)Cl₂ (14 mg, 0.02 mmol) under N₂. The mixture was stirred at 100° C. under N₂ overnight. The mixture was cooled to room temperature, and concentrated. The residue was purified by silica gel column chromatography (dichloromethane/methanol=90:1) to afford the title compound C33 as a a white solid (20 mg, 23%). Its analytic data are shown in Table 1.

Step 1: cyclohexyl 6-(4,4,5,5-tetramethyl-1,3,2-dioxaborolan-2-yl)pyrrolo[3,2-b]pyridine-1-carboxylate (C34-1)

A solution of cyclohexyl 6-bromopyrrolo[3,2-b]pyridine-1-carboxylate (C15-2) (100 mg, 0.31 mmol), 4,4,4',4',5,5,5',5'-octamethyl-2,2'-bi-1,3,2-dioxaborolane (158 mg, 0.62 mmol), potassium acetate (76 mg, 0.77 mmol), Pd(dppf)Cl₂ (23 mg, 0.03 mmol) in 1,4-dioxane (10 mL) was stirred at 90° C. overnight. After the reaction was complete, the mixture was used as is in the next step.

Step 2: cyclohexyl 6-[2-(ethoxycarbonylamino)-1,3-benzothiazol-6-yl]pyrrolo[3,2-b]pyridine-1-carboxylate (C34)

To the mixture obtained in Step 1 was added ethyl N-(6-bromo-1,3-benzothiazol-2-yl)carbamate (C29-1) (62 mg, 0.21 mmol), K₂CO₃ (85 mg, 0.62 mmol), Pd(dppf)Cl₂ (15 mg, 0.02 mmol), and water (1 mL). The resulting mixture was stirred at 100° C. under N₂ overnight. The mixture was cooled to room temperature and concentrated. The residue was purified by silica gel column chromatography (dichloromethane/methanol=100:1) to provide the title compound C34 as a white solid (25 mg, 25%). Its analytic data are shown in Table 1.

Example 35: Compound C35

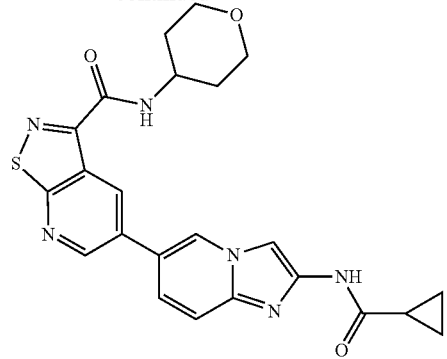

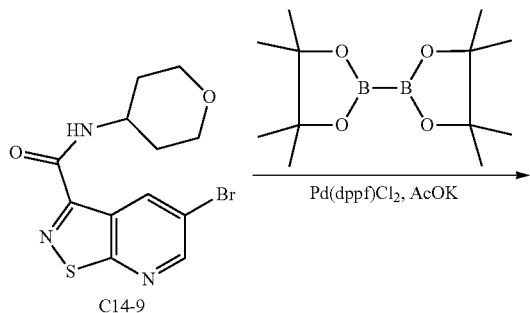

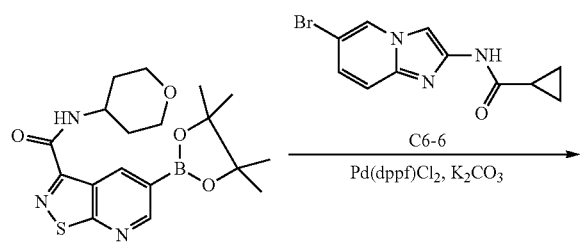

Step 1: 5-[2-(cyclopropanecarbonylamino)imidazo[1,2-a]pyridin-6-yl]-N-tetrahydropyran-4-yl-isothiazolo[5,4-b]pyridine-3-carboxamide (C35)

A solution of 5-bromo-N-tetrahydropyran-4-yl-isothiazolo[5,4-b]pyridine-3-carboxamide (C14-9) (120 mg, 0.35 mmol), 4,4,4',4',5,5,5',5'-octamethyl-2,2'-bi-1,3,2-dioxaborolane (237 mg, 0.70 mmol), potassium acetate (86 mg, 0.88 mmol), Pd(dppf)Cl₂ (29 mg, 0.04 mmol) in 1,4-dioxane (10 mL) was stirred at 100° C. overnight. After the reaction was complete, the mixture was cooled to room temperature and was charged with K₂CO₃ (120 mg, 0.87 mmol), Pd(dppf)Cl₂ (22 mg, 0.03 mmol), N-(6-bromoimidazo[1,2-a]pyridin-2-yl)cyclopropanecarboxamide (C6-6) (68 mg, 0.24 mmol), and water (0.9 mL). The resulting mixture was stirred at 80° C. under N₂ for 8 h. The mixture was cooled to room temperature and concentrated. The residue was purified by silica gel column chromatography (dichloromethane/methanol=100:1) to provide the title compound C35 as a white solid (37 mg, 15.8%). Its analytic data are shown in Table 1.

Example 36: Compound C36

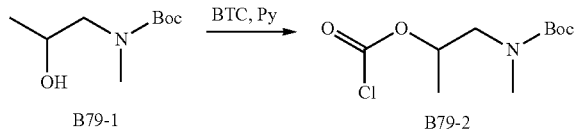

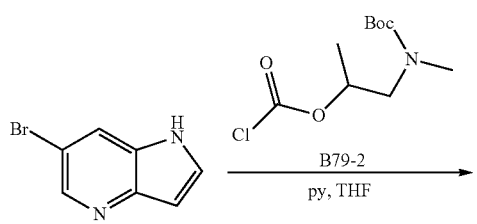

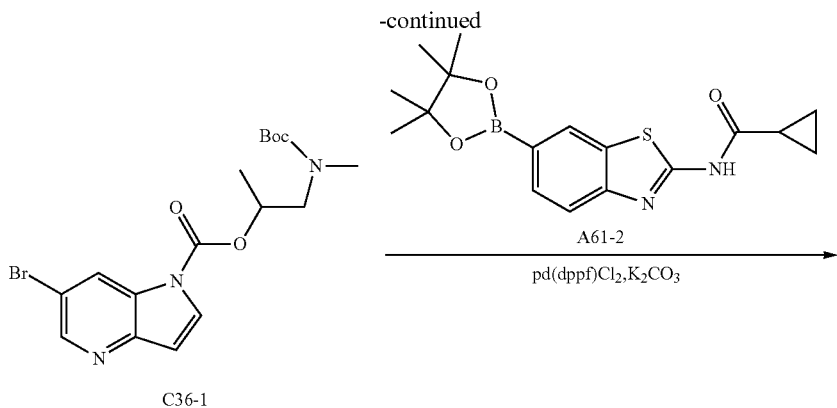

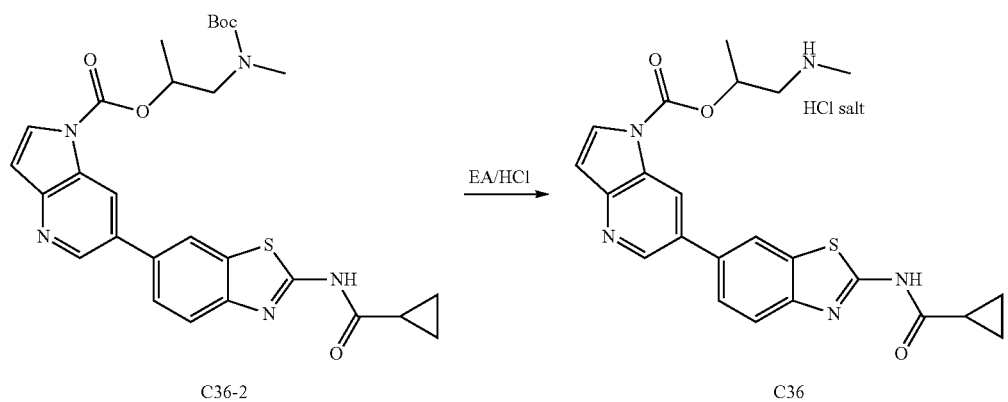

Step 1: [2-[tert-butoxycarbonyl(methyl)amino]-1-methyl-ethyl]carbonochloridate (B-79-2)

To a solution of tert-butyl N-(2-hydroxypropyl)-N-methyl-carbamate (B79-1) (950 mg, 5 mmol) in CH$_2$Cl$_2$ (50 mL) was added pyridine (514 mg, 6.5 mmol), followed by dropwise addition of triphosgene (BTC) (592 g, 2 mmol) in CH$_2$Cl$_2$ (5 mL). The mixture was stirred at room temperature for 2 h. The mixture was filtered and the filtrate was concentrated. The residue was stirred in EtOAc (30 mL), then filtered again. The filtrate was concentrated to provide the title compound B79-2 as a colorless oil (930 mg, 74%), directly used in the next step.

Step 2: [2-[tert-butoxycarbonyl(methyl)amino]-1-methyl-ethyl] 6-bromopyrrolo[3,2-b]pyridine-1-carboxylate (C36-1)

To a solution of 6-bromo-1H-pyrrolo[3,2-b]pyridine (200 mg, 1.03 mmol) and pyridine (122 mg, 0.77 mmol) in THF (5 mL) under N$_2$ was added slowly B79-2 (500 mg, 2 mmol) via a syringe. After the reaction was complete, partitioned between saturated aqueous NaHCO$_3$ solution and CH$_2$Cl$_2$ (5 mL). The organic layer was separated, dried over anhydrous Na$_2$SO$_4$, filtered and the filtrate was concentrated. The residue purified by silica gel column chromatography (petroleum ether/EtOAc=5:1) to provide the title compound C36-1 as a white solid (260 mg, 80%). $^1$H NMR (400 MHz, CDCl$_3$)$^1$H NMR (400 MHz, CDCl$_3$) δ 8.67 (s, 1H), 8.59 (s, 1H), 7.86-7.80 (m, 1H), 6.78 (s, 1H), 5.36 (s, 1H), 3.61-3.39 (m, 1H), 3.37-3.19 (m, 1H), 2.96-2.92 (m, 3H), 1.45-1.36 (m, 12H).

Step 3: [2-[tert-butoxycarbonyl(methyl)amino]-1-methyl-ethyl] 6-[2-(cyclopropanecarbonylamino)-1,3-benzothiazol-6-yl]pyrrolo[3,2-b]pyridine-1-carboxylate (C36-2)

A solution of C36-1 (200 mg, 0.49 mmol), A61-2 (251 mg, 0.73 mmol), K$_2$CO$_3$ (168 mg, 1.22 mmol), and Pd(dppf)Cl$_2$ (36 mg, 0.05 mmol) in 1,4-dioxane (10 mL) and water (1 mL) was stirred at 100° C. under N$_2$ overnight. After the reaction was complete, the mixture was cooled to room temperature, and the filtrate was concentrated. The residue was purified by silica gel column chromatography (dichloromethane/methanol=100:1) to provide the title compound C36-2 as a white solid (130 mg, 49%).

Step 4: [1-methyl-2-(methylamino)ethyl] 6-[2-(cyclopropanecarbonylamino)-1,3-benzothiazol-6-yl] pyrrolo[3,2-b]pyridine-1-carboxylate, hydrochloride salt (C36)

To a solution of C36-2 (20 mg, 0.036 mmol) in EtOAc (1 mL) was added HCl/EtOAc (1 mL). When the reaction was complete, more EtOAc (3 mL) was added and the mixture was filtered to provide the title compound C36 as a yellow solid. Its analytic data are shown in Table 1.

Example 37: Compound C37

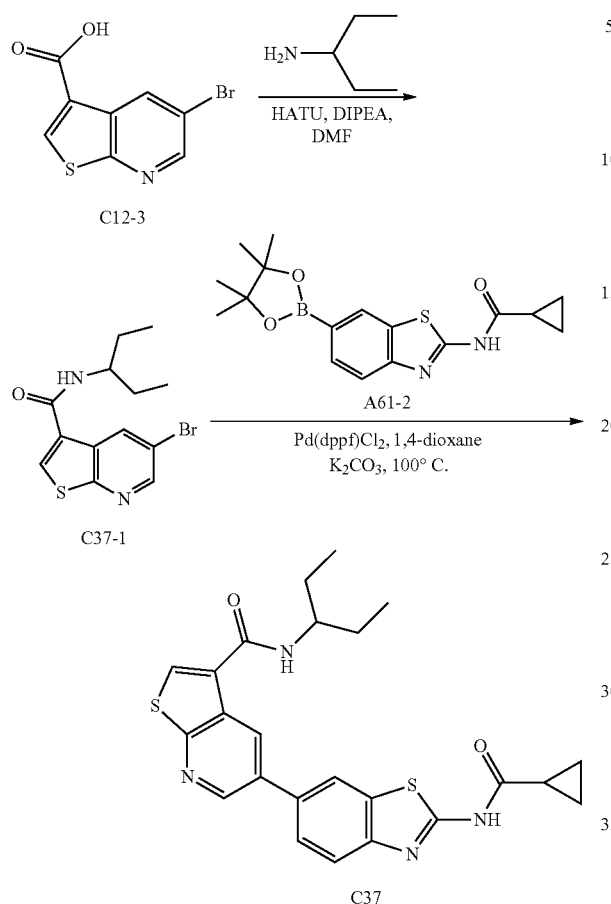

Step 1: 5-bromo-N-(1-ethylpropyl)thieno[2,3-b]pyridine-3-carboxamide (C37-1)

A solution of 5-bromothieno[2,3-b]pyridine-3-carboxylic acid (C37-1) (110 mg, 0.42 mmol), DIPEA (108 mg, 0.84 mmol), HATU (239 mg, 0.63 mmol), and pentan-3-amine (73 mg, 0.84 mmol) in DMF (4 mL) was stirred at room temperature overnight. The mixture was diluted with EtOAc (100 mL), and washed with brine (35 mL). The organic layer was separated, dried, filtered, and the filtrate was concentrated. The was purified by silica gel column chromatography (petroleum/$CH_2Cl_2$=1:1) to provide the title compound C37-1 as a yellow solid (100 mg, 73%). $^1$H NMR (400 MHz, $CDCl_3$) δ 8.96 (s, 1H), 8.65 (s, 1H), 7.88 (s, 1H), 5.75-5.65 (m, 1H), 4.15-3.90 (m, 1H), 1.80-1.65 (m, 2H), 1.55-1.45 (m, 2H), 1.05-0.93 (m, 6H).

Step 2: 5-[2-(cyclopropanecarbonylamino)-1,3-benzothiazol-6-yl]-N-(1-ethylpropyl)thieno[2,3-b]pyridine-3-carboxamide (C37)

A solution of C37-1 (100 mg, 0.31 mmol), A61-2 (213 mg, 0.62 mmol), $K_2CO_3$ (108 mg, 0.78 mmol), and Pd(dppf)$Cl_2$ (25 mg, 0.03 mmol) in 1,4-dioxane (5 mL) and water (0.5 mL) was stirred at 100° C. under $N_2$ overnight. After the reaction was complete, the mixture was cooled to room temperature, and the filtrate was concentrated. The residue was purified by silica gel column chromatography (dichloromethane/methanol=50:1) to provide the title compound C37 as a white solid (37 mg, 26.7%). Its analytic data are shown in Table 1.

Example 38: Compound C38

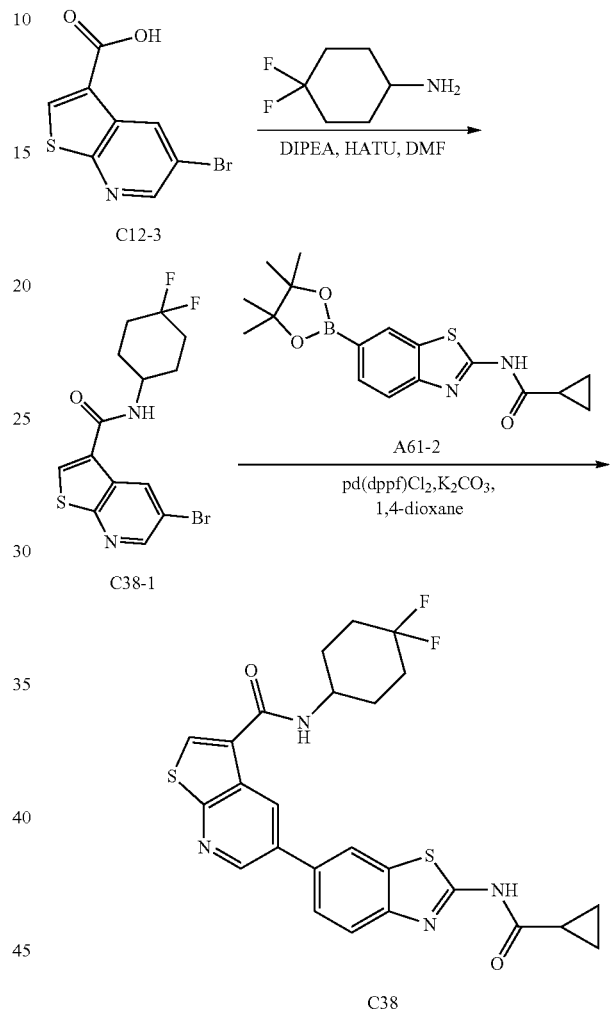

Step 1: 5-bromo-N-(4,4-difluorocyclohexyl)thieno[2,3-b]pyridine-3-carboxamide (C38-1)

A solution of 5-bromothieno[2,3-b]pyridine-3-carboxylic acid (C12-3) (80 mg, 0.31 mmol) and HATU (178 mg, 0.47 mmol) in DMF (5 mL) was stirred for 15 min. To the mixture were added DIPEA (120 mg, 0.93 mmol) and 4,4-difluorocyclohexanamine (80 mg, 0.47 mmol). The mixture was stirred at room temperature overnight, poured into a saturated aqueous $NaHCO_3$ solution, and extracted with $CH_2Cl_2$ (10 mL). The organic layer was separated, washed with brine (10 mL×2), dried over anhydrous $Na_2SO_4$, filtered, and the filtrate was concentrated to provide the title compound C38-1 a yellow solid (110 mg, 95%). $^1$H NMR (400 MHz, $CDCl_3$) δ 8.93 (s, 1H), 8.66 (s, 1H), 7.90 (s, 1H), 5.88 (s, 1H), 4.13 (s, 1H), 2.16 (d, J=8.8 Hz, 4H), 2.01-1.90 (m, 2H), 1.69-1.58 (m, 2H).

Step 2: 5-[2-(cyclopropanecarbonylamino)-1,3-benzothiazol-6-yl]-N-(4,4-difluorocyclohexyl)thieno[2,3-b]pyridine-3-carboxamide (C38)

A solution of C38-1 (110 mg, 0.29 mmol), A61-2 (151 mg, 0.44 mmol), K₂CO₃ (121 mg, 0.88 mmol), and Pd(dppf)Cl₂ (21 mg, 0.03 mmol) in 1,4-dioxane (10 mL) and water (1 mL) was stirred at 100° C. under N₂ overnight. After the reaction was complete, the mixture was cooled to room temperature, filtered, and the filtrate was concentrated. The residue was purified by silica gel column chromatography (dichloromethane/methanol=50:1) to provide the title compound C38 as a white solid (15 mg, 23%). Its analytic data are shown in Table 1.

Example 39: Compound 39

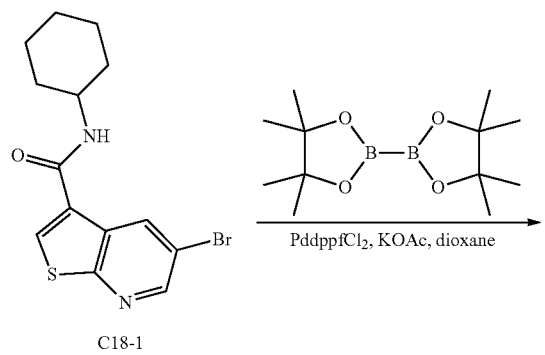

Step 1: N-cyclohexyl-5-(4,4,5,5-tetramethyl-1,3,2-dioxaborolan-2-yl)thieno[2,3-b]pyridine-3-carboxamide (C39-1)

To anhydrous 1,4-dioxane were added 5-bromo-N-cyclohexyl-thieno[2,3-b]pyridine-3-carboxamide (C18-1) (180 mmol), 4,4,4',4',5,5,5',5'-octamethyl-2,2'-bi-1,3,2-dioxaborolane (200 mg, 0.80 mmol), potassium acetate (127 mg, 1.3 mmol), Pd(dppf)Cl₂ (38 mg, 0.053 mmol). The mixture was stirred at 100° C. under N₂ overnight. After the reaction was complete, the mixture was cooled to room temperature and concentrated. The residue was purified by silica gel column chromatography (petroleum ether/EtOAc=3:1) to provide the title compound C39-1 as a white solid (200 mg, 98%).

Step 2: ethyl N-[6-[3-(cyclohexylcarbamoyl)thieno[2,3-b]pyridin-5-yl]-1,3-benzothiazol-2-yl]carbamate (C39)

A suspension of C39-1 (78 mg, 0.2 mmol), A29-1 (30 mg, 0.1 mmol), K₂CO₃ (35 mg, 0.25 mmol), and Pd(dppf)Cl₂ (7 mg, 0.01 mmol) in 1,4-dioxane (5 mL) and water (0.3 mL) was stirred at 100° C. under N₂ overnight. After the reaction was complete, the mixture was cooled to room temperature, poured into water (30 mL) and filtered. The solids collected from the filtration was dissolved in 6 N HCl (10 mL) and CH₂Cl₂ (10 mL), and stirred at room temperature for 10 min. The mixture was filtered and the filtrate was allowed to settle. The aqueous layer was separated, washed by CH₂Cl₂ (5 mL×3), then its pH was adjusted to pH 7-8 by adding aqueous NaOH solution (6 N), and filtered. The solids collected were added to EtOH (5 mL) and triturated at 70° C. for 30 min, then cooled to room temperature, filtered to provide the title compound C39 as a white solid (12 mg, 25%). Its analytic data are shown in Table 1.

Example 40: Compound C40

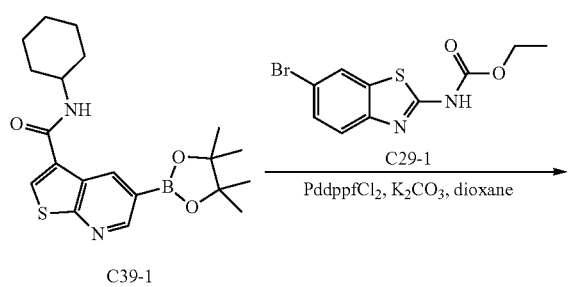

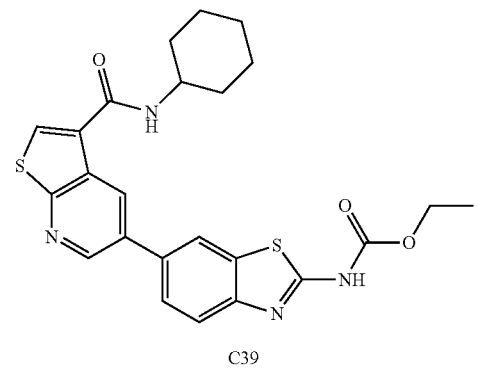

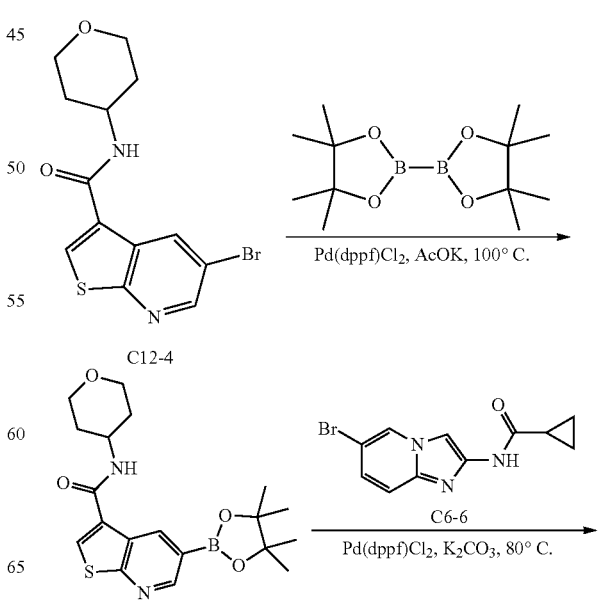

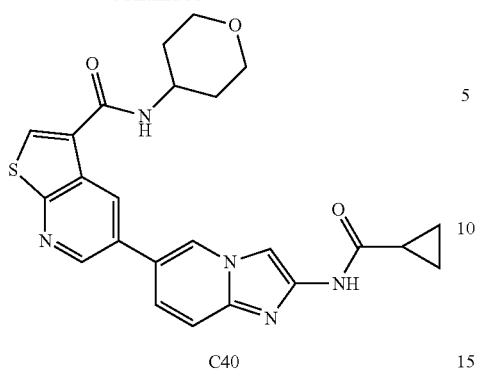

C40

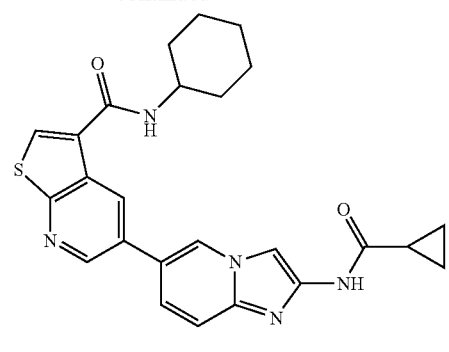

C41

Step 1: 5-[2-(cyclopropanecarbonylamino)imidazo[1,2-a]pyridin-6-yl]-N-tetrahydropyran-4-yl-thieno[2,3-b]pyridine-3-carboxamide (C40)

A solution of 5-bromo-N-tetrahydropyran-4-yl-thieno[2,3-b]pyridine-3-carboxamide (C12-4) (140 mg, 0.41 mmol), 4,4,4',4',5,5,5',5'-octamethyl-2,2'-bi-1,3,2-dioxaborolane (208 mg, 0.82 mmol), potassium acetate (98 mg, 1.0 mmol), Pd(dppf)Cl$_2$ (29 mg, 0.04 mmol) in 1,4-dioxane (10 mL) was stirred at 100° C. overnight. After the reaction was complete, the mixture was cooled to room temperature and was charged with K$_2$CO$_3$ (120 mg, 0.87 mmol), Pd(dppf)Cl$_2$ (22 mg, 0.03 mmol), N-(6-bromoimidazo[1,2-a]pyridin-2-yl)cyclopropanecarboxamide (C6-6) (68 mg, 0.24 mmol), and water (0.9 mL). The resulting mixture was stirred at 80° C. under N$_2$ for 8 h. The mixture was cooled to room temperature and concentrated. The residue was purified by silica gel column chromatography (dichloromethane/methanol=50:1) to provide the title compound C40 as a white solid (40 mg, 15.8%). Its analytic data are shown in Table 1.

Example 41: Compound C41

Step 1: N-cyclohexyl-5-[2-(cyclopropanecarbonylamino)imidazo[1,2-a]pyridin-6-yl]thieno[2,3-b]pyridine-3-carboxamide (C41)

A solution of 5-bromo-N-cyclohexyl-thieno[2,3-b]pyridine-3-carboxamide (C18-1) (133 mg, 0.39 mmol), 4,4,4',4',5,5,5',5'-octamethyl-2,2'-bi-1,3,2-dioxaborolane (198 mg, 0.78 mmol), potassium acetate (95 mg, 0.97 mmol), Pd(dppf)Cl$_2$ (29 mg, 0.04 mmol) in 1,4-dioxane (5 mL) was stirred at 100° C. overnight. After the reaction was complete, the mixture was cooled to room temperature and was charged with tripotassium phosphate trihydrate (258 mg, 0.97 mmol), Pd(dppf)Cl$_2$ (29 mg, 0.04 mmol), N-(6-bromoimidazo[1,2-a]pyridin-2-yl)cyclopropanecarboxamide (C6-6) (75 mg, 0.27 mmol), and water (0.4 mL). The resulting mixture was stirred at 80° C. under N$_2$ for 8 h. The mixture was cooled to room temperature and concentrated. The residue was purified by silica gel column chromatography (dichloromethane/methanol=50:1) to provide the title compound C41 as a white solid (40 mg, 15.8%). Its analytic data are shown in Table 1.

Example 42: Compound C42

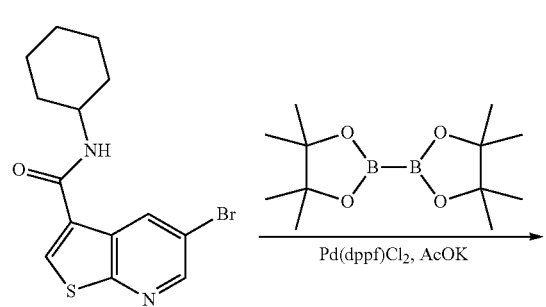

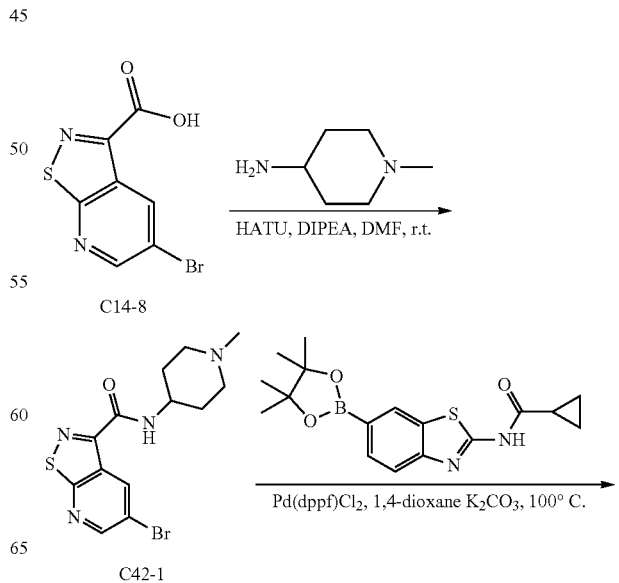

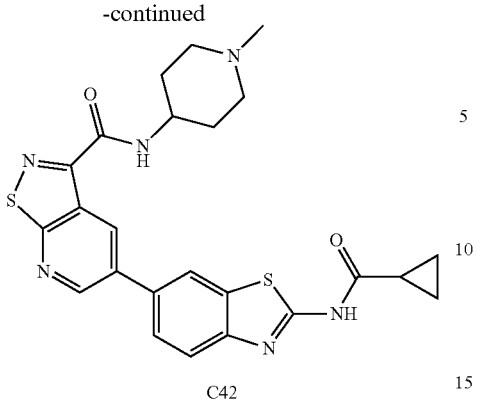

C42

Step 1: 5-bromo-N-(1-methylpiperidin-4-yl)isothiazolo[5,4-b]pyridine-3-carboxamide (C42-1)

A solution of 5-bromoisothiazolo[5,4-b]pyridine-3-carboxylic acid (C14-8) (100 mg, 0.39 mmol), DIPEA (138 mg, 1.07 mmol), HATU (74 mg, 0.77 mmol), and 1-methylpiperidin-4-amine (64 mg, 0.58 mmol) in DMF (5 mL) was stirred at room temperature overnight. The mixture was diluted with ethyl acetate (50 mL), and washed with brine (35 mL×5). The organic layer was separated, dried, filtered, and the filtrate was concentrated. The residue was purified by silica gel column chromatography (petroleum/ethyl acetate=3:1) to provide the compound C42-1 as a yellow solid (100 mg, 73%). $^1$H NMR (400 MHz, CDCl$_3$) δ 9.36 (s, 1H), 8.81 (s, 1H), 4.09-3.92 (m, 1H), 3.04-2.80 (m, 2H), 2.38 (s, 3H), 2.32-2.20 (m, 2H), 2.15-2.00 (m, 2H), 1.81-1.73 (m, 2H).

Step 2: 5-(2-(cyclopropanecarboxamido)benzo[d]thiazol-6-yl)-N-(1-methylpiperidin-4-yl)isothiazolo[5,4-b]pyridine-3-carboxamide (C42)

A solution of C42-1 (100 mg, 0.28 mmol), A61-2 (110 mg, 0.43 mmol), K$_2$CO$_3$ (120 mg, 0.85 mmol), and Pd(dppf)Cl$_2$ (25 mg, 0.03 mmol) in 1,4-dioxane (5 mL) and water (0.5 mL) was stirred at 100° C. under N$_2$ overnight. After the reaction was complete, the mixture was cooled to room temperature, and the filtrate was concentrated. The residue was purified by silica gel column chromatography (dichloromethane/methanol=20:1) to provide the title compound C42 as a white solid (10 mg, 23%). Its analytic data are shown in Table 1.

Example 43: Compound C43

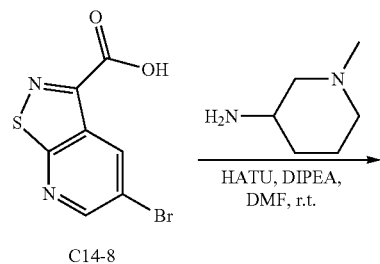

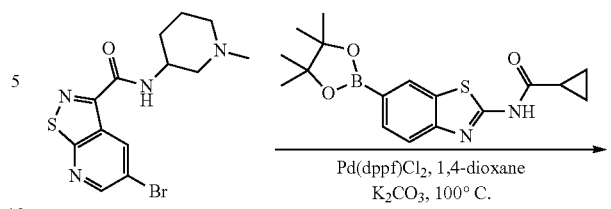

C43

Step 1: 5-bromo-N-(1-methylpiperidin-3-yl)isothiazolo[5,4-b]pyridine-3-carboxamide (C43-1)

A solution of 5-bromoisothiazolo[5,4-b]pyridine-3-carboxylic acid (C14-8) (80 mg, 0.26 mmol), DIPEA (130 mg, 1.00 mmol), HATU (80 mg, 0.21 mmol), and 1-methylpiperidin-3-amine (50 mg, 0.44 mmol) in DMF (5 mL) was stirred at room temperature overnight. The mixture was diluted with ethyl acetate (50 mL), and washed with brine (35 mL×5). The organic layer was separated and concentrated to provide the crude compound C43-1 as a yellow solid (70 mg, 64%). MS (ESI/APCI) m/z 354.7 [M+H]$^+$.

Step 2: 5-(2-(cyclopropanecarboxamido)benzo[d]thiazol-6-yl)-N-(1-methylpiperidin-3-yl)isothiazolo[5,4-b]pyridine-3-carboxamide (C43)

A solution of C43-1 (70 mg, 0.20 mmol), A61-2 (102 mg, 0.30 mmol), K$_2$CO$_3$ (81 mg, 0.59 mmol), and Pd(dppf)Cl$_2$ (25 mg, 0.03 mmol) in 1,4-dioxane (5 mL) and water (0.5 mL) was stirred at 100° C. under N$_2$ overnight. After the reaction was complete, the mixture was cooled to room temperature, and the filtrate was concentrated. The residue was purified by silica gel column chromatography (dichloromethane/methanol=20:1) to provide the title compound C43 as a white solid (10 mg, 23%). Its analytic data are shown in Table 1.

TABLE 1

Selected compounds synthesized

| Compd. No. | Structure | ¹H NMR and LC-MS |
|---|---|---|
| C1 | 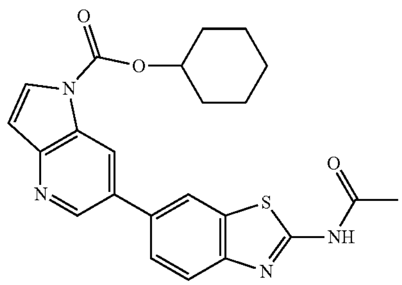 [SMILES: CC(=O)Nc1nc2ccc(-c3cnc4ccn(C(=O)OC5CCCCC5)c4c3)cc2s1] | ¹H NMR (400 MHz, DMSO-$d_6$) δ 12.43 (s, 1H), 8.88 (s, 1H), 8.60 (s, 1H), 8.38 (s, 1H), 8.07 (d, J = 3.6 Hz, 1H) 7.86 (d, J = 8.4 Hz, 1H), 7.77 (d, J = 8.4 Hz, 1H), 6.91 (d, J= 3.6 Hz, 1H), 5.11-5.00 (m, 1H), 2.22 (s, 3H), 2.05-1.92 (m, 2H), 1.84-1.65 (m, 4H), 1.58-1.32 (m, 4H). LC-MS (m/z): 434.8 [M + H]⁺. |
| C2 | 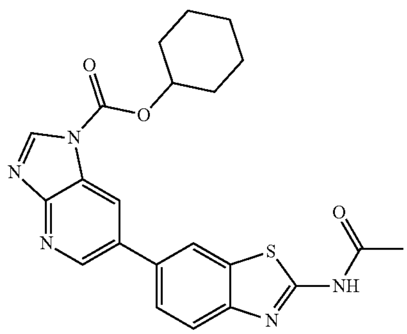 [SMILES: CC(=O)Nc1nc2ccc(-c3cnc4ncn(C(=O)OC5CCCCC5)c4c3)cc2s1] | ¹H NMR (400 MHz, DMSO-$d_6$) δ 12.45 (br s, 1H), 9.02 (s, 1H), 8.91 (s, 1H), 8.50 (s, 1H), 8.40 (s, 1H), 7.87 (d, J = 8.0 Hz, 1H), 7.79 (d, J = 6.8 Hz, 1H), 5.17-5.01 (m, 1H), 2.22 (s, 3H), 2.09-1.89 (m, 2H), 1.87-1.65 (m, 4H), 1.59-1.29 (m, 4H). LC-MS (m/z): 435.7 [M + H]⁺. |
| C3 | 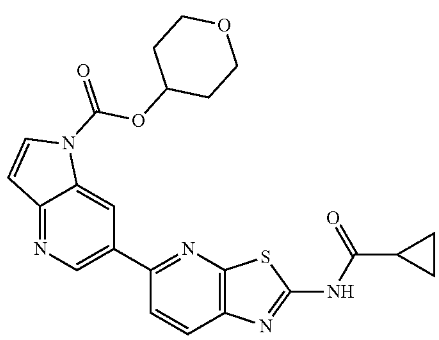 [SMILES: O=C(Nc1nc2ccc(-c3cnc4ccn(C(=O)OC5CCOCC5)c4c3)nc2s1)C1CC1] | ¹H NMR (400 MHz, DMSO-$d_6$) δ 12.86 (s, 1H), 9.26 (s, 1H), 9.14 (s, 1H), 8.25-8.17 (m, 2H), 8.15 (d, J = 3.6 Hz, 1H), 6.93 (d, J = 3.6 Hz, 1H), 5.33-5.21 (m, 1H), 4.03-3.86 (m, 2H), 3.72-3.54 (m, 2H), 2.17-1.99 (m, 3H), 1.93-1.77 (m, 2H), 1.07-0.91 (m, 4H). LC-MS (m/z): 463.7 [M + H]⁺. |
| C4 | 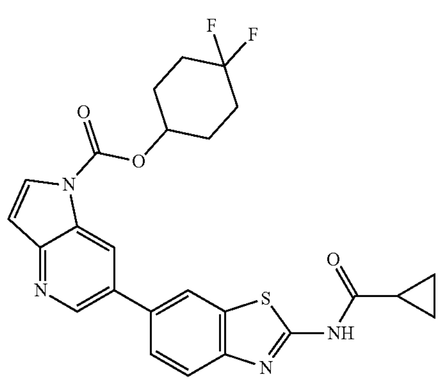 [SMILES: O=C(Nc1nc2ccc(-c3cnc4ccn(C(=O)OC5CCC(F)(F)CC5)c4c3)cc2s1)C1CC1] | ¹H NMR (400 MHz, DMSO-$d_6$) δ 12.74 (s, 1H), 8.89 (s, 1H), 8.58 (s, 1H), 8.37 (s, 1H), 8.17 (s, 1H), 7.85 (d, J = 8.0 Hz, 1H), 7.78 (d, J = 8.0 Hz, 1H), 8.92 (s, 1H), 5.25 (s, 1H), 2.19-1.93 (m, 9H), 0.99 (s, 4H). LC-MS (m/z): 496.7 [M + H]⁺. |

TABLE 1-continued

Selected compounds synthesized

| Compd. No. | Structure | ¹H NMR and LC-MS |
|---|---|---|
| C5 | 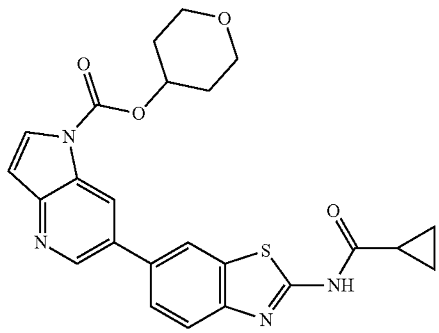 [SMILES: O=C(Nc1nc2ccc(-c3cnc4ccn(C(=O)OC5CCOCC5)c4c3)cc2s1)C1CC1] | ¹H NMR (400 MHz, DMSO-$d_6$) δ 12.74 (s, 1H), 8.88 (s, 1H), 8.60 (s, 1H), 8.39 (s, 1H), 8.11 (d, J = 3.2 Hz, 1H), 7.87 (d, J = 8.4 Hz, 1H), 7.78 (d, J = 8.8 Hz, 1H), 6.92 (d, J = 3.2 Hz, 1H), 5.27-5.17 (m, 1H), 3.98-3.81 (m, 2H), 3.58 (t, J = 8.8 Hz, 2H), 2.14-1.96 (m, 3H), 1.93-1.75 (m, 2H), 1.03-0.89 (m, 4H). LC-MS (m/z): 462.7 [M + H]$^+$. |
| C6 | 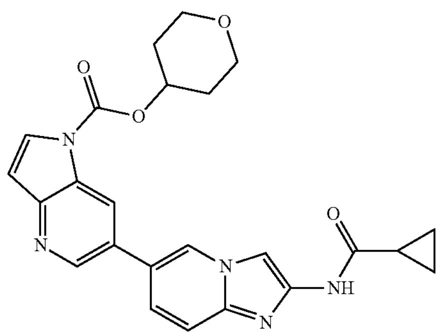 | ¹H NMR (400 MHz, DMSO-$d_6$) δ 11.03 (s, 1H), 9.02 (s, 1H), 8.85 (s, 1H), 8.57 (s, 1H), 8.14 (s, 2H), 7.65-7.49 (m, 2H), 6.93 (d, J = 3.2 Hz, 1H), 5.29-5.16 (m, 1H), 4.00-3.80 (m, 2H), 3.58 (t, J = 8.8 Hz, 2H), 2.16-2.02 (m, 2H), 2.02-1.90 (m, 1H), 1.90-1.76 (m, 2H), 0.90-0.73 (m, 4H). LC-MS (m/z): 445.7 [M + H]$^+$. |
| C7 | 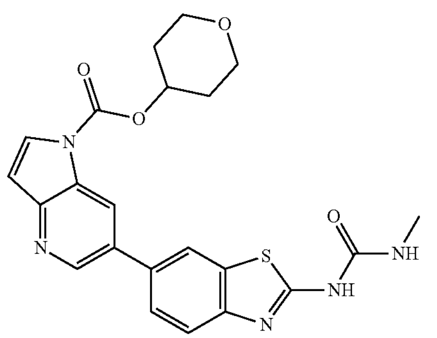 [SMILES: CNC(=O)Nc1nc2ccc(-c3cnc4ccn(C(=O)OC5CCOCC5)c4c3)cc2s1] | ¹H NMR (400 MHz, DMSO-$d_6$) δ 10.91 (s, 1H), 8.87 (s, 1H), 8.58 (s, 1H), 8.30 (s, 1H), 8.10 (d, J = 3.2 Hz, 1H), 7.79-7.64 (m, 2H), 6.91 (d, J = 3.2 Hz, 1H), 6.66 (s, 1H), 5.29-5.16 (m, 1H), 3.96-3.82 (m, 2H), 3.58 (t, J = 8.8 Hz, 2H), 2.73 (d, J = 4.0 Hz, 3H), 2.16-2.00 (m, 2H), 1.95-1.72 (m, 2H). LC-MS (m/z): 451.7 [M + H]$^+$. |
| C8 | 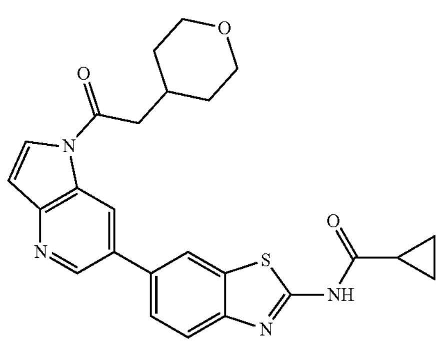 [SMILES: O=C(Nc1nc2ccc(-c3cnc4ccn(C(=O)CC5CCOCC5)c4c3)cc2s1)C1CC1] | ¹H NMR (400 MHz, DMSO-d6) δ 12.73 (s, 1H), 8.88 (s, 2H), 8.39 (s, 1H), 8.32 (s, 1H), 7.86-7.78 (m, 2H), 6.92 (s, 1H), 3.85 (d, J = 9.6 Hz, 2H), 3.05 (d, J = 12.8 Hz, 2H), 2.15 (s, 2H), 2.02 (s, 1H), 1.70 (d, J = 12.8 Hz, 2H), 1.36-1.34 (m, 2H), 1.23 (s, 1H), 0.97 (s, 4H). LC-MS (m/z): 460.7 [M + H]$^+$ |

TABLE 1-continued

Selected compounds synthesized

| Compd. No. | Structure | ¹H NMR and LC-MS |
|---|---|---|
| C9 | 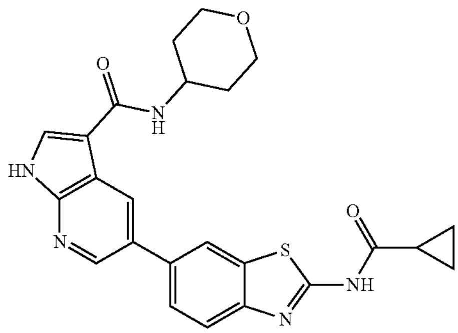 [SMILES: O=C(NC1CCOCC1)c1c[nH]c2ncc(-c3ccc4nc(NC(=O)C5CC5)sc4c3)cc12] | ¹H NMR (400 MHz, DMSO-$d_6$) δ 12.70 (s, 1H), 12.17 (s, 1H), 8.70 (s, 1H), 8.62 (s, 1H), 8.32 (s, 1H), 8.24 (s, 1H), 7.93 (d, J = 7.6 Hz, 1H), 7.84 (d, J = 8.4 Hz, 1H), 7.75 (d, J = 8.4 Hz, 1H), 4.08-3.98 (m, 1H), 3.94-3.84 (m, 2H), 3.44-3.40 (m, 2H), 2.07-1.97 (m, 1H), 1.88-1.76 (m, 2H), 1.66-1.51 (m, 2H), 1.06-0.87 (m, 4H). LC-MS (m/z): 461.7 [M + H]⁺. |
| C10 | 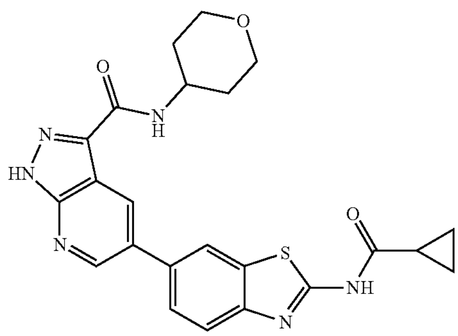 [SMILES: O=C(NC1CCOCC1)c1n[nH]c2ncc(-c3ccc4nc(NC(=O)C5CC5)sc4c3)cc12] | ¹H NMR (400 MHz, DMSO-$d_6$) δ 14.26 (s, 1H), 12.73 (s, 1H), 8.97 (d, J = 2.4 Hz, 1H), 8.72 (d, J = 2.0 Hz, 1H), 8.50 (d, J = 8.0 Hz, 1H), 8.40 (d, J = 2.0 Hz, 1H), 7.86 (d, J = 8.4 Hz, 1H), 7.81 (dd, J = 8.0, 2.0 Hz, 1H), 4.15-4.03 (m, 1H), 3.94-3.84 (m, 2H), 3.44-3.40 (m, 2H), 2.07-1.97 (m, 1H), 1.80-1.65 (m, 4H), 1.04-0.91 (m, 4H). LC-MS (m/z): 484.6 [M + Na]⁺. |
| C11 | 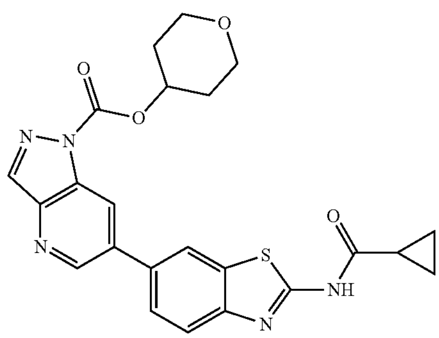 [SMILES: O=C(Nc1nc2ccc(-c3cnc4cnn(C(=O)OC5CCOCC5)c4c3)cc2s1)C1CC1] | ¹H NMR (400 MHz, DMSO-d6) δ 12.93 (s, 1H), 9.11 (s, 1H), 8.74 (s, 1H), 8.63 (s, 1H), 8.48 (s, 1H), 7.89-7.84 (m, 2H), 5.28-5.27 (m, 1H), 3.92-3.89 (m, 2H), 3.57 (d, J = 9.2 Hz, 2H), 2.12-2.10 (m, 2H), 2.01 (s, 1H), 1.87-1.85 (m, 2H), 0.95 (s, 4H). LC-MS (m/z): 463.6 [M + H]⁺ |
| C12 | 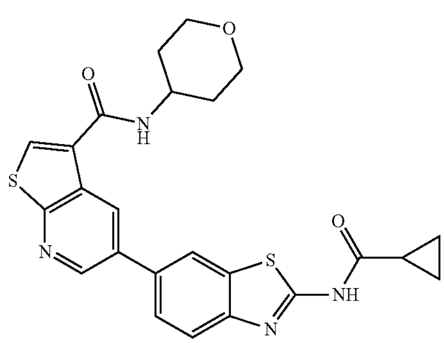 [SMILES: O=C(NC1CCOCC1)c1csc2ncc(-c3ccc4nc(NC(=O)C5CC5)sc4c3)cc12] | ¹H NMR (400 MHz, DMSO-$d_6$) δ 12.74 (s, 1H), 9.05-8.95 (m, 2H), 8.57 (s, 1H), 8.51 (d, J = 7.6 Hz, 1H), 8.42 (s, 1H), 7.87 (d, J = 8.4 Hz, 1H), 7.81 (d, J = 8.4 Hz, 1H), 4.16-3.99 (m, 1H), 3.91 (d, J = 11.6 Hz, 2H), 3.44-3.40 (m, 2H), 2.06-2.00 (m, 1H), 1.87-1.79 (m, 2H), 1.66-1.54 (m, 2H), 1.08-0.92 (m, 4H). LC-MS (m/z): 463.6 [M + H]⁺ |

TABLE 1-continued

Selected compounds synthesized

| Compd. No. | Structure | ¹H NMR and LC-MS |
|---|---|---|
| C13 | 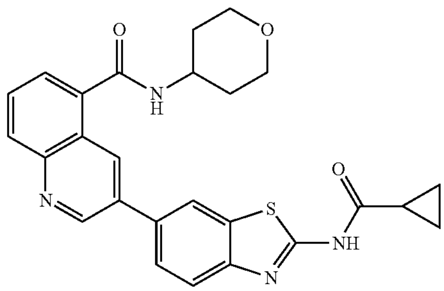 [SMILES: O=C(NC1CCOCC1)c1cccc2ncc(-c3ccc4nc(NC(=O)C5CC5)sc4c3)cc12] | ¹H NMR (400 MHz, DMSO-d$_6$) δ 12.78 (s, 1H), 9.36 (s, 1H), 8.70 (s, 1H), 8.48 (s, 1H), 12.78 (s, 1H), 8.24-8.10 (m, 1H), 7.93-7.76 (m, 3H), 7.61-7.46 (m, 1H), 4.20-4.06 (m, 1H), 3.98-3.80 (m, 2H), 3.54-3.42 (m, 2H), 2.09-1.97 (m, 1H), 1.96-1.81 (m, 2H), 1.72-1.49 (m, 2H), 1.09-0.85 (m, 4H). LC-MS (m/z): 472.7 [M + H]$^+$. |
| C14 | 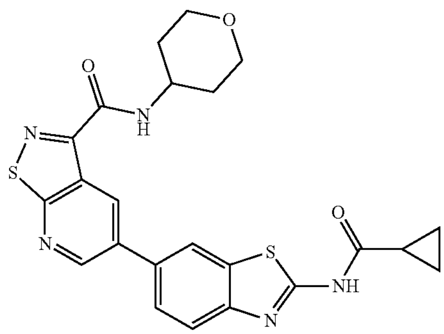 | ¹H NMR (400 MHz, DMSO-d6) δ 12.78 (s, 1H), 9.29 z (d, J = 2.0 Hz, 1H), 9.24 (d, J = 2.0 Hz, 1H), 9.00 (d, J = 8.0 Hz, 1H), 8.49 (s, 1H), 7.92-7.85 (m, 2H), 4.15-4.08 (m, 1H), 3.94-3.85 (m, 2H), 3.46-3.36 (m, 2H), 2.15-2.08 (m, 1H), 1.80-1.70 (m, 4H), 2.10-1.96 (m, 4H). LC-MS (m/z): 479.5 [M + H]$^+$. |
| C15 | 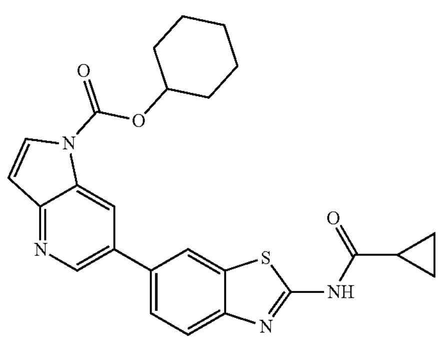 [SMILES: O=C(Nc1nc2ccc(-c3cnc4ccn(C(=O)OC5CCCCC5)c4c3)cc2s1)C1CC1] | ¹H NMR (400 MHz, DMSO-d6) δ 12.75 (s, 1H), 8.88 (s, 1H), 8.60 (s, 1H), 8.38 (s, 1H), 8.07 (d, J = 3.6 Hz, 1H), 7.86 (d, J = 8.0 Hz, 1H), 7.78 (d, J = 8.8 Hz, 1H), 6.91 (d, J = 3.6 Hz, 1H), 5.04 (s, 1H), 2.02-1.99 (m, 3H), 1.75-1.70 (m, 4H), 1.48-1.46 (m, 4H), 0.97 (s, 4H). LC-MS (m/z): 460.7 [M + H]$^+$ |
| C16 | 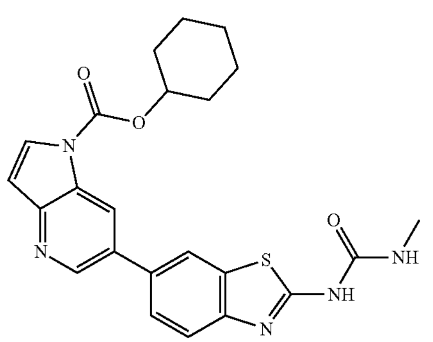 | ¹H NMR (400 MHz, DMSO-d6) δ 10.93 (s, 1H), 8.87 (d, J = 2.0 Hz, 1H), 8.56 (s, 1H), 8.30 (s, 1H), 8.07 (d, J = 4.0 Hz, 1H), 7.76-7.69 (m, 2H), 6.91 (d, J = 4.0 Hz, 1H), 6.67 (s, 1H), 5.05 (s, 1H), 2.74 (d, J = 4.0 Hz, 3H), 2.03-1.94 (m, 2H), 1.76-1.71 (m, 4H), 1.49-1.47 (m, 4H). LC-MS (m/z): 449.7 [M + H]$^+$ |

TABLE 1-continued

Selected compounds synthesized

| Compd. No. | Structure | ¹H NMR and LC-MS |
|---|---|---|
| C17 | 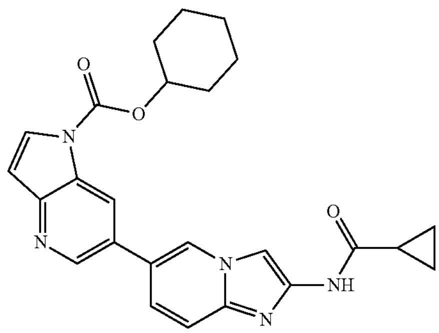 [SMILES: O=C(Nc1cn2cc(-c3cnc4ccn(C(=O)OC5CCCCC5)c4c3)ccc2n1)C1CC1] | ¹H NMR (400 MHz, DMSO-d6) δ 11.05 (s, 1H), 9.02 (s, 1H), 8.85 (s, 1H), 8.57 (s, 1H), 8.13 (s, 1H), 8.09 (s, 1H), 7.58 (s, 2H), 6.92 (s, 1H), 5.04 (s, 1H), 2.08 (s, 1H), 1.98 (s, 2H), 1.73 (s, 4H), 1.45 (s, 4H), 0.82 (s, 4H). LC-MS (m/z): 443.7 [M + H]⁺ |
| C18 | 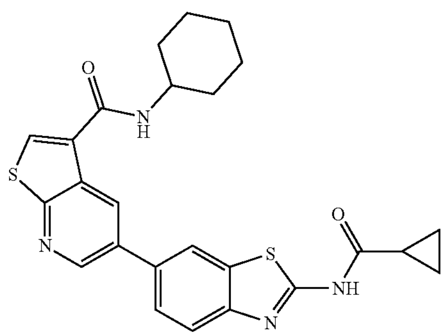 [SMILES: O=C(NC1CCCCC1)c1csc2ncc(-c3ccc4nc(NC(=O)C5CC5)sc4c3)cc12] | ¹H NMR (400 MHz, DMSO-d₆) δ 12.75 (s, 1H), 9.01 (d, J = 2.0 Hz, 1H), 8.98 (d, J = 2.4 Hz, 1H), 8.55 (s, 1H), 3.45-3.37 (m, 2H), 7.91-7.76 (m, 2H), 3.87-3.72 (m, 1H), 2.06-1.96 (m, 1H), 1.94-1.85 (m, 2H), 1.81-1.70 (m, 2H), 1.66-1.56 (m, 1H), 1.37-1.27 (m, 4H), 1.19-1.08 (m, 1H), 1.03-0.92 (m, 4H). LC-MS (m/z): 476.7 [M + H]⁺. |
| C19 | 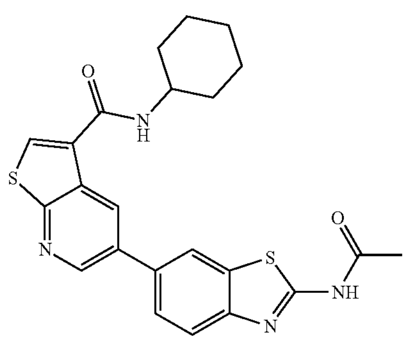 [SMILES: CC(=O)Nc1nc2ccc(-c3cnc4scc(C(=O)NC5CCCCC5)c4c3)cc2s1] | ¹H NMR (400 MHz, DMSO-d₆) δ 12.45 (s, 1H), 8.99 (d, J = 12.0 Hz, 2H), 8.56 (s, 1H), 8.42 (s, 2H), 7.93-7.75 (m, 2H), 3.91-3.63 (m, 1H), 2.23 (s, 3H), 1.97-1.83 (m, 2H), 1.83-1.68 (m, 2H), 1.42-1.11 (m, 6H). LC-MS (m/z): 450.7 [M + H]⁺. |
| C20 | 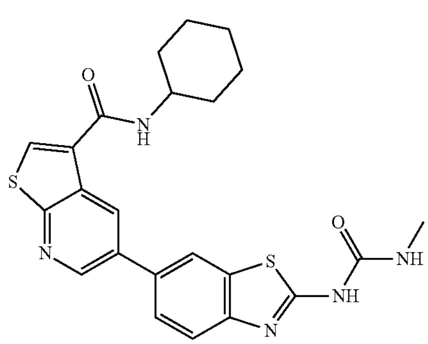 [SMILES: CNC(=O)Nc1nc2ccc(-c3cnc4scc(C(=O)NC5CCCCC5)c4c3)cc2s1] | ¹H NMR (400 MHz, DMSO-d₆) δ 10.93 (s, 1H), 8.97 (d, J = 10.0 Hz, 2H), 8.54 (s, 1H), 8.40 (d, J = 7.6 Hz, 1H), 8.33 (s, 1H), 7.74 (s, 2H), 6.66 (s, 1H), 3.92-3.69 (m, 1H), 2.74 (d, J = 4.0 Hz, 3H), 1.96-1.83 (m, 2H), 1.82-1.68 (m, 2H), 1.67-1.56 (m, 1H), 1.42-1.24 (m, 5H). LC-MS (m/z): 465.8 [M + H]⁺. |

TABLE 1-continued

Selected compounds synthesized

| Compd. No. | Structure | ¹H NMR and LC-MS |
|---|---|---|
| C21 | 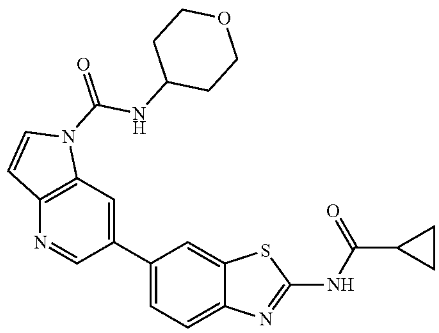 | ¹H NMR (400 MHz, DMSO-$d_6$) δ 12.73 (s, 1H), 8.82 (s, 1H), 8.76 (s, 1H), 8.36 (s, 1H), 8.29-8.19 (m, 2H), 7.85 (d, J = 8.4 Hz, 1H), 7.81-7.75 (m, 1H), 6.86 (d, J = 3.2 Hz, 1H), 3.99-3.84 (m, 3H), 3.47-3.38 (m, 2H), 2.07-1.97 (m, 1H), 1.93-1.82 (m, 2H), 1.72-1.58 (m, 2H), 1.05-1.58 (m, 4H). LC-MS (m/z): 461.8 [M + H]⁺. |
| C22 | 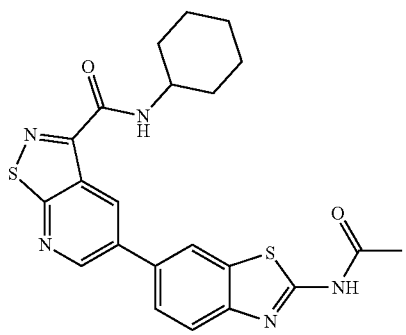 [SMILES: CC(=O)Nc1nc2ccc(-c3cnc4snc(C(=O)NC5CCCCC5)c4c3)cc2s1] | ¹H NMR (400 MHz, DMSO-$d_6$) δ 12.47 (s, 1H), 9.28 (d, J = 2.0 Hz, 1H), 9.23 (d, J = 2.0 Hz, 1H), 8.81 (d, J = 8.4 Hz, 1H), 8.49 (s, 1H), 7.92-7.85 (m, 2H), 3.92-3.85 (m, 1H), 2.23 (s, 3H), 1.90-1.82 (m, 2H), 1.78-1.70 (m, 2H), 1.65-1.58 (m, 1H), 1.50-1.18 (m, 5H). LC-MS (m/z): 451.7 [M + H]⁺. |
| C23 | 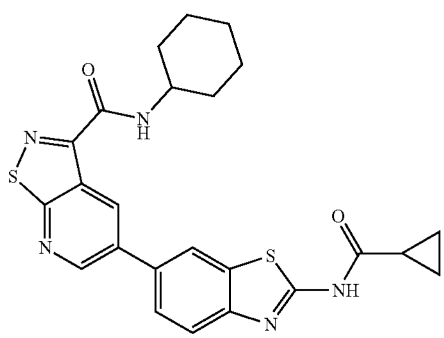 [SMILES: O=C(NC1CCCCC1)c1nsc2ncc(-c3ccc4nc(NC(=O)C5CC5)sc4c3)cc12] | ¹H NMR (400 MHz, DMSO-$d_6$) δ 12.78 (s, 1H), 9.29 (d, J = 2.0 Hz, 1H), 9.24 (d, J = 2.0 Hz, 1H), 8.81 (d, J = 8.4 Hz, 1H), 8.49 (s, 1H), 7.92-7.85 (m, 2H), 3.92-3.85 (m, 1H), 2.10-2.20 (m, 1H), 1.90-1.82 (m, 2H), 1.83-1.75 (m, 1H), 1.78-1.70 (m, 1H), 1.65-1.58 (m, 2H), 1.38-1.05 (m, 4H), 1.05-0.90 (m, 4H). LC-MS (m/z): 477.6 [M + H]⁺. |
| C24 | 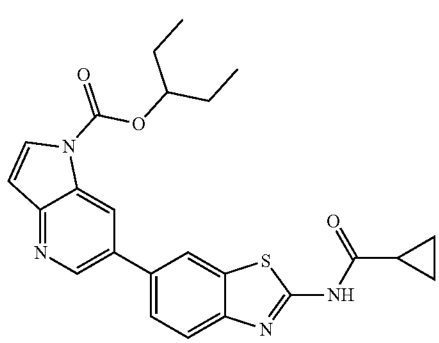 [SMILES: CCC(CC)OC(=O)n1ccc2ncc(-c3ccc4nc(NC(=O)C5CC5)sc4c3)cc21] | ¹H NMR (400 MHz, DMSO-d6) δ 12.74 (s, 1H), 8.89 (s, 1H), 8.60 (s, 1H), 8.39 (s, 1H), 8.08 (d, J = 3.6 Hz, 1H), 7.86 (d, J = 8.0 Hz, 1H), 7.78 (d, J = 8.8 Hz, 1H), 6.92 (d, J = 3.6 Hz, 1H), 4.98 (t, J = 6.2 Hz, 1H), 2.02 (s, 1H), 1.81-1.77 (m, 4H), 0.96 (s, 10H). LC-MS (m/z): 448.7 [M + H]⁺ |

TABLE 1-continued

Selected compounds synthesized

| Compd. No. | Structure | ¹H NMR and LC-MS |
|---|---|---|
| C25 | 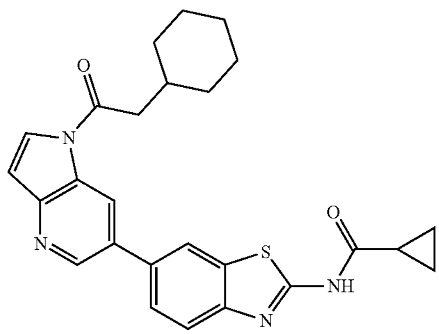 [SMILES: O=C(Nc1nc2ccc(-c3cnc4ccn(C(=O)CC5CCCCC5)c4c3)cc2s1)C1CC1] | ¹H NMR (400 MHz, DMSO-d6) δ 12.74 (s, 1H), 8.89 (s, 2H), 8.39 (s, 1H), 8.32 (s, 1H), 7.85 (d, J = 8.2 Hz, 1H), 7.79 (d, J = 8.0 Hz, 1H), 6.90 (s, 1H), 2.98 (d, J = 6.4 Hz, 2H), 2.03 (s, 1H), 1.92 (s, 1H), 1.79 (d, J = 12 Hz, 2H), 1.67 (s, 3H), 1.27-1.24 (m, 3H), 1.17-1.06 (m, 2H), 0.97 (s, 4H). LC-MS (m/z): 458.8 [M + H]⁺ |
| C26 | 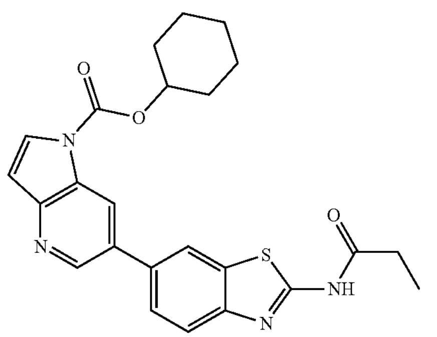 [SMILES: CCC(=O)Nc1nc2ccc(-c3cnc4ccn(C(=O)OC5CCCCC5)c4c3)cc2s1] | ¹H NMR (400 MHz, DMSO-d6) δ 12.40 (s, 1H), 8.88 (s, 1H), 8.60 (s, 1H), 8.38 (s, 1H), 8.07 (s, 1H), 7.86 (d, J = 8.0 Hz, 1H), 7.77 (d, J = 8.0 Hz, 1H), 6.91 (s, 1H), 5.04 (s, 1H), 2.53 (s, 2H), 1.98 (s, 2H), 1.75 (s, 4H), 1.48 (s, 4H), 1.13 (t, J = 7.2 Hz, 3H). LC-MS (m/z): 448.7 [M + H]⁺ |
| C27 | 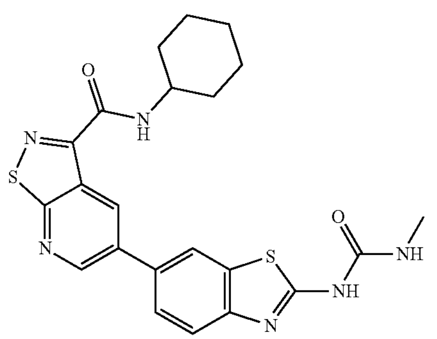 [SMILES: CNC(=O)Nc1nc2ccc(-c3cnc4snc(C(=O)NC5CCCCC5)c4c3)cc2s1] | ¹H NMR (400 MHz, DMSO-d₆) δ 10.96 (s, 1H), 9.28-9.25 (m, 1H), 9.23-9.20 (m, 1H), 8.80 (d, J = 7.6 Hz, 1H), 8.41 (s, 1H), 7.85-7.70 (m, 2H), 6.66 (s, 1H), 3.90-3.80 (m, 1H), 2.74 (d, J = 4.4 Hz, 3H), 1.88-1.72 (m, 4H), 1.67-1.57 (m, 1H), 1.50-1.40 (m, 2H), 1.37-1.28 (m, 2H), 1.18-1.08 (m, 1H). LC-MS (m/z): 466.7 [M + H]⁺. |
| C28 | 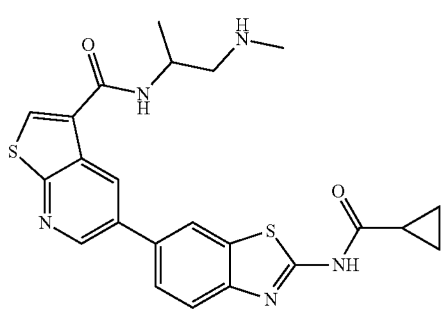 [SMILES: CNCC(C)NC(=O)c1csc2ncc(-c3ccc4nc(NC(=O)C5CC5)sc4c3)cc12] | ¹H NMR (400 MHz, DMSO-d₆) δ 9.03 (s, 1H), 9.00 (s, 1H), 8.59 (s, 1H), 8.52 (d, J = 8.0 Hz, 1H), 8.40 (s, 1H), 7.88 (d, J = 8.4 Hz, 1H), 7.80 (d, J = 8.8 Hz, 1H), 4.42-4.26 (m, 1H), 2.95 (d, J = 8.4 Hz, 2H), 2.53 (s, 3H), 2.10-1.92 (m, 1H), 1.24-1.20 (m, 3H), 1.06-0.89 (m, 4H). LC-MS (m/z): 465.7 [M + H]⁺. |

TABLE 1-continued

Selected compounds synthesized

| Compd. No. | Structure | ¹H NMR and LC-MS |
|---|---|---|
| C29 | 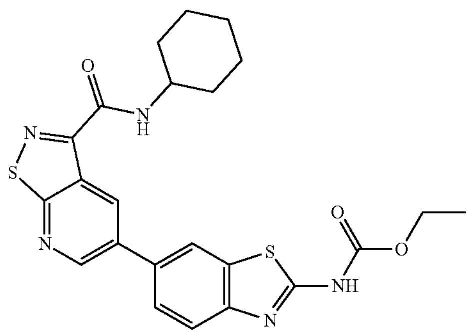 [SMILES: CCOC(=O)Nc1nc2ccc(-c3cnc4snc(C(=O)NC5CCCCC5)c4c3)cc2s1] | ¹H NMR (400 MHz, DMSO-d$_6$) δ 12.18 (s, 1H), 9.29-9.27 (m, 1H), 9.25-9.23 (m, 1H), 8.82 (d, J = 8.4 Hz, 1H), 8.49 (s, 1H), 7.89-7.80 (m, 2H), 4.31-4.23 (m, 2H), 3.90-3.77 (m, 1H), 2.06-1.96 (m, 1H), 1.88-1.72 (m, 4H), 1.66-1.58 (m, 1H), 1.50-1.40 (m, 2H), 1.36-1.26 (m, 5H). LC-MS (m/z): 481.6 [M + H]$^+$. |
| C30 | 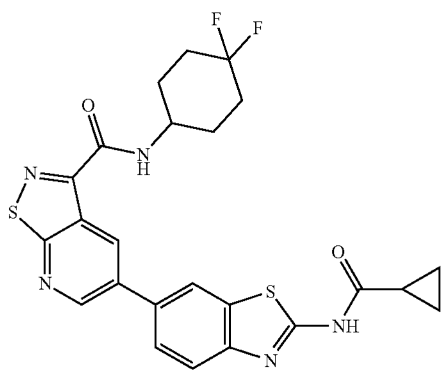 [SMILES: O=C(NC1CCC(F)(F)CC1)c1nsc2ncc(-c3ccc4nc(NC(=O)C5CC5)sc4c3)cc12] | ¹H NMR (400 MHz, DMSO-d$_6$) δ 12.78 (s, 1H), 9.29 (d, J = 2.0 Hz, 1H), 9.23 (d, J = 2.0 Hz, 1H), 9.02 (d, J = 7.2 Hz, 1H), 8.50 (s, 1H), 8.00-7.85 (m, 2H), 4.16-3.98 (m, 1H), 2.16-1.87 (m, 7H), 1.84-1.71 (m, 2H), 1.04-0.93 (m, 4H). LC-MS (m/z): 513.6 [M + H]$^+$. |
| C31 | 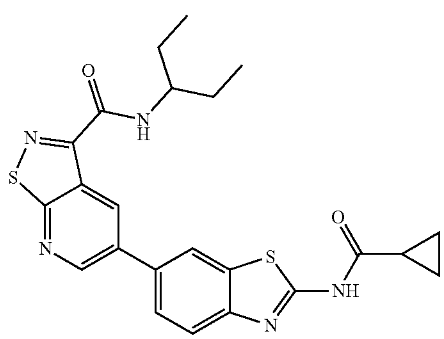 [SMILES: CCC(CC)NC(=O)c1nsc2ncc(-c3ccc4nc(NC(=O)C5CC5)sc4c3)cc12] | ¹H NMR (400 MHz, DMSO) δ 12.78 (s, 1H), 9.29 (d, J = 2.4 Hz, 1H), 9.23 (d, J = 2.0 Hz, 1H), 8.67 (d, J = 8.8 Hz, 1H), 8.50 (s, 1H), 7.85-7.83 (m, 2H), 3.90-3.78 (m, 1H), 2.10-1.90 (m, 1H), 1.65-1.53 (m, 4H), 1.00-0.95 (m, 4H), 0.93-0.86 (m, 6H). LC-MS (m/z): 465.7 [M + H]$^+$. |
| C32 | 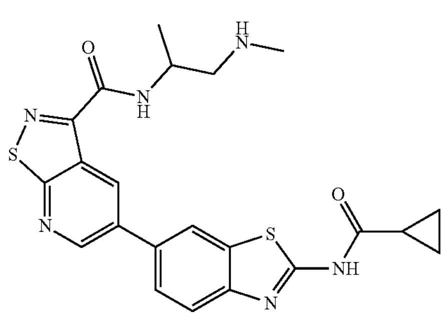 [SMILES: CNCC(C)NC(=O)c1nsc2ncc(-c3ccc4nc(NC(=O)C5CC5)sc4c3)cc12] | ¹H NMR (400 MHz, DMSO-d$_6$) δ 9.30 (s, 1H), 9.27 (s, 1H), 8.80 (d, J = 8.0 Hz, 1H), 8.49 (s, 1H), 7.94-7.84 (m, 2H), 4.34-4.16 (m, 1H), 2.88-2.80 (m, 1H), 2.79-2.71 (m, 1H), 2.39 (s, 3H), 2.08-1.90 (m, 2H), 1.33-1.24 (m, 3H), 1.04-0.94 (m, 4H). LC-MS (m/z): 466.7 [M + H]$^+$. |

TABLE 1-continued

Selected compounds synthesized

| Compd. No. | Structure | ¹H NMR and LC-MS |
|---|---|---|
| C33 | 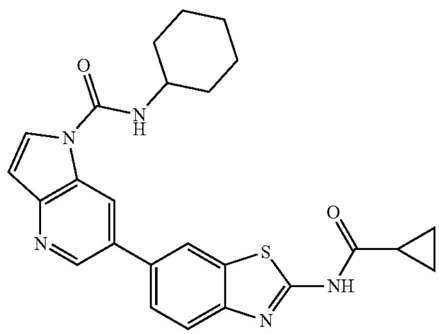 [SMILES: O=C(Nc1nc2ccc(-c3cnc4ccn(C(=O)NC5CCCCC5)c4c3)cc2s1)C1CC1] | ¹H NMR (400 MHz, DMSO-d6) δ 12.72 (s, 1H), 8.81 (s, 1H), 8.76 (s, 1H), 8.36 (s, 1H), 8.23 (d, J = 3.2 Hz, 1H), 8.14 (d, J = 7.6 Hz, 1H), 7.85 (d, J = 8.4 Hz, 1H), 7.78 (d, J = 8.4 Hz, 1H), 6.83 (d, J = 3.2 Hz, 1H), 3.70 (s, 1H), 2.02-1.93 (m, 4H), 1.77 (d, J = 10.4 Hz, 2H), 1.63 (d, J = 12.4 Hz, 1H), 1.39-1.31 (m, 4H), 0.97 (s, 4H). LC-MS (m/z): 459.7 [M + H]⁺ |
| C34 | 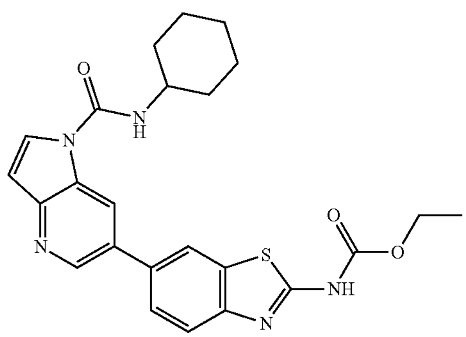 [SMILES: CCOC(=O)Nc1nc2ccc(-c3cnc4ccn(C(=O)NC5CCCCC5)c4c3)cc2s1] | ¹H NMR (400 MHz, DMSO-d6) δ 12.13 (s, 1H), 8.87 (s, 1H), 8.60 (s, 1H), 8.37 (s, 1H), 8.07 (d, J = 3.2 Hz, 1H), 7.82 (d, J = 8.2 Hz, 1H), 7.75 (d, J = 8 Hz, 1H), 6.91 (d, J = 2.8 Hz, 1H), 5.05 (s, 1H), 4.29-4.24 (m, 2H), 1.98 (s, 2H), 1.73 (s, 4H), 1.48 (s, 4H), 1.29 (t, J = 7.2 Hz, 3H). LC-MS (m/z): 464.7 [M + H]⁺ |
| C35 | 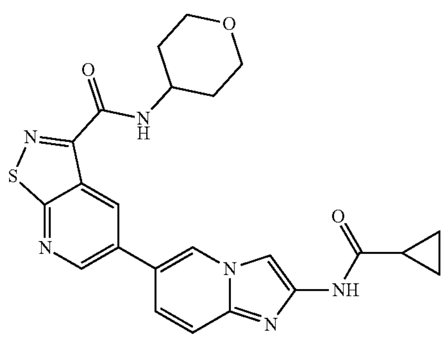 [SMILES: O=C(NC1CCOCC1)c1nsc2ncc(-c3ccc4nc(NC(=O)C5CC5)cn4c3)cc12] | ¹H NMR (400 MHz, DMSO-d₆) δ 11.06 (s, 1H), 9.26 (s, 1H), 9.23 (s, 1H), 9.15 (s, 1H), 9.01 (d, J = 8.0 Hz, 1H), 8.14 (s, 1H), 7.68 (d, J = 8.0 Hz, 1H), 7.60 (d, J = 9.2 Hz, 1H), 4.15-4.03 (m, 1H), 3.96-3.85 (m, 2H), 3.45-3.37 (m, 2H), 2.00-1.90 (m, 1H), 1.80-1.58 (m, 4H), 0.89-0.80 (m, 4H). LC-MS (m/z): 462.7 [M + H]⁺ |
| C36 | 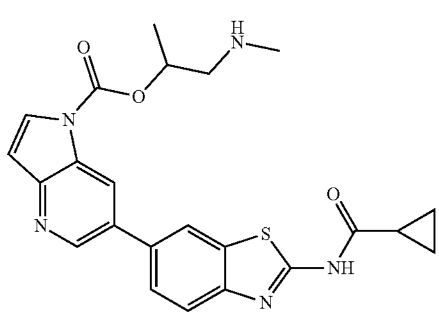 [SMILES: CNCC(C)OC(=O)n1ccc2ncc(-c3ccc4nc(NC(=O)C5CC5)sc4c3)cc21] | ¹H NMR (400 MHz, DMSO-d6) δ 12.78 (s, 1H), 9.15 (s, 2H), 9.02 (s, 1H), 8.81 (s, 1H), 8.46 (s, 1H), 8.42 (s, 1H), .7.90-7.84 (m, 2H), 7.01 (d, J = 3.2 Hz, 1H), 5.41 (s, 1H), 3.44-3.41 (m, 1H), 3.32 (s, 1H), 2.62 (s, 3H), 2.04 (s, 1H), 1.47 (d, J = 6 Hz, 3H), 0.99 (s, 4H). LC-MS (m/z): 449.7 [M + H]⁺ |

TABLE 1-continued

Selected compounds synthesized

| Compd. No. | Structure | ¹H NMR and LC-MS |
|---|---|---|
| C37 | 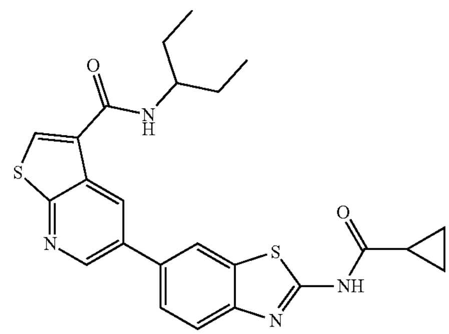 [SMILES: CCC(CC)NC(=O)c1csc2ncc(-c3ccc4nc(NC(=O)C5CC5)sc4c3)cc12] | ¹H NMR (400 MHz, DMSO-$d_6$) δ 12.75 (s, 1H), 9.02 (s, 1H), 8.99 (s, 1H), 8.59 (s, 1H), 8.42 (s, 1H), 8.25 (d, J = 8.4 Hz, 1H), 7.88 (d, J = 8.4 Hz, 1H), 7.82 (d, J = 8.4 Hz, 1H), 3.88-3.75 (m, 1H), 2.08-1.96 (m, 1H), 1.65-1.46 (m, 4H), 1.04-0.95 (m, 4H), 0.94-0.85 (m, 6H). LC-MS (m/z): 466.6 [M + H]⁺ |
| C38 | 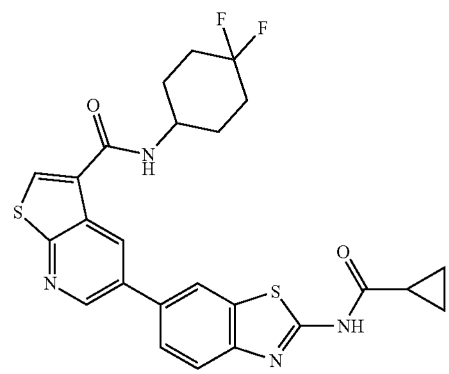 [SMILES: O=C(NC1CCC(F)(F)CC1)c1csc2ncc(-c3ccc4nc(NC(=O)C5CC5)sc4c3)cc12] | ¹H NMR (400 MHz, DMSO-$d_6$) δ 12.75 (s, 1H), 9.00 (s, 1H), 8.57 (s, 1H), 8.51 (d, J = 7.6 Hz, 1H), 8.42 (s, 1H), 7.88 (d, J = 8.0 Hz, 1H), 7.82 (d, J = 9.6 Hz, 1H), 4.04 (s, 1H), 2.09-1.94 (m, 8H), 1.68 (s, 2H), 0.97 (s, 4H). LC-MS (m/z): 512.6 [M + H]⁺ |
| C39 | 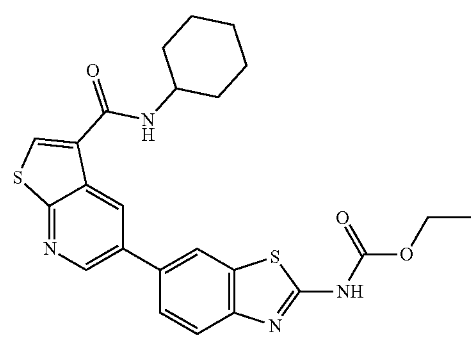 [SMILES: CCOC(=O)Nc1nc2ccc(-c3cnc4scc(C(=O)NC5CCCCC5)c4c3)cc2s1] | ¹H NMR (400 MHz, DMSO-d6) δ 12.13 (br s, 1H), 9.08-8.91 (m, 2H), 8.55 (s, 1H), 8.40 (s, 2H), 7.80 (s, 2H), 4.35-4.19 (m, 2H), 3.89-3.72 (m, 1H), 2.08-1.83 (m, 3H), 1.83-1.68 (m, 2H), 1.69-1.52 (m, 1H), 1.42-1.23 (m, 7H). |
| C40 | 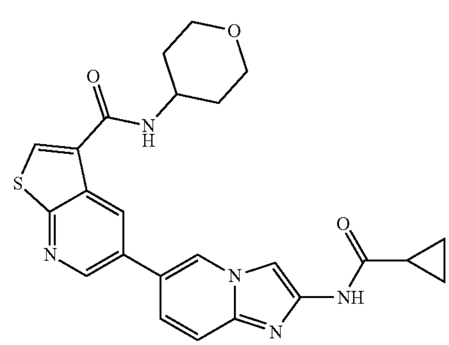 [SMILES: O=C(NC1CCOCC1)c1csc2ncc(-c3ccc4nc(NC(=O)C5CC5)cn4c3)cc12] | ¹H NMR (400 MHz, DMSO-$d_6$) δ 11.54 (s, 1H), 9.21 (s, 1H), 9.02 (s, 1H), 8.97 (s, 1H), 8.64 (s, 1H), 8.58 (d, J = 7.6 Hz, 1H), 8.16 (s, 1H), 7.92 (d, J = 9.2 Hz, 1H), 7.76 (d, J = 9.2 Hz, 1H), 4.15-3.75 (m, 3H), 3.47-3.32 (m, 2H), 2.01-1.90 (m, 1H), 1.85-1.80 (m, 2H), 1.60-1.50 (m, 2H), 0.89-0.80 (m, 4H). LC-MS (m/z): 462.7 [M + H]⁺ |

TABLE 1-continued

Selected compounds synthesized

| Compd. No. | Structure | $^1$H NMR and LC-MS |
|---|---|---|
| C41 | 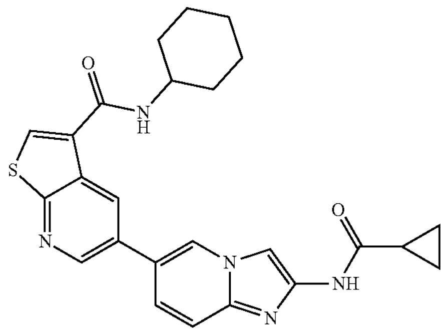 [SMILES: O=C(NC1CCCCC1)c1csc2ncc(-c3ccc4nc(NC(=O)C5CC5)cn4c3)cc12] | $^1$H NMR (400 MHz, DMSO-d$_6$) δ 11.04 (s, 1H), 9.06 (s, 1H), 8.96 (s, 1H), 8.95 (s, 1H), 8.56 (s, 1H), 8.42 (d, J = 7.6 Hz, 1H), 8.13 (s, 1H), 7.65-7.55 (m, 2H), 3.80-3.75 (m, 1H), 2.00-1.90 (m, 3H), 1.80-1.70 (m, 2H), 1.67-1.57 (m, 1H), 1.40-1.30 (m, 4H), 1.16-1.11 (m, 1H), 0.89-0.75 (m, 4H). LC-MS (m/z): 459.7 [M + H]$^+$ |
| C42 | 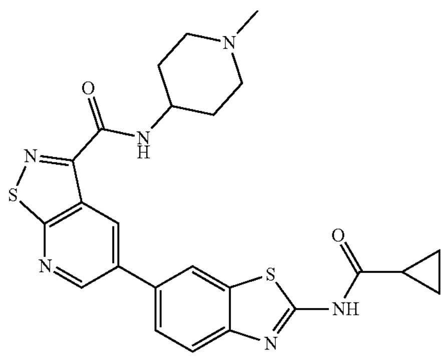 [SMILES: CN1CCC(NC(=O)c2nsc3ncc(-c4ccc5nc(NC(=O)C6CC6)sc5c4)cc23)CC1] | $^1$H NMR (400 MHz, DMSO-d$_6$) 12.76 (br s, 1H), 9.28 (s, 1H), 9.24 (s, 1H), 8.89 (d, J = 8.0 Hz, 1H), 8.49 (s, 1H), 7.96-7.80 (m, 2H), 3.90-3.73 (m, 1H), 2.84-2.71 (m, 2H), 2.17 (s, 3H), 2.07-1.89 (m, 3H), 1.83-1.64 (m, 4H), 1.04-0.90 (m, 4H). MS (ESI/APCI) m/z 492.7 [M + H]$^+$ |
| C43 | 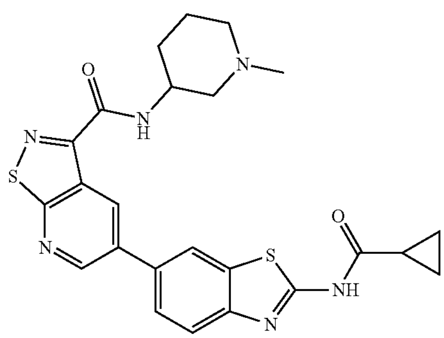 [SMILES: CN1CCCC(NC(=O)c2nsc3ncc(-c4ccc5nc(NC(=O)C6CC6)sc5c4)cc23)C1] | $^1$H NMR (400 MHz, DMSO-d$_6$) 12.78 (br s, 1H), 9.29 (s, 1H), 9.25 (s, 1H), 8.78-8.62 (m, 1H), 8.50 (s, 1H), 7.99-7.76 (m, 2H), 4.11-3.96 (m, 1H), 2.80-2.57 (m, 2H), 2.19 (s, 3H), 2.15-1.95 (m, 3H), 1.80-1.60 (m, 2H), 1.59-1.45 (m, 2H), 1.06-0.89 (m, 4H). MS (ESI/APCI) m/z 492.7 [M + H]$^+$ |

Biological Activities

Example 42

The efficacies of Compounds C1-C41 were tested for their inhibition activities in necroptosis assays as follows:
1. Compounds Tested for Necroptosis Inhibition Activities in HT29 Cell Assay For this assay, HT29 cells were added to 96-well plates and then were pre-treated with 10 μM of the test compound for one hour. Then the cells were treated with tumor necrosis factor alpha (TNF-α, 40 ng/mL), Smacmimetic (cIAP inhibitor) (100 nM) and z-VAD (capase inhibitor, from calbiochem) (20 μM) for 48 hours, and the viability of cells was quantified. DMSO pretreatment group was used as negative controls, Nec-1 (known necroptosis inhibitor, from Biomol) pretreatment group was used as positive controls.

Figure 2:
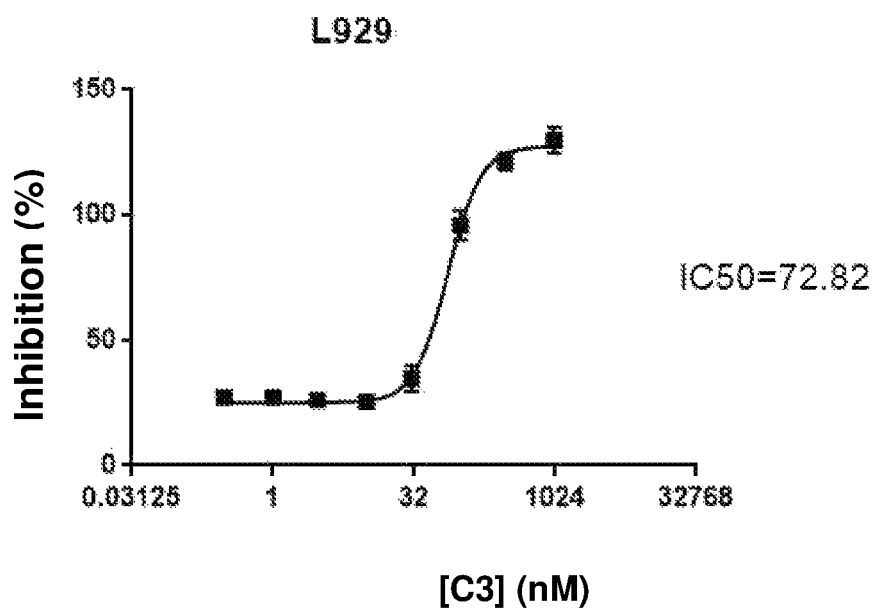
FIG. 2 depicts the inhibition of TNF-α induced-necrosis in L929 cells by compound C3 in Example 42.

The compounds C3 was taken as an example, and the results are shown in FIG. 1. As shown in FIG. 1, the IC$_{50}$ of Compound C3 in the in Vitro HT29 Cell Assay is 9.6 nM.
2. Compounds Tested for Necroptosis Inhibition Activities in L929 Cell Assay Mouse L929 mouse skin fibroblast cells were added to 96-well plates and then were pre-treated with 10 μM of the test compound for one hour. Then the cells were treated with TNF-α (40 ng/mL, lab-made) and z-VAD (capase inhibitor, from calbiochem) (20 μM) for 48 hours, and the viability of cells was quantified by detecting adenosine triphosphate (ATP) levels. DMSO pretreatment group was used as negative controls, Nec-1 (known necroptosis inhibitor, from Biomol) pretreatment group was used as positive controls. The compounds C3 was taken as an example, and the results are shown in FIG. 2. As shown in FIG. 2, the IC$_{50}$ of Compound C3 in the in Vitro HT29 Cell Assay is 72.82 nM

TABLE 2

Necroptosis inhibition activities of selected compounds

| Compound No. | HT29 IC$_{50}$(nM) | L929 IC$_{50}$(nM) | Compound No. | HT29 IC$_{50}$(nM) | L929 IC$_{50}$(nM) |
|---|---|---|---|---|---|
| C1 | 43 | ND | C21 | 22 | ND |
| C2 | 11000 | ND | C22 | 35 | ND |
| C3 | 9.6 | 72.82 | C23 | 5.3 | 1.7 |
| C4 | 83 | 3.2 | C24 | 33 | ND |
| C5 | 5.6 | 17 | C25 | 29 | ND |
| C6 | 56 | 50 | C26 | 50 | ND |
| C7 | 32 | ND | C27 | 33 | ND |
| C8 | 440 | 17 | C28 | 380 | ND |
| C9 | 5200 | ND | C29 | 3.1 | ND |
| C10 | 12000 | ND | C30 | 10 | 0.8 |
| C11 | 4100 | ND | C31 | 11 | ND |
| C12 | 7.3 | 1.5 | C32 | 1400 | ND |
| C13 | 13000 | ND | C33 | 4.6 | 0.3 |
| C14 | 4.7 | 1.3 | C34 | 150 | ND |
| C15 | 7.0 | ND | C35 | 160 | ND |
| C16 | 25 | ND | C36 | 16000 | ND |
| C17 | 16 | ND | C37 | 3.2 | ND |
| C18 | 1.0 | 0.3 | C38 | 1.8 | ND |
| C19 | 11 | ND | C39 | 48 | ND |
| C20 | 1.6 | 0.6 | C40 | 60 | ND |
| C41 | 2.0 | ND | C42 | 3000 | 321 |
| C43 | ND | ND | Nec-1 | 300 | 1250 |

In Table 2, (1) "ND" indicates "not detected."

As shown in FIGS. 1 and 2 and Table 2, the heteroaryl compounds of the present disclosure can be effective inhibitors for necrosis, can effectively block cell necrosis signaling pathway, and can be used in treating or preventing diseases caused by or associate with abnormal necrosis signaling pathways.

The present application may include a variety of embodiments. All technical solutions formed by the equivalent variation or the equivalent modification fall within the protection scope of the present application.

What is claimed is:

1. A compound selected from the group consisting of:

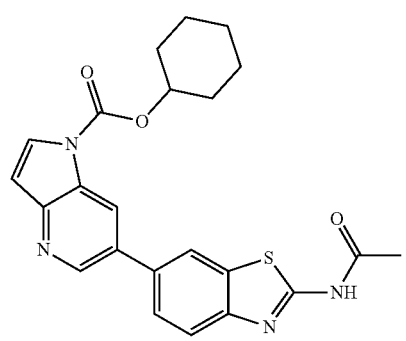

C1

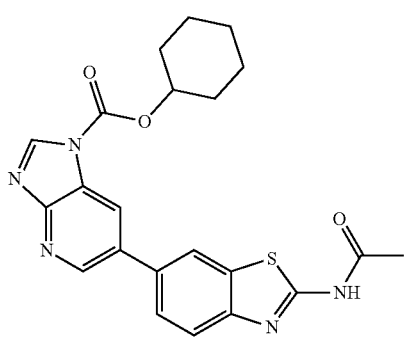

C2

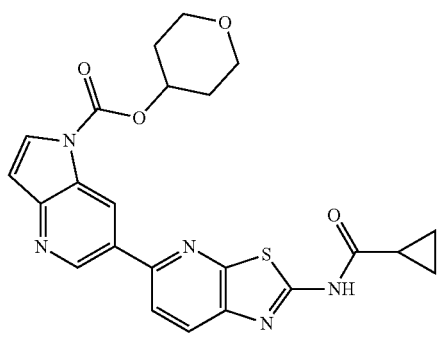

C3

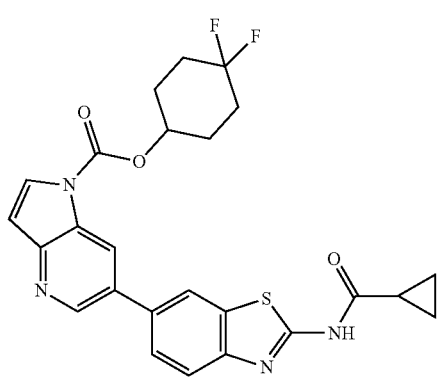

C4

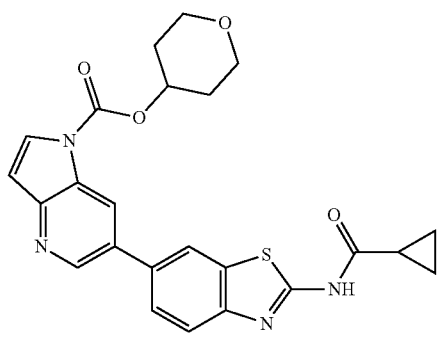

C5

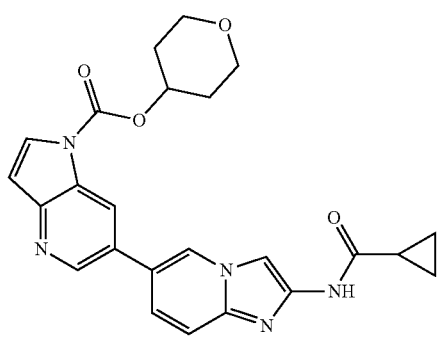

C6

127
-continued
C7
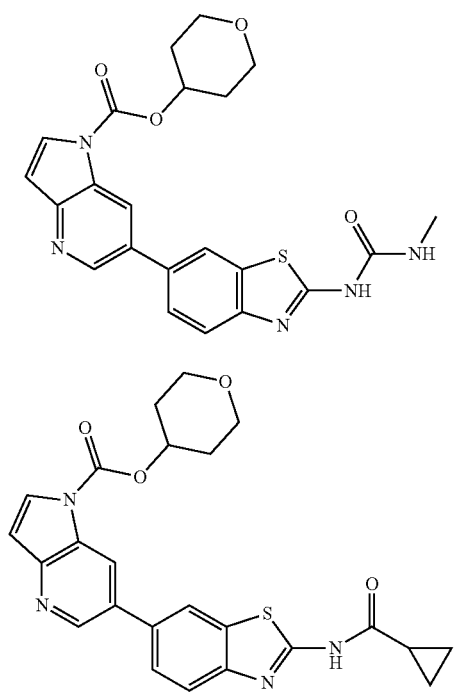
C8
C9
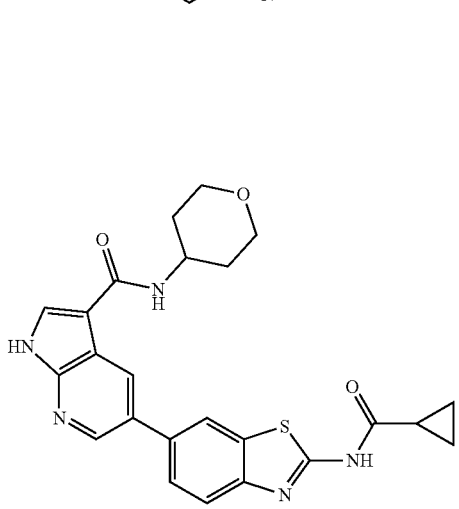
C10
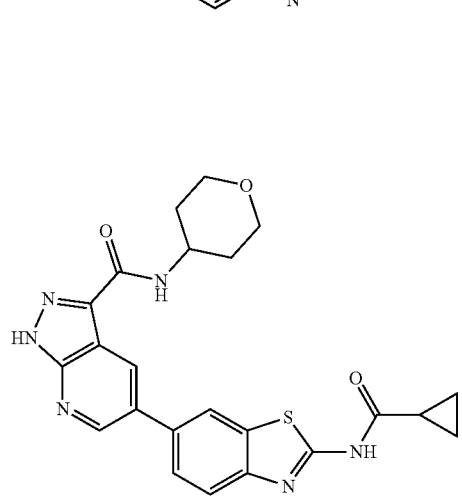
128
-continued
C11
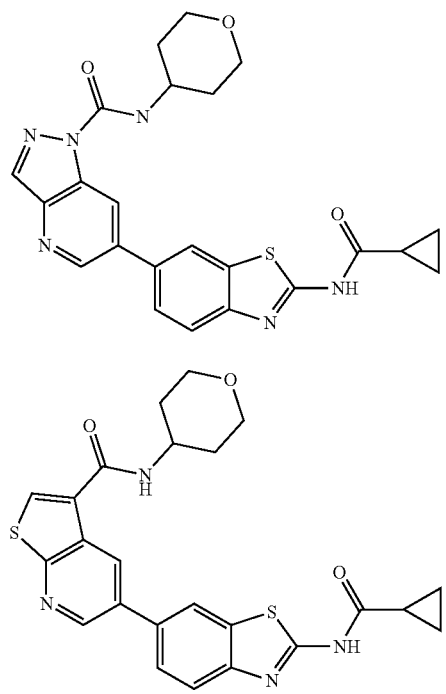
C12
C13
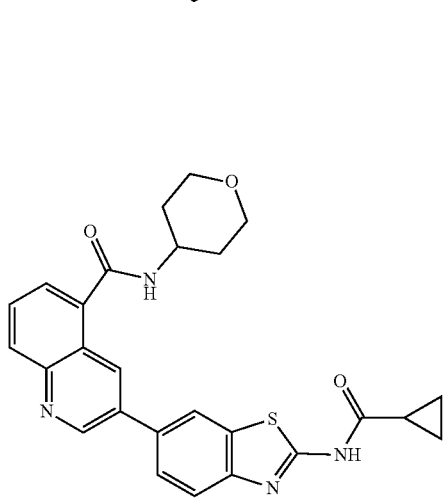
C14
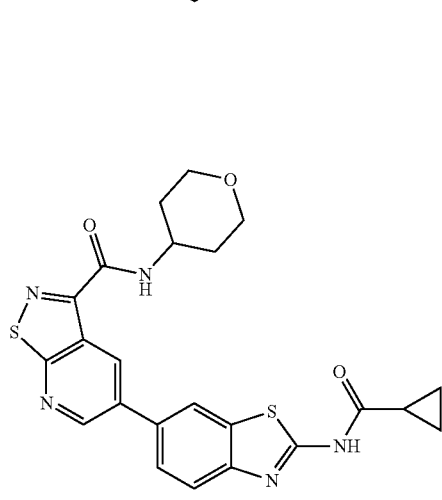

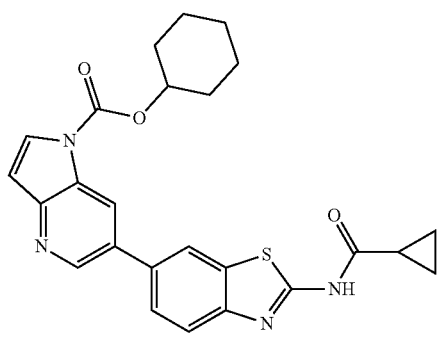
C15
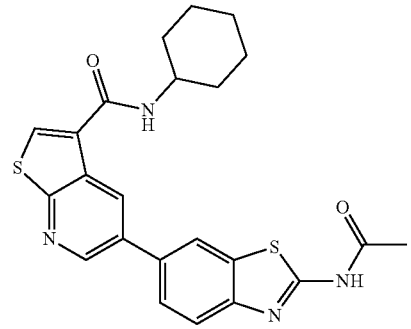
C19
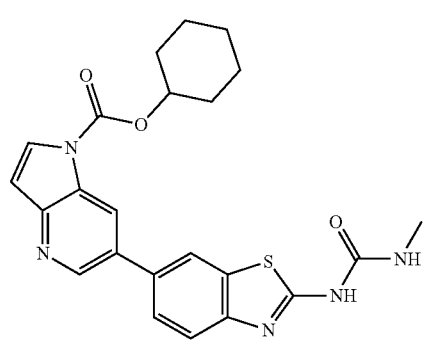
C16
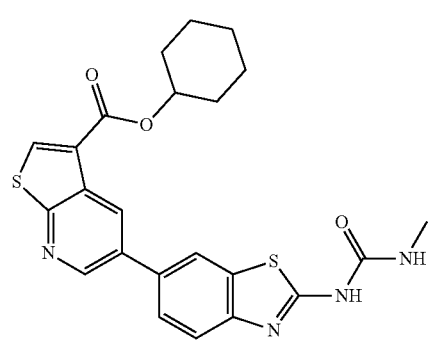
C20
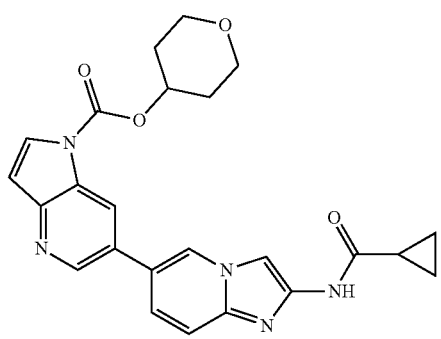
C17
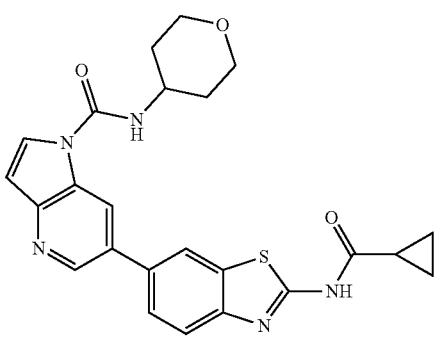
C21
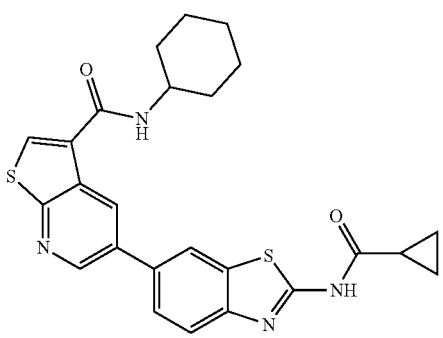
C18
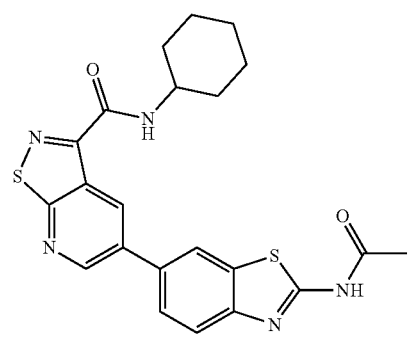
C22

131
-continued
C23
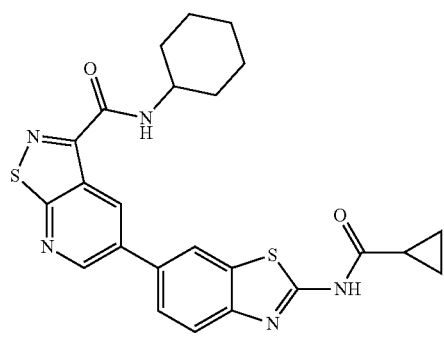
C24
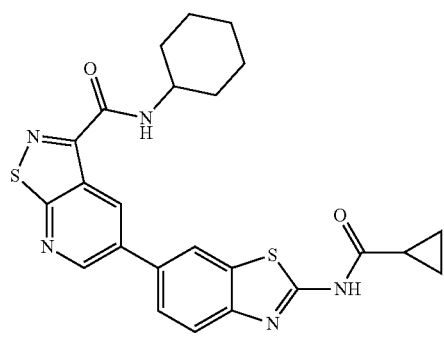
C25
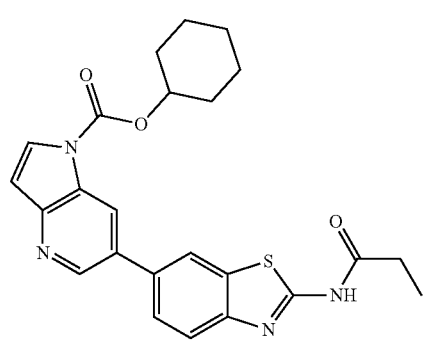
C26
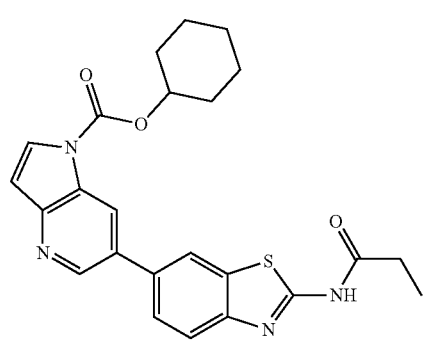
132
-continued
C27
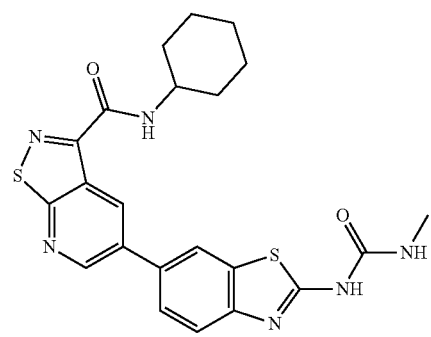
C28
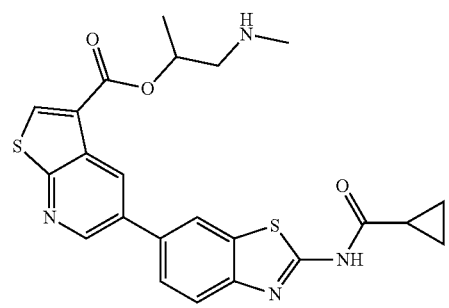
C29
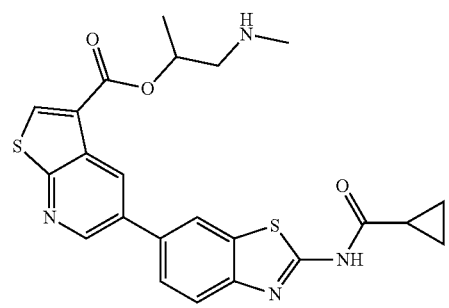
C30
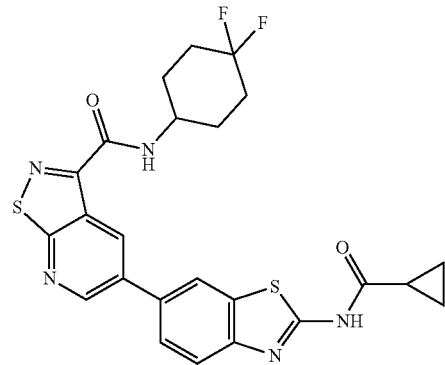

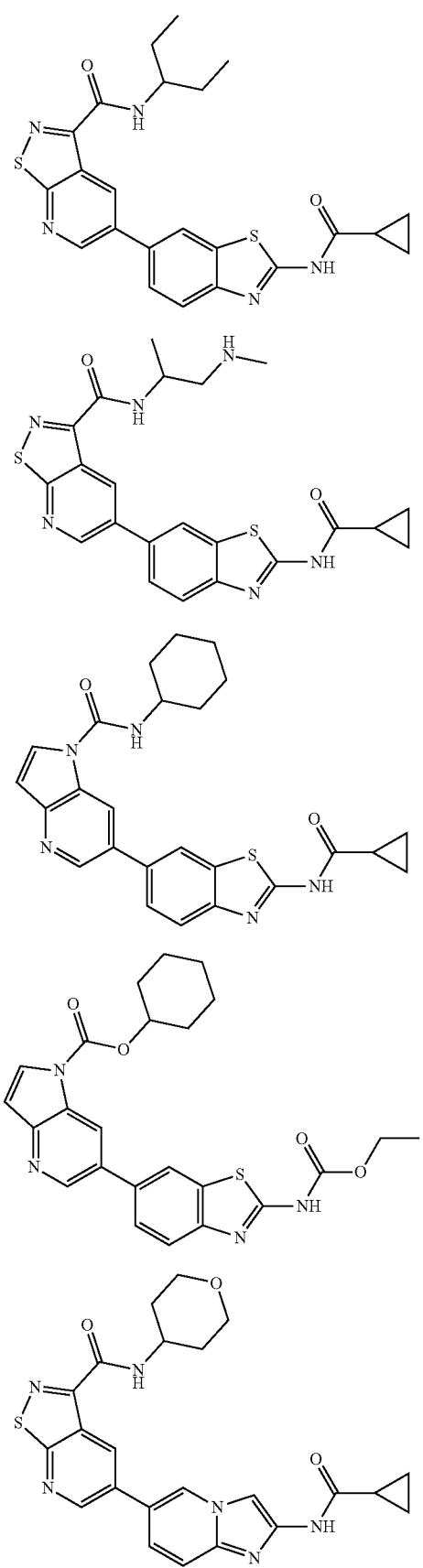

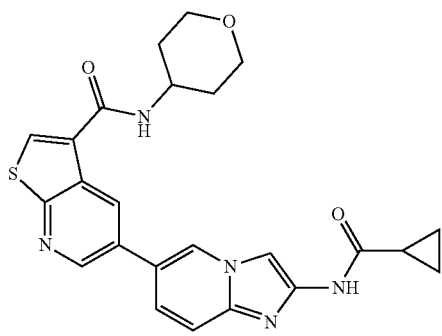

C40

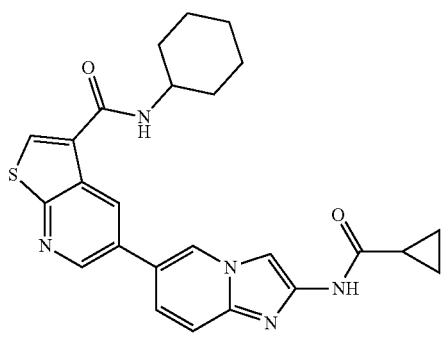

C41

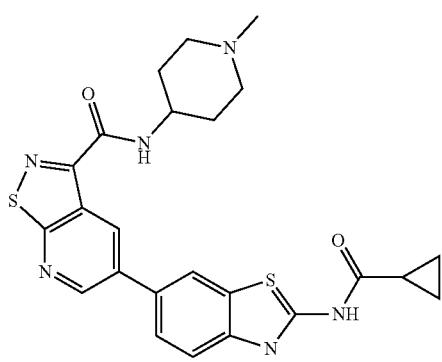

C42

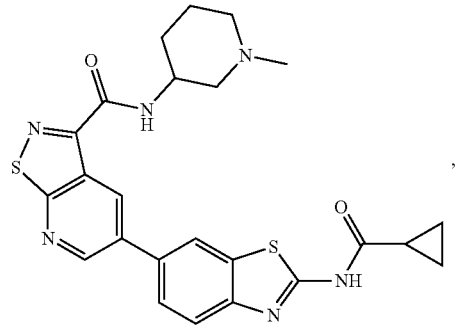

C43 or a stereoisomer, hydrate, solvate, co-crystal, or tautomer, or pharmaceutically acceptable salt thereof.

2. A pharmaceutical composition comprising a therapeutically effective amount of a compound of claim 1, or a stereoisomer, hydrate, solvate, co-crystal, or tautomer, or pharmaceutically acceptable salt thereof, and at least one component selected from the list of pharmaceutically acceptable carrier, diluent, adjuvant and excipient.

3. A compound having a structure of:

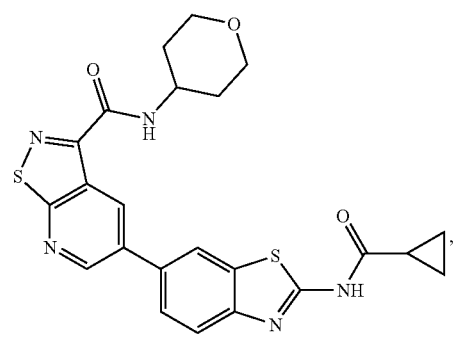

C14 or a stereoisomer, hydrate, solvate, co-crystal, or tautomer, or pharmaceutically acceptable salt thereof.

4. A pharmaceutical composition comprising a therapeutically effective amount of a compound of claim 3, or a stereoisomer, hydrate, solvate, co-crystal, or tautomer, or pharmaceutically acceptable salt thereof, and at least one component selected from the list of pharmaceutically acceptable carrier, diluent, adjuvant and excipient.

* * * * *